US011331303B2

(12) United States Patent
Scaife

(10) Patent No.: US 11,331,303 B2
(45) Date of Patent: *May 17, 2022

(54) SUBLINGUAL OR BUCCAL ADMINISTRATION OF DIM FOR TREATMENT OF SKIN DISEASES

(71) Applicant: SKINTECH LIFE SCIENCE LIMITED, Middlesex (GB)

(72) Inventor: Michael C. Scaife, Pittsburgh, PA (US)

(73) Assignee: SKINTECH LIFE SCIENCE LIMITED, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/333,375

(22) PCT Filed: Sep. 15, 2017

(86) PCT No.: PCT/IB2017/001290
§ 371 (c)(1),
(2) Date: Mar. 14, 2019

(87) PCT Pub. No.: WO2018/051183
PCT Pub. Date: Mar. 22, 2018

(65) Prior Publication Data
US 2019/0343798 A1   Nov. 14, 2019

Related U.S. Application Data

(60) Provisional application No. 62/395,234, filed on Sep. 15, 2016.

(51) Int. Cl.
*A61K 31/404* (2006.01)
*A61P 17/10* (2006.01)
*A61K 31/07* (2006.01)
*A61K 9/00* (2006.01)

(52) U.S. Cl.
CPC .......... *A61K 31/404* (2013.01); *A61K 9/006* (2013.01); *A61K 31/07* (2013.01); *A61P 17/10* (2018.01)

(58) Field of Classification Search
CPC .................................................. A61K 31/404
See application file for complete search history.

(56) References Cited

U.S. PATENT DOCUMENTS

2006/0264497 A1   11/2006   Zeligs
2014/0220063 A1    8/2014   Asari et al.

FOREIGN PATENT DOCUMENTS

| CN | 103961701 A | 8/2014 |
| CN | 103501772 B | 6/2018 |
| DE | 102013104441 A1 | 10/2014 |
| JP | 2014508793 A | 4/2014 |
| WO | WO-2012130698 A1 | 10/2012 |
| WO | WO-2016012523 A1 | 1/2016 |
| WO | WO-2018051183 A1 | 3/2018 |

OTHER PUBLICATIONS

Chu et al. In Vitro and in Vivo Induction of Cytochrome P450: A Survey of the Current Practices and Recommendations: A Pharmaceutical Research and Manufacturers of America Perspective. Drug Metabl Dispos 37(7):1339-1354 (2009).
PCT/IB2017/001290 International Search Report and Written Opinion dated Jan. 12, 2018.
Office Action for related Japanese Application No. 2019-512744, dated Aug. 4, 2021, 8 pages.

*Primary Examiner* — Yong S. Chong
(74) *Attorney, Agent, or Firm* — Procopio, Cory, Hargreaves & Savitch LLP

(57) ABSTRACT

Described herein are methods for treating one or more skin conditions by administering, via the sublingual or buccal route, a composition comprising substituted or unsubstituted diindolylmethane. In particular, methods are provided for improving the bioavailability and pharmacokinetic parameters of substituted or unsubstituted diindolylmethane following a sublingual or buccal administration, relative to an oral administration.

10 Claims, 2 Drawing Sheets

SUBLINGUAL OR BUCCAL ADMINISTRATION OF DIM FOR TREATMENT OF SKIN DISEASES

CROSS-REFERENCE

This application is a U.S. National Stage entry of International Application No. PCT/IB2017/001290, filed Sep. 15, 2017, which claims the benefit of U.S. Provisional Application No. 62/395,234, filed Sep. 15, 2016, each of which is incorporated by reference herein in their entirety.

BACKGROUND OF THE DISCLOSURE

Acne is a skin condition characterized by areas of blackheads, whiteheads, pimples, greasy skin, and possibly scarring. Rosacea is a chronic skin condition characterized by facial redness, small and superficial dilated blood vessels on facial skin, papules, pustules, and swelling. Acne and Rosacea affect all ages. Treatment of either condition by oral administration of diindolylmethane sometimes results in poor efficacy.

SUMMARY OF THE DISCLOSURE

One embodiment provides a method of treating acne in a subject in need thereof comprising administering to the subject a composition comprising a substituted or unsubstituted diindolylmethane, wherein the composition is administered by a sublingual or buccal route. In some embodiments, the composition further comprises a substituted or unsubstituted retinoic acid based component. In some embodiments, the method of claim 2, wherein the retinoic acid based component is vitamin A. In some embodiments, the composition further comprises a vitamin A palmitate. In some embodiments, the administration of the composition by the sublingual or buccal route increases bioavailability of the substituted or unsubstituted diindolylmethane by about 1-fold to about 50-fold compared to bioavailability of a substituted or unsubstituted diindolylmethane of a comparative composition administered by oral route at the same delivery dose. In some embodiments, following administration of the composition by the sublingual or buccal route Cmax of the substituted or unsubstituted diindolylmethane in plasma increases by about 1-fold to about 50-fold compared to Cmax of a substituted or unsubstituted diindolylmethane of a comparative composition administered by oral route at the same delivery dose. In some embodiments, following administration of the composition by the sublingual or buccal route the AUC of the substituted or unsubstituted diindolylmethane in plasma increases by about 1-fold to about 50-fold compared to the AUC of a substituted or unsubstituted diindolylmethane of a comparative composition administered by oral route at the same delivery dose. In some embodiments, following administration of the composition by the sublingual or buccal route the Tmax of the substituted or unsubstituted diindolylmethane in plasma decreases by about 1-fold to about 50-fold compared to the Tmax of a substituted or unsubstituted diindolylmethane of a comparative composition administered by oral route at the same delivery dose. In some embodiments, a percentage of the composition effluxed by P-gp following the sublingual or buccal administration is about 0.1% to about 50% of a percentage of a comparative composition effluxed by P-gp following oral administration, wherein the sublingual or buccal and the oral administrations are at the same delivery dose. In some embodiments, a percentage of the composition influxed by an OATP following the sublingual or buccal administration is about 0.1% to about 50% of a percentage of a comparative composition influxed by the OATP following oral administration, wherein the sublingual or buccal and the oral administrations are at the same delivery dose. In some embodiments, a percentage of the composition metabolized by CYP3A4, CYP1A2, or CYP2B6, following the sublingual or buccal administration is about 0.1% to about 50% of a percentage of a comparative composition metabolized by CYP3A4, CYP1A2, or CYP2B6, following oral administration, wherein the sublingual or buccal and the oral administrations are at the same delivery dose. In some embodiments, the composition is administered in a dosage form that disintegrates when placed in the sublingual or buccal cavity. In some embodiments, at least one parameter selected from bioavailability, Cmax, AUC, Tmax, percentage of the composition effluxed by P-gp, percentage of the composition influxed by an OATP, and percentage of the composition metabolized by CYP3A4, CYP1A2, or CYP2B6, is measured following administration of a single dose comprising at least 15 mg of the substituted or unsubstituted diindolylmethane. In some embodiments, the single dose comprising at least 15 mg of the substituted or unsubstituted diindolylmethane is preceded by daily administration of at least 15 mg of the substituted or unsubstituted diindolylmethane for at least 14 days. In some embodiments, the Cmax of the substituted or unsubstituted diindolylmethane in plasma is about 1-fold to about 50-fold higher compared to Cmax of a substituted or unsubstituted diindolylmethane of a comparative composition administered by oral route, wherein the Cmax of the comparative composition is measured following administration of a single dose comprising at least 15 mg of the comparative composition preceded by daily administration of at least 15 mg of the comparative composition for at least 14 days.

Another embodiment provides a method of treating rosacea in a subject in need thereof comprising administering to the subject a composition comprising a substituted or unsubstituted diindolylmethane, wherein the composition is administered by a sublingual or buccal route. In some embodiments, the composition further comprises a substituted or unsubstituted retinoic acid based component. In some embodiments, the retinoic acid based component is Vitamin A. In some embodiments, the composition further comprises a vitamin A palmitate. In some embodiments, the administration by the sublingual or buccal route increases bioavailability of the substituted or unsubstituted diindolylmethane by about 1-fold to about 50-fold compared to bioavailability of a substituted or unsubstituted diindolylmethane of a comparative composition administered by oral route at the same delivery dose. In some embodiments, following administration of the composition by the sublingual or buccal route Cmax of the substituted or unsubstituted diindolylmethane in plasma increases by about 1-fold to about 50-fold compared to Cmax of a substituted or unsubstituted diindolylmethane of a comparative composition administered by oral route at the same delivery dose. In some embodiments, following administration of the composition by the sublingual or buccal route AUC of the substituted or unsubstituted diindolylmethane in plasma increases by about 1-fold to about 50-fold compared to AUC of a substituted or unsubstituted diindolylmethane of a comparative composition administered by oral route at the same delivery dose. In some embodiments, following administration of the composition by the sublingual or buccal route Tmax of the substituted or unsubstituted diindolylmethane in plasma decreases by about 1-fold to about 50-fold compared to the Tmax of a substituted or unsubstituted diindolylmethane of a comparative composition administered by oral route at the same delivery dose. In some embodiments, wherein a percentage of the composition effluxed by P-gp following the sublingual or buccal administration is about 0.1% to about 50% of a percentage of a comparative composition effluxed by P-gp following oral administration, wherein the sublingual or buccal and the oral administrations are at the same delivery dose. In some embodiments, a percentage of the composition influxed by an OATP following the sublingual or buccal administration is about 0.1% to about 50% of a percentage of a comparative composition influxed by an OATP following oral administration, wherein the sublingual or buccal and the oral administrations are at the same delivery dose. In some embodiments, the percentage of the composition metabolized by CYP3A4, CYP1A2, or CYP2B6, following the sublingual or buccal administration is about 0.1% to about 50% of a percentage of a comparative composition metabolized by CYP3A4, CYP1A2, or CYP2B6, following oral administration, wherein the sublingual or buccal and the oral administrations are at the same delivery dose. In some embodiments, the composition is administered in a dosage form that disintegrates when placed in the sublingual or buccal cavity. In some embodiments, at least one parameter selected from bioavailability, Cmax, AUC, Tmax, percentage of the composition effluxed by P-gp, percentage of the composition influxed by an OATP, and percentage of the composition metabolized by CYP3A4, CYP1A2, or CYP2B6, is measured following administration of a single dose comprising at least 15 mg of the substituted or unsubstituted diindolylmethane. In some embodiments, the single dose comprising at least 15 mg of the substituted or unsubstituted diindolylmethane is preceded by daily administration of at least 15 mg of the substituted or unsubstituted diindolylmethane for at least 14 days. In some embodiments, the Cmax of the substituted or unsubstituted diindolylmethane in plasma is about 1-fold to about 50-fold higher compared to Cmax of a substituted or unsubstituted diindolylmethane of a comparative composition administered by oral route, wherein the Cmax of the comparative composition is measured following administration of a single dose comprising at least 15 mg of the comparative compoition preceded by daily administration of at least 15 mg of the comparative composition for at least 14 days.

Provided herein in one embodiment is a method of treating acne in a subject in need thereof comprising administering to the subject a composition comprising substituted or unsubstituted diindolylmethane, wherein the composition is administered by sublingual or buccal route. In some embodiments, the composition further comprises a substituted or unsubstituted retinoic acid based component. In some embodiments, the retinoic acid based component is Vitamin A.

In some embodiments, the administration by sublingual or buccal route increases the bioavailability of the substituted or unsubstituted diindolylmethane by about 1-fold to about 1000-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 1-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 2-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 3-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 4-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 5-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 10-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 20-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 30-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 40-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 50-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 60-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 70-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 80-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 100-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 200-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 300-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 400-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 500-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 600-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 700-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 800-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 900-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 1000-fold compared to the bioavailability of the substituted or unsubstituted diindolylmethane of a comparative composition administered by oral route at the same delivery dose. In some embodiments, the bioavailability of the substituted or unsubstituted diindolylmethane is measured following administration of a dose comprising at least 15 mg of the substituted or unsubstituted diindolylmethane.

In some embodiments, following administration of the composition by sublingual or buccal route the Cmax of the substituted or unsubstituted diindolylmethane in plasma increases by about 1-fold to about 1000-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 2-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 3-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 4-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 5-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 10-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 20-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 30-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 40-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 50-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 60-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 70-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 80-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 90-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 100-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 200-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 300-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 400-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 500-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 600-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 700-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 800-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 900-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 1000-fold compared to the Cmax following administration of a comparative composition by oral route at the same delivery dose. In some embodiments, the Cmax of the substituted or unsubstituted diindolylmethane in plasma is measured following administration of a dose comprising at least 15 mg of the substituted or unsubstituted diindolylmethane.

In some embodiments, following administration of the composition by sublingual or buccal route the AUC of the substituted or unsubstituted diindolylmethane in plasma increases by about 1-fold to about 1000-fold compared to the AUC following administration of a comparative composition by oral route at the same delivery dose. In some embodiments, following administration of the composition by sublingual or buccal route the AUC of the substituted or unsubstituted diindolylmethane in plasma increases by about 2-fold compared to the AUC following administration of a comparative composition by oral route at the same delivery dose. In some embodiments, following administration of the composition by sublingual or buccal route the AUC of the substituted or unsubstituted diindolylmethane in plasma increases by about 3-fold compared to the AUC following administration of a comparative composition by oral route at the same delivery dose. In some embodiments, following administration of the composition by sublingual or buccal route the AUC of the substituted or unsubstituted diindolylmethane in plasma increases by about 4-fold compared to the AUC following administration of a comparative composition by oral route at the same delivery dose. In some embodiments, following administration of the composition by sublingual or buccal route the AUC of the substituted or unsubstituted diindolylmethane in plasma increases by about 5-fold compared to the AUC following administration of a comparative composition by oral route at the same delivery dose. In some embodiments, following administration of the composition by sublingual or buccal route the AUC of the substituted or unsubstituted diindolylmethane in plasma increases by about 6-fold compared to the AUC following administration of a comparative composition by oral route at the same delivery dose. In some embodiments, following administration of the composition by sublingual or buccal route the AUC of the substituted or unsubstituted diindolylmethane in plasma increases by about 7-fold compared to the AUC following administration of a comparative composition by oral route at the same delivery dose. In some embodiments, following administration of the composition by sublingual or buccal route the AUC of the substituted or unsubstituted diindolylmethane in plasma increases by about 8-fold compared to the AUC following administration of a comparative composition by oral route at the same delivery dose. In some embodiments, following administration of the composition by sublingual or buccal route the AUC of the substituted or unsubstituted diindolylmethane in plasma increases by about 9-fold compared to the AUC following administration of a comparative composition by oral route at the same delivery dose. In some embodiments, following administration of the composition by sublingual or buccal route the AUC of the substituted or unsubstituted diindolylmethane in plasma increases by about 10-fold compared to the AUC following administration of a comparative composition by oral route at the same delivery dose. In some embodiments, following administration of the composition by sublingual or buccal route the AUC of the substituted or unsubstituted diindolylmethane in plasma increases by about 20-fold compared to the AUC following administration of a comparative composition by oral route at the same delivery dose. In some embodiments, following administration of the composition by sublingual or buccal route the AUC of the substituted or unsubstituted diindolylmethane in plasma increases by about 30-fold compared to the AUC following administration of a comparative composition by oral route at the same delivery dose. In some embodiments, following administration of the composition by sublingual or buccal route the AUC of the substituted or unsubstituted diindolylmethane in plasma increases by about 40-fold compared to the AUC following administration of a comparative composition by oral route at the same delivery dose. In some embodiments, following administration of the composition by sublingual or buccal route the AUC of the substituted or unsubstituted diindolylmethane in plasma increases by about 50-fold compared to the AUC following administration of a comparative composition by oral route at the same delivery dose. In some embodiments, following administration of the composition by sublingual or buccal route the AUC of the substituted or unsubstituted diindolylmethane in plasma increases by about 60-fold compared to the AUC following administration of a comparative composition by oral route at the same delivery dose. In some embodiments, following administration of the composition by sublingual or buccal route the AUC of the substituted or unsubstituted diindolylmethane in plasma increases by about 70-fold compared to the AUC following administration of a comparative composition by oral route at the same delivery dose. In some embodiments, following administration of the composition by sublingual or buccal route the AUC of the substituted or unsubstituted diindolylmethane in plasma increases by about 80-fold compared to the AUC following administration of a comparative composition by oral route at the same delivery dose. In some embodiments, following administration of the composition by sublingual or buccal route the AUC of the substituted or unsubstituted diindolylmethane in plasma increases by about 90-fold compared to the AUC following administration of a comparative composition by oral route at the same delivery dose. In some embodiments, following administration of the composition by sublingual or buccal route the AUC of the substituted or unsubstituted diindolylmethane in plasma increases by about 100-fold compared to the AUC following administration of a comparative composition by oral route at the same delivery dose. In some embodiments, following administration of the composition by sublingual or buccal route the AUC of the substituted or unsubstituted diindolylmethane in plasma increases by about 200-fold compared to the AUC following administration of a comparative composition by oral route at the same delivery dose. In some embodiments, following administration of the composition by sublingual or buccal route the AUC of the substituted or unsubstituted diindolylmethane in plasma increases by about 300-fold compared to the AUC following administration of a comparative composition by oral route at the same delivery dose. In some embodiments, following administration of the composition by sublingual or buccal route the AUC of the substituted or unsubstituted diindolylmethane in plasma increases by about 400-fold compared to the AUC following administration of a comparative composition by oral route at the same delivery dose. In some embodiments, following administration of the composition by sublingual or buccal route the AUC of the substituted or unsubstituted diindolylmethane in plasma increases by about 500-fold compared to the AUC following administration of a comparative composition by oral route at the same delivery dose. In some embodiments, following administration of the composition by sublingual or buccal route the AUC of the substituted or unsubstituted diindolylmethane in plasma increases by about 600-fold compared to the AUC following administration of a comparative composition by oral route at the same delivery dose. In some embodiments, following administration of the composition by sublingual or buccal route the AUC of the substituted or unsubstituted diindolylmethane in plasma increases by about 700-fold compared to the AUC following administration of a comparative composition by oral route at the same delivery dose. In some embodiments, following administration of the composition by sublingual or buccal route the AUC of the substituted or unsubstituted diindolylmethane in plasma increases by about 800-fold compared to the AUC following administration of a comparative composition by oral route at the same delivery dose. In some embodiments, following administration of the composition by sublingual or buccal route the AUC of the substituted or unsubstituted diindolylmethane in plasma increases by about 900-fold compared to the AUC following administration of a comparative composition by oral route at the same delivery dose. In some embodiments, following administration of the composition by sublingual or buccal route the AUC of the substituted or unsubstituted diindolylmethane in plasma increases by about 1000-fold compared to the AUC following administration of a comparative composition by oral route at the same delivery dose. In some embodiments, the AUC of the substituted or unsubstituted diindolylmethane in plasma is measured following administration of a dose comprising at least 15 mg of the substituted or unsubstituted diindolylmethane.

In some embodiments, following administration of the composition by sublingual or buccal route the Tmax of the substituted or unsubstituted diindolylmethane in plasma decreases by about 1-fold to about 1000-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 1-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 2-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 3-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 4-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 5-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 10-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 20-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 30-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 40-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 50-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 60-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 70-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 80-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 90-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 100-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 200-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 300-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 400-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 500-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 600-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 700-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 800-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 900-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 1000-fold compared to the Tmax following administration of a comparative composition by oral route at the same delivery dose. In some embodiments, the Tmax of the substituted or unsubstituted diindolylmethane in plasma is measured following administration of a dose comprising at least 15 mg of the substituted or unsubstituted diindolylmethane.

In some embodiments, the percentage of a composition effluxed by P-gp following the sublingual or buccal administration is about 0.1% to about 50% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 0.1% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 0.2% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 0.3% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 0.4% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 0.5% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 1% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 2% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 3% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 4% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 5% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 6% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 7% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 8% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 9% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 10% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 20% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 30% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 40% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 50% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration and the percentage of a comparative composition effluxed by P-gp following the oral administration are based on a dosage of administration comprising at least 15 mg of the substituted or unsubstituted diindolylmethane. In some embodiments, the percentage of a composition influxed by an OATP following the sublingual or buccal administration is about 0.1% to about 50% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 0.1% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 0.2% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 0.3% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 0.4% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 0.5% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 0.6% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 0.7% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 0.8% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 0.9% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 1% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 2% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 3% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 4% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 5% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 6% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 7% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 8% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 9% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 10% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 20% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 30% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 40% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 50% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration and the percentage of a comparative composition influxed by an OATP following the oral administration are based on a dosage of administration comprising at least 15 mg of the substituted or unsubstituted diindolylmethane. In some embodiments, the percentage of a composition metabolized by CYP3A4, CYP1A2, or CYP2B6, following the sublingual or buccal administration is about 0.1% to about 50% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 0.1% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 0.2% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 0.3% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 0.4% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 0.5% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 0.6% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 0.7% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 0.8% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 0.9% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 1% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 2% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 3% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 4% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 5% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 6% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 7% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 8% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 9% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 10% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 20% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 30% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 40% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 50% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration and the percentage of a comparative composition metabolized by CYP3A4, CYP1A2, or CYP2B6, following the oral administration are based on a dosage of administration comprising at least 15 mg of the substituted or unsubstituted diindolylmethane. In some embodiments, the composition is administered in a dosage form that disintegrates when placed in the sublingual or buccal cavity.

Provided herein in one embodiment is a method of treating rosacea in a subject in need thereof comprising administering to the subject a composition comprising substituted or unsubstituted diindolylmethane, wherein the composition is administered by sublingual or buccal route. In some embodiments, the composition further comprises a substituted or unsubstituted retinoic acid based component. In some embodiments, the retinoic acid based component is Vitamin A.

In some embodiments, the administration by sublingual or buccal route increases the bioavailability of the substituted or unsubstituted diindolylmethane by about 1-fold to about 1000-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 1-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 2-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 3-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 4-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 5-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 10-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 20-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 30-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 40-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 50-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 60-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 70-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 80-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 100-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 200-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 300-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 400-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 500-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 600-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 700-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 800-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 900-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 1000-fold compared to the bioavailability of the substituted or unsubstituted diindolylmethane of a comparative composition administered by oral route at the same delivery dose. In some embodiments, the bioavailability of the substituted or unsubstituted diindolylmethane is measured following administration of a dose comprising at least 15 mg of the substituted or unsubstituted diindolylmethane.

In some embodiments, following administration of the composition by sublingual or buccal route the Cmax of the substituted or unsubstituted diindolylmethane in plasma increases by about 1-fold to about 1000-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 2-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 3-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 4-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 5-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 10-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 20-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 30-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 40-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 50-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 60-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 70-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 80-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 90-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 100-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 200-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 300-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 400-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 500-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 600-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 700-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 800-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 900-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 1000-fold compared to the Cmax following administration of a comparative composition by oral route at the same delivery dose. In some embodiments, the Cmax of the substituted or unsubstituted diindolylmethane in plasma is measured following administration of a dose comprising at least 15 mg of the substituted or unsubstituted diindolylmethane.

In some embodiments, following administration of the composition by sublingual or buccal route the AUC of the substituted or unsubstituted diindolylmethane in plasma increases by about 1-fold to about 1000-fold compared to the AUC following administration of a comparative composition by oral route at the same delivery dose. In some embodiments, following administration of the composition by sublingual or buccal route the AUC of the substituted or unsubstituted diindolylmethane in plasma increases by about 2-fold compared to the AUC following administration of a comparative composition by oral route at the same delivery dose. In some embodiments, following administration of the composition by sublingual or buccal route the AUC of the substituted or unsubstituted diindolylmethane in plasma increases by about 3-fold compared to the AUC following administration of a comparative composition by oral route at the same delivery dose. In some embodiments, following administration of the composition by sublingual or buccal route the AUC of the substituted or unsubstituted diindolylmethane in plasma increases by about 4-fold compared to the AUC following administration of a comparative composition by oral route at the same delivery dose. In some embodiments, following administration of the composition by sublingual or buccal route the AUC of the substituted or unsubstituted diindolylmethane in plasma increases by about 5-fold compared to the AUC following administration of a comparative composition by oral route at the same delivery dose. In some embodiments, following administration of the composition by sublingual or buccal route the AUC of the substituted or unsubstituted diindolylmethane in plasma increases by about 6-fold compared to the AUC following administration of a comparative composition by oral route at the same delivery dose. In some embodiments, following administration of the composition by sublingual or buccal route the AUC of the substituted or unsubstituted diindolylmethane in plasma increases by about 7-fold compared to the AUC following administration of a comparative composition by oral route at the same delivery dose. In some embodiments, following administration of the composition by sublingual or buccal route the AUC of the substituted or unsubstituted diindolylmethane in plasma increases by about 8-fold compared to the AUC following administration of a comparative composition by oral route at the same delivery dose. In some embodiments, following administration of the composition by sublingual or buccal route the AUC of the substituted or unsubstituted diindolylmethane in plasma increases by about 9-fold compared to the AUC following administration of a comparative composition by oral route at the same delivery dose. In some embodiments, following administration of the composition by sublingual or buccal route the AUC of the substituted or unsubstituted diindolylmethane in plasma increases by about 10-fold compared to the AUC following administration of a comparative composition by oral route at the same delivery dose. In some embodiments, following administration of the composition by sublingual or buccal route the AUC of the substituted or unsubstituted diindolylmethane in plasma increases by about 20-fold compared to the AUC following administration of a comparative composition by oral route at the same delivery dose. In some embodiments, following administration of the composition by sublingual or buccal route the AUC of the substituted or unsubstituted diindolylmethane in plasma increases by about 30-fold compared to the AUC following administration of a comparative composition by oral route at the same delivery dose. In some embodiments, following administration of the composition by sublingual or buccal route the AUC of the substituted or unsubstituted diindolylmethane in plasma increases by about 40-fold compared to the AUC following administration of a comparative composition by oral route at the same delivery dose. In some embodiments, following administration of the composition by sublingual or buccal route the AUC of the substituted or unsubstituted diindolylmethane in plasma increases by about 50-fold compared to the AUC following administration of a comparative composition by oral route at the same delivery dose. In some embodiments, following administration of the composition by sublingual or buccal route the AUC of the substituted or unsubstituted diindolylmethane in plasma increases by about 60-fold compared to the AUC following administration of a comparative composition by oral route at the same delivery dose. In some embodiments, following administration of the composition by sublingual or buccal route the AUC of the substituted or unsubstituted diindolylmethane in plasma increases by about 70-fold compared to the AUC following administration of a comparative composition by oral route at the same delivery dose. In some embodiments, following administration of the composition by sublingual or buccal route the AUC of the substituted or unsubstituted diindolylmethane in plasma increases by about 80-fold compared to the AUC following administration of a comparative composition by oral route at the same delivery dose. In some embodiments, following administration of the composition by sublingual or buccal route the AUC of the substituted or unsubstituted diindolylmethane in plasma increases by about 90-fold compared to the AUC following administration of a comparative composition by oral route at the same delivery dose. In some embodiments, following administration of the composition by sublingual or buccal route the AUC of the substituted or unsubstituted diindolylmethane in plasma increases by about 100-fold compared to the AUC following administration of a comparative composition by oral route at the same delivery dose. In some embodiments, following administration of the composition by sublingual or buccal route the AUC of the substituted or unsubstituted diindolylmethane in plasma increases by about 200-fold compared to the AUC following administration of a comparative composition by oral route at the same delivery dose. In some embodiments, following administration of the composition by sublingual or buccal route the AUC of the substituted or unsubstituted diindolylmethane in plasma increases by about 300-fold compared to the AUC following administration of a comparative composition by oral route at the same delivery dose. In some embodiments, following administration of the composition by sublingual or buccal route the AUC of the substituted or unsubstituted diindolylmethane in plasma increases by about 400-fold compared to the AUC following administration of a comparative composition by oral route at the same delivery dose. In some embodiments, following administration of the composition by sublingual or buccal route the AUC of the substituted or unsubstituted diindolylmethane in plasma increases by about 500-fold compared to the AUC following administration of a comparative composition by oral route at the same delivery dose. In some embodiments, following administration of the composition by sublingual or buccal route the AUC of the substituted or unsubstituted diindolylmethane in plasma increases by about 600-fold compared to the AUC following administration of a comparative composition by oral route at the same delivery dose. In some embodiments, following administration of the composition by sublingual or buccal route the AUC of the substituted or unsubstituted diindolylmethane in plasma increases by about 700-fold compared to the AUC following administration of a comparative composition by oral route at the same delivery dose. In some embodiments, following administration of the composition by sublingual or buccal route the AUC of the substituted or unsubstituted diindolylmethane in plasma increases by about 800-fold compared to the AUC following administration of a comparative composition by oral route at the same delivery dose. In some embodiments, following administration of the composition by sublingual or buccal route the AUC of the substituted or unsubstituted diindolylmethane in plasma increases by about 900-fold compared to the AUC following administration of a comparative composition by oral route at the same delivery dose. In some embodiments, following administration of the composition by sublingual or buccal route the AUC of the substituted or unsubstituted diindolylmethane in plasma increases by about 1000-fold compared to the AUC following administration of a comparative composition by oral route at the same delivery dose. In some embodiments, the AUC of the substituted or unsubstituted diindolylmethane in plasma is measured following administration of a dose comprising at least 15 mg of the substituted or unsubstituted diindolylmethane.

In some embodiments, following administration of the composition by sublingual or buccal route the Tmax of the substituted or unsubstituted diindolylmethane in plasma decreases by about 1-fold to about 1000-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 1-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 2-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 3-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 4-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 5-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 10-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 20-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 30-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 40-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 50-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 60-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 70-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 80-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 90-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 100-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 200-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 300-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 400-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 500-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 600-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 700-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 800-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 900-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 1000-fold compared to the Tmax following administration of a comparative composition by oral route at the same delivery dose. In some embodiments, the Tmax of the substituted or unsubstituted diindolylmethane in plasma is measured following administration of a dose comprising at least 15 mg of the substituted or unsubstituted diindolylmethane. In some embodiments, the percentage of a composition effluxed by P-gp following the sublingual or buccal administration is about 0.1% to about 50% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 0.1% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 0.2% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 0.3% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 0.4% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 0.5% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 1% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 2% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 3% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 4% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 5% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 6% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 7% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 8% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 9% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 10% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 20% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 30% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 40% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration is about 50% of the percentage of a comparative composition effluxed by P-gp following the oral administration, wherein the sublingual or buccal and oral administrations are at the same delivery dose. In some embodiments, the percentage of a composition effluxed by P-gp following the sublingual or buccal administration and the percentage of a comparative composition effluxed by P-gp following the oral administration are based on a dosage of administration comprising at least 15 mg of the substituted or unsubstituted diindolylmethane.

In some embodiments, the percentage of a composition influxed by an OATP following the sublingual or buccal administration is about 0.1% to about 50% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 0.1% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 0.2% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 0.3% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 0.4% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 0.5% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 0.6% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 0.7% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 0.8% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 0.9% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 1% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 2% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 3% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 4% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 5% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 6% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 7% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 8% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 9% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 10% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 20% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 30% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 40% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration is about 50% of the percentage of a comparative composition influxed by an OATP following the oral administration, wherein the sublingual or buccal and oral administrations are at the same delivery dose. In some embodiments, the percentage of a composition influxed by an OATP following the sublingual or buccal administration and the percentage of a comparative composition influxed by an OATP following the oral administration are based on a dosage of administration comprising at least 15 mg of the substituted or unsubstituted diindolylmethane.

In some embodiments, the percentage of a composition metabolized by CYP3A4, CYP1A2, or CYP2B6, following the sublingual or buccal administration is about 0.1% to about 50% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 0.1% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 0.2% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 0.3% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 0.4% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 0.5% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 0.6% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 0.7% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 0.8% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 0.9% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 1% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 2% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 3% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 4% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 5% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 6% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 7% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 8% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 9% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 10% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 20% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 30% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 40% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration is about 50% of the percentage of a comparative composition metabolized by CYP3A4, CYP1A2, or CYP2B6, following the oral administration, wherein the sublingual or buccal and oral administrations are at the same delivery dose. In some embodiments, the percentage of a composition metabolized by CYP3A4, CYP1A2, or CYP2B6, following the sublingual or buccal administration and the percentage of a comparative composition metabolized by CYP3A4, CYP1A2, or CYP2B6, following the oral administration are based on a dosage of administration comprising at least 15 mg of the substituted or unsubstituted diindolylmethane. In some embodiments, the composition is administered in a dosage form that disintegrates when placed in the sublingual or buccal cavity.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE DISCLOSURE

Figure 1:
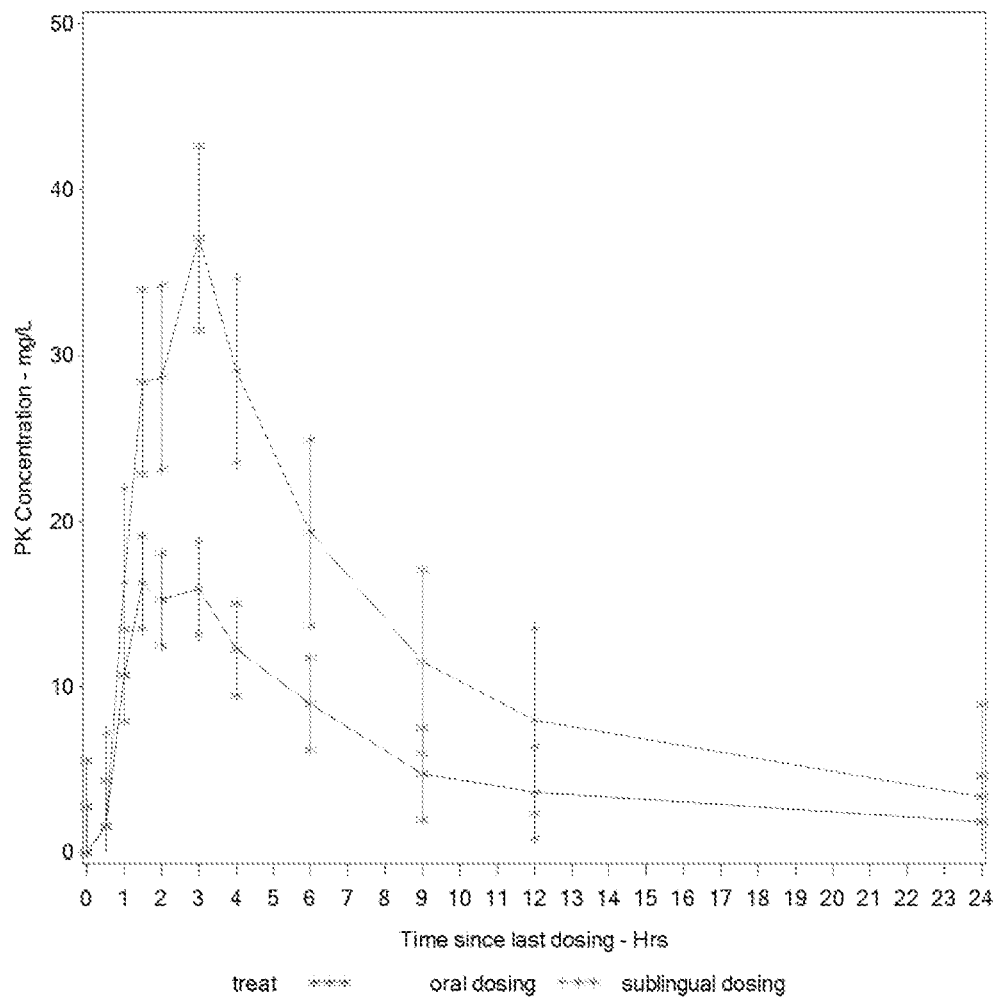
FIG. 1 illustrates plasma concentration of DIM following oral or sublingual administration of a DIM formulation. The top line, in light gray, shows the plasma concentration after sublingual administration and the bottom line, in dark gray, shows the same after oral administration.

While preferred embodiments of the present disclosure have been shown and described herein, it will be obvious to those skilled in the art that such embodiments are provided by way of example only. Numerous variations, changes, and substitutions will now occur to those skilled in the art without departing from the present disclosure. It should be understood that various alternatives to the embodiments of the present disclosure described herein may be employed. It is intended that the following claims define the scope of the present disclosure and that methods and structures within the scope of these claims and their equivalents be covered thereby.

Unless defined otherwise, all technical and scientific terms used herein have the same meaning as commonly understood by one of skill in the art to which the present disclosure described herein belong. All publications, patents, and patent applications mentioned in this specification are hereby incorporated by reference to the same extent as if each individual publication, patent, or patent application was specifically and individually indicated to be incorporated by reference.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

DIM

Diindolylmethane (DIM) is a natural compound formed during the autolytic breakdown of glucobrassicin present in food plants of the *Brassica* genus, including broccoli, cabbage, Brussels sprouts, cauliflower and kale. The autolytic breakdown of glucobrassicin requires the catalytic reaction of the enzyme myrosinase, which is endogenous to these plants and released upon rupture of the cell wall. The compound is normally manufactured by chemical synthesis but in some embodiments is also prepared by natural means from the extracts of Brassica vegetables, as listed above, particularly from sprouting broccoli or from broccoli seeds.

Thus, the substituted or unsubstituted DIM in some embodiments is synthetic, or in some embodiments is a natural product obtained from a Brassica plant, as discussed above.

Acne

Acne is a chronic inflammatory disease of the pilosebaceous unit resulting from androgen-induced increased sebum production, altered keratinisation, inflammation, and bacterial colonisation of hair follicles on the face, neck, chest, and back by Propionibacterium acnes. The initial pathology of acne is the comedo and includes acne vulgaris, neonatal acne, infantile acne, and pomade acne. The disease of acne is characterized by a great variety of clinical lesions. Although one type of lesion may be predominant (typically the comedo), close observation usually reveals the presence of several types of lesions (comedones, pustules, papules, and/or nodules). The lesions can be either noninflammatory or, more typically, inflammatory. In addition to lesions, patients may have, as the result of lesions, scars of varying size. The fully developed, open comedo (i.e., a plug of dried sebum in a skin pore) is not usually the site of inflammatory changes, unless it is traumatized by the patient. The developing microcomedo and the closed comedo are the major sites for the development of inflammatory lesions. Because the skin is always trying to repair itself, sheaths of cells will grow out from the epidermis (forming appendageal structures) in an attempt to encapsulate the inflammatory reaction. This encapsulation is often incomplete and further rupture of the lesion typically occurs, leading to multichanneled tracts as can be seen in many acne scars.

There are primarily four factors that are believed to be the contributors of acne: (1) Increased sebum production; (2) Comedo formation, in which the follicular infundibulum hypercornifies, hyperkeratinizes, and hypodesquamates; (3) Colonization of the follicle by anaerobic Propionibacterium, mainly P. acnes; and (4) The host's inflammatory response. These four factors are interrelated to each other. Sebum is comedogenic and causes inflammation by itself. The Propionibacterium has high lipolytic activity and liberates free fatty acids from sebum lipids. The free fatty acids have been shown to cause marked inflammation. The microorganisms also produce other extracellular enzymes such as proteases and hyaluronidases, and chemotactic factors, which may be important in the inflammatory process. Other factors such as diet have been implicated, but not proven. Facial scarring due to acne affects up to 20% of teenagers. Acne can persist into adulthood, with detrimental effects on self-esteem. The disease is so common in youth at their puberty that it often has been termed physiological. Although acne stops appearing for most people by the age of 25, some people, the majority of them are women, experience the disease well into their adult life. This "adult acne" differs from teenage acne in location and that it tends to be more inflammatory with fewer comedones.

In general, there are four major principles presently governing the therapy of acne: (i) correction of the altered pattern of follicular keratinization; (ii) decrease sebaceous gland activity; (iii) decrease the follicular bacterial population (especially P. acnes) and inhibit the production of extra cellular inflammatory products through the inhibition of these microorganisms; and (iv) produce an anti-inflammatory effect.

Rosacea

Rosacea is a chronic inflammatory condition of the facial skin affecting the blood vessels and pilosebaceous units. Rosacea is more common in persons of northern and western European descent with a fair complexion, but it can affect skin of any color. Although symptoms may wax and wane during the short term, rosacea can progress with time. Patients usually present with complaints of flushing and blushing and sensitive skin, and their skin may be especially irritated by topical preparations. Rosacea has a variety of triggers; however, they may be unnoticed by the patient.

It is a chronic and progressive cutaneous vascular disorder, primarily involving the malar and nasal areas of the face. Rosacea is characterized by flushing, erythema, papules, pustules, telanglectasia, facial edema, ocular lesions, and, in its most advanced and severe form, hyperplasia of tissue and sebaceous glands leading to rhinophyma. Rhinophyma, a florid overgrowth of the tip of the nose with hypervascularity and modularity, is an unusual progression of rosacea of unknown cause. Ocular lesions are common, including mild conjunctivitis, burning, and grittiness. Blepharitis, the most common ocular manifestation, is a nonulcerative condition of the lidmargins. Rosacea most commonly occurs between the ages of 30 to 60, and may be seen in women experiencing hormonal changes associated with menopause. Women are more frequently affected than men; the most severe cases, however, are seen in men.

Methods of Treating Acne or Rosacea by Sublingual or Buccal Administration of DIM Provided herein in some embodiments are methods of treating acne or rosacea in a subject in need thereof comprising administering to the subject a composition comprising substituted or unsubstituted diindolylmethane, wherein the composition is administered by sublingual or buccal route. In some embodiments, the composition comprising substituted or unsubstituted diindolylmethane further comprises substituted or unsubstituted retinoic acid based component.

In some embodiments, sublingual or buccal delivery allows the substituted or unsubstituted diindolylmethane to dissolve in the immediate vicinity where the product is placed and then the drug enters directly into the blood stream, thereby increasing the bioavailability of the substituted or unsubstituted diindolylmethane and exert its pharmacological effect rapidly.

In some embodiments, the increase in bioavailability of substituted or unsubstituted diindolylmethane upon delivery by sublingual or buccal route is relative to the bioavailability upon administration by oral route, at the same delivery dose, of the same composition. In some embodiments, the increase in bioavailability of substituted or unsubstituted diindolylmethane upon delivery by sublingual or buccal route is relative to the bioavailability upon administration by oral route, at the same delivery dose, of a comparative composition.

In some embodiments, administration of a composition comprising substituted or unsubstituted diindolylmethane by sublingual or buccal route helps by-pass the gastric juices, acid environment and enzymes present in the gastrointestinal tract. In some embodiments, increased bioavailability of the substituted or unsubstituted diindolylmethane by sublingual or buccal administration is attributed to by-passing the gastric juices, acid environment and enzymes present in the gastrointestinal tract. In some embodiments, the administration of substituted or unsubstituted diindolylmethane by sublingual or buccal route helps by-pass the liver which is the target organ for metabolism of the drug when administered orally. In some embodiments, increased bioavailability of the substituted or unsubstituted diindolylmethane by sublingual or buccal administration is attributed to by-passing first pass metabolism by the liver. In some embodiments, the highly vascular mucosal lining between the cheek and gum where buccal formulations are placed or under the tongue where sublingual formulations are placed are ideal and convenient locations for the substituted or unsubstituted diindolylmethane to be absorbed.

Increase in Bioavailability of DIM by Sublingual or Buccal Administration

In some embodiments, the administration by sublingual or buccal route increases the bioavailability of the substituted or unsubstituted diindolylmethane by about 1-fold to about 1000-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 1-fold to about 500-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 1-fold to about 100-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 1-fold to about 50-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 1-fold to about 20-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 1-fold to about 10-fold compared to the bioavailability of the substituted or unsubstituted diindolylmethane of a comparative composition administered by oral route at the same delivery dose.

In some embodiments, the administration by sublingual or buccal route increases the bioavailability of the substituted or unsubstituted diindolylmethane by about 1-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 2-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 3-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 4-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 5-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 10-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 20-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 30-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 40-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 50-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 60-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 70-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 80-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 100-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 200-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 300-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 400-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 500-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 600-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 700-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 800-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 900-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 1000-fold compared to the bioavailability of the substituted or unsubstituted diindolylmethane of a comparative composition administered by oral route at the same delivery dose. In some embodiments, the administration by sublingual or buccal route increases the bioavailability of the substituted or unsubstituted diindolylmethane by about 100-fold compared to the bioavailability of the substituted or unsubstituted diindolylmethane of a comparative composition administered by oral route at the same delivery dose.

Improved Pharmacokinetic Parameters Upon Administration of DIM by Sublingual or Buccal Route Bioavailability includes the following exemplary pharmacokinetic factors: rate (or time after administration) of achievement of minimum effective drug serum concentration (MEC), maximum drug serum concentration (Cmax), rate (or time after administration) of achievement of maximum drug serum concentration (Tmax), and the area under the drug serum concentration-time curve above a line representing minimum effective drug serum concentration (AUC). In some embodiments, the methods of treating acne or rosacea by administration of substituted or unsubstituted diindolylmethane by sublingual or buccal route, as described herein, leads to enhancement in one more of the factors mentioned above.

Increased Cmax

In some embodiments, following administration of the composition by sublingual or buccal route the Cmax of the substituted or unsubstituted diindolylmethane in plasma increases by about 1-fold to about 1000-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 1-fold to about 500-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 1-fold to about 100-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 1-fold to about 50-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 1-fold to about 20-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 1-fold to about 10-fold compared to the Cmax following administration of a comparative composition by oral route at the same delivery dose.

In some embodiments, following administration of the composition by sublingual or buccal route the Cmax of the substituted or unsubstituted diindolylmethane in plasma increases by about 1-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 2-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 3-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 4-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 5-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 6-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 7-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 8-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 9-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 10-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 20-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 30-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 40-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 50-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 60-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 70-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 80-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 90-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 100-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 200-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 300-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 400-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 500-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 600-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 700-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 800-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 800-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 900-fold compared to the Cmax following administration of a comparative composition by oral route at the same delivery dose. In some embodiments, following administration of the composition by sublingual or buccal route the Cmax of the substituted or unsubstituted diindolylmethane in plasma increases by about 1000-fold compared to the Cmax following administration of a comparative composition by oral route at the same delivery dose.

Increased AUC

In some embodiments, following administration of the composition by sublingual or buccal route the AUC of the substituted or unsubstituted diindolylmethane in plasma increases by about 1-fold to about 1000-fold compared to the AUC following administration of a comparative composition by oral route at the same delivery dose. In some embodiments, following administration of the composition by sublingual or buccal route the AUC of the substituted or unsubstituted diindolylmethane in plasma increases by about 1-fold to about 500-fold compared to the AUC following administration of a comparative composition by oral route at the same delivery dose. In some embodiments, following administration of the composition by sublingual or buccal route the AUC of the substituted or unsubstituted diindolylmethane in plasma increases by about 1-fold to about 100-fold compared to the AUC following administration of a comparative composition by oral route at the same delivery dose. In some embodiments, following administration of the composition by sublingual or buccal route the AUC of the substituted or unsubstituted diindolylmethane in plasma increases by about 1-fold to about 50-fold compared to the AUC following administration of a comparative composition by oral route at the same delivery dose. In some embodiments, following administration of the composition by sublingual or buccal route the AUC of the substituted or unsubstituted diindolylmethane in plasma increases by about 1-fold to about 20-fold compared to the AUC following administration of a comparative composition by oral route at the same delivery dose. In some embodiments, following administration of the composition by sublingual or buccal route the AUC of the substituted or unsubstituted diindolylmethane in plasma increases by about 1-fold to about 10-fold compared to the AUC following administration of a comparative composition by oral route at the same delivery dose.

In some embodiments, following administration of the composition by sublingual or buccal route the AUC of the substituted or unsubstituted diindolylmethane in plasma increases by about 1-fold compared to the AUC following administration of a comparative composition by oral route at the same delivery dose. In some embodiments, following administration of the composition by sublingual or buccal route the AUC of the substituted or unsubstituted diindolylmethane in plasma increases by about 2-fold compared to the AUC following administration of a comparative composition by oral route at the same delivery dose. In some embodiments, following administration of the composition by sublingual or buccal route the AUC of the substituted or unsubstituted diindolylmethane in plasma increases by about 3-fold compared to the AUC following administration of a comparative composition by oral route at the same delivery dose. In some embodiments, following administration of the composition by sublingual or buccal route the AUC of the substituted or unsubstituted diindolylmethane in plasma increases by about 4-fold compared to the AUC following administration of a comparative composition by oral route at the same delivery dose. In some embodiments, following administration of the composition by sublingual or buccal route the AUC of the substituted or unsubstituted diindolylmethane in plasma increases by about 5-fold compared to the AUC following administration of a comparative composition by oral route at the same delivery dose. In some embodiments, following administration of the composition by sublingual or buccal route the AUC of the substituted or unsubstituted diindolylmethane in plasma increases by about 6-fold compared to the AUC following administration of a comparative composition by oral route at the same delivery dose. In some embodiments, following administration of the composition by sublingual or buccal route the AUC of the substituted or unsubstituted diindolylmethane in plasma increases by about 7-fold compared to the AUC following administration of a comparative composition by oral route at the same delivery dose. In some embodiments, following administration of the composition by sublingual or buccal route the AUC of the substituted or unsubstituted diindolylmethane in plasma increases by about 8-fold compared to the AUC following administration of a comparative composition by oral route at the same delivery dose. In some embodiments, following administration of the composition by sublingual or buccal route the AUC of the substituted or unsubstituted diindolylmethane in plasma increases by about 9-fold compared to the AUC following administration of a comparative composition by oral route at the same delivery dose. In some embodiments, following administration of the composition by sublingual or buccal route the AUC of the substituted or unsubstituted diindolylmethane in plasma increases by about 10-fold compared to the AUC following administration of a comparative composition by oral route at the same delivery dose. In some embodiments, following administration of the composition by sublingual or buccal route the AUC of the substituted or unsubstituted diindolylmethane in plasma increases by about 20-fold compared to the AUC following administration of a comparative composition by oral route at the same delivery dose. In some embodiments, following administration of the composition by sublingual or buccal route the AUC of the substituted or unsubstituted diindolylmethane in plasma increases by about 30-fold compared to the AUC following administration of a comparative composition by oral route at the same delivery dose. In some embodiments, following administration of the composition by sublingual or buccal route the AUC of the substituted or unsubstituted diindolylmethane in plasma increases by about 40-fold compared to the AUC following administration of a comparative composition by oral route at the same delivery dose. In some embodiments, following administration of the composition by sublingual or buccal route the AUC of the substituted or unsubstituted diindolylmethane in plasma increases by about 50-fold compared to the AUC following administration of a comparative composition by oral route at the same delivery dose. In some embodiments, following administration of the composition by sublingual or buccal route the AUC of the substituted or unsubstituted diindolylmethane in plasma increases by about 60-fold compared to the AUC following administration of a comparative composition by oral route at the same delivery dose. In some embodiments, following administration of the composition by sublingual or buccal route the AUC of the substituted or unsubstituted diindolylmethane in plasma increases by about 70-fold compared to the AUC following administration of a comparative composition by oral route at the same delivery dose. In some embodiments, following administration of the composition by sublingual or buccal route the AUC of the substituted or unsubstituted diindolylmethane in plasma increases by about 80-fold compared to the AUC following administration of a comparative composition by oral route at the same delivery dose. In some embodiments, following administration of the composition by sublingual or buccal route the AUC of the substituted or unsubstituted diindolylmethane in plasma increases by about 90-fold compared to the AUC following administration of a comparative composition by oral route at the same delivery dose. In some embodiments, following administration of the composition by sublingual or buccal route the AUC of the substituted or unsubstituted diindolylmethane in plasma increases by about 100-fold compared to the AUC following administration of a comparative composition by oral route at the same delivery dose. In some embodiments, following administration of the composition by sublingual or buccal route the AUC of the substituted or unsubstituted diindolylmethane in plasma increases by about 200-fold compared to the AUC following administration of a comparative composition by oral route at the same delivery dose. In some embodiments, following administration of the composition by sublingual or buccal route the AUC of the substituted or unsubstituted diindolylmethane in plasma increases by about 300-fold compared to the AUC following administration of a comparative composition by oral route at the same delivery dose. In some embodiments, following administration of the composition by sublingual or buccal route the AUC of the substituted or unsubstituted diindolylmethane in plasma increases by about 400-fold compared to the AUC following administration of a comparative composition by oral route at the same delivery dose. In some embodiments, following administration of the composition by sublingual or buccal route the AUC of the substituted or unsubstituted diindolylmethane in plasma increases by about 500-fold compared to the AUC following administration of a comparative composition by oral route at the same delivery dose. In some embodiments, following administration of the composition by sublingual or buccal route the AUC of the substituted or unsubstituted diindolylmethane in plasma increases by about 600-fold compared to the AUC following administration of a comparative composition by oral route at the same delivery dose. In some embodiments, following administration of the composition by sublingual or buccal route the AUC of the substituted or unsubstituted diindolylmethane in plasma increases by about 700-fold compared to the AUC following administration of a comparative composition by oral route at the same delivery dose. In some embodiments, following administration of the composition by sublingual or buccal route the AUC of the substituted or unsubstituted diindolylmethane in plasma increases by about 800-fold compared to the AUC following administration of a comparative composition by oral route at the same delivery dose. In some embodiments, following administration of the composition by sublingual or buccal route the AUC of the substituted or unsubstituted diindolylmethane in plasma increases by about 800-fold compared to the AUC following administration of a comparative composition by oral route at the same delivery dose. In some embodiments, following administration of the composition by sublingual or buccal route the AUC of the substituted or unsubstituted diindolylmethane in plasma increases by about 900-fold compared to the AUC following administration of a comparative composition by oral route at the same delivery dose. In some embodiments, following administration of the composition by sublingual or buccal route the AUC of the substituted or unsubstituted diindolylmethane in plasma increases by about 1000-fold compared to the AUC following administration of a comparative composition by oral route at the same delivery dose.

Decreased Tmax

In some embodiments, following administration of the composition by sublingual or buccal route the Tmax of the substituted or unsubstituted diindolylmethane in plasma decreases by about 1-fold to about 1000-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 1-fold to about 500-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 1-fold to about 100-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 1-fold to about 50-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 1-fold to about 20-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 1-fold to about 10-fold compared to the Tmax following administration of a comparative composition by oral route at the same delivery dose.

In some embodiments, following administration of the composition by sublingual or buccal route the Tmax of the substituted or unsubstituted diindolylmethane in plasma decreases by about 1-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 2-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 3-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 4-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 5-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 6-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 7-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 8-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 9-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 10-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 20-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 30-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 40-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 50-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 60-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 70-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 80-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 100-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 200-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 300-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 400-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 500-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 600-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 700-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 800-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 900-fold compared to the Tmax following administration of a comparative composition by oral route at the same delivery dose. In some embodiments, following administration of the composition by sublingual or buccal route the Tmax of the substituted or unsubstituted diindolylmethane in plasma decreases by about 1000-fold compared to the Tmax following administration of a comparative composition by oral route at the same delivery dose.

Methods of Administering DIM to Avoiding Efflux and/or Influx by Membrane Transporters Membrane transporters are known to be major determinants of the pharmacokinetic, safety and efficacy profiles of drugs. In particular, more than 400 membrane transporters in two major superfamilies: ATP-binding cassette (ABC) and solute carrier (SLC), have been annotated in the human genome. It is known that transporters play a part in vivo in drug disposition, therapeutic efficacy and adverse drug reactions. The in vivo role of transporters is demonstrated in several animal species, including knockout mice and by loss-of-function genetic variants in humans. These studies have provided considerable information on the in vivo role of many ABC and SLC transporters. Clinical pharmacokinetic drug-drug interaction (DDI) studies have suggested that transporters often work together with drug-metabolizing enzymes (DMEs) in drug absorption and elimination.

P-gp

P-glycoprotein (P-gp), a 170-kDa member of the ATP-binding cassette transporter superfamily (ABCB1), is a membrane transporter protein that is known to mediate the ATP-dependent export of drugs from cells. Intestinal drug efflux by P-gp is widely recognized as a major determinant for the low or variable oral absorption of several drugs. It has been shown to be expressed in the luminal membrane of the small intestine and blood-brain barrier, and in the apical membranes of excretory cells such as hepatocytes and kidney proximal tubule epithelia. In recent years, there has been much interest in the potential role of P-gp, which, by its action of pumping drugs out of epithelial cells back into the intestinal lumen, is hypothesized to limit the oral bioavailability of a wide range of drugs. Several drugs have been shown to have low bioavailability due to the P-gp-mediated efflux occurring in the small intestine.

In some embodiments, the percentage of a composition comprising substituted or unsubstituted diindolylmethane effluxed by intestinal protein P-gp following the sublingual or buccal administration is about 0.1% to about 50% of the percentage of the same composition effluxed by intestinal protein P-gp following the oral administration, wherein the sublingual or buccal and oral administrations are at the same delivery dose. In some embodiments, the percentage of a composition comprising substituted or unsubstituted diindolylmethane effluxed by intestinal protein P-gp following the sublingual or buccal administration is about 0.1% to about 50% of the percentage of a comparative composition effluxed by intestinal protein P-gp following the oral administration, wherein the sublingual or buccal and oral administrations are at the same delivery dose. In some embodiments, the percentage of a composition comprising substituted or unsubstituted diindolylmethane effluxed by intestinal protein P-gp following the sublingual or buccal administration is about 0.1% of the percentage of a comparative composition effluxed by intestinal protein P-gp following the oral administration, wherein the sublingual or buccal and oral administrations are at the same delivery dose. In some embodiments, the percentage of a composition comprising substituted or unsubstituted diindolylmethane effluxed by intestinal protein P-gp following the sublingual or buccal administration is about 0.2% of the percentage of a comparative composition effluxed by intestinal protein P-gp following the oral administration, wherein the sublingual or buccal and oral administrations are at the same delivery dose. In some embodiments, the percentage of a composition comprising substituted or unsubstituted diindolylmethane effluxed by intestinal protein P-gp following the sublingual or buccal administration is about 0.3% of the percentage of a comparative composition effluxed by intestinal protein P-gp following the oral administration, wherein the sublingual or buccal and oral administrations are at the same delivery dose. In some embodiments, the percentage of a composition comprising substituted or unsubstituted diindolylmethane effluxed by intestinal protein P-gp following the sublingual or buccal administration is about 0.4% of the percentage of a comparative composition effluxed by intestinal protein P-gp following the oral administration, wherein the sublingual or buccal and oral administrations are at the same delivery dose. In some embodiments, the percentage of a composition comprising substituted or unsubstituted diindolylmethane effluxed by intestinal protein P-gp following the sublingual or buccal administration is about 0.5% of the percentage of a comparative composition effluxed by intestinal protein P-gp following the oral administration, wherein the sublingual or buccal and oral administrations are at the same delivery dose. In some embodiments, the percentage of a composition comprising substituted or unsubstituted diindolylmethane effluxed by intestinal protein P-gp following the sublingual or buccal administration is about 1% of the percentage of a comparative composition effluxed by intestinal protein P-gp following the oral administration, wherein the sublingual or buccal and oral administrations are at the same delivery dose. In some embodiments, the percentage of a composition comprising substituted or unsubstituted diindolylmethane effluxed by intestinal protein P-gp following the sublingual or buccal administration is about 2% of the percentage of a comparative composition effluxed by intestinal protein P-gp following the oral administration, wherein the sublingual or buccal and oral administrations are at the same delivery dose. In some embodiments, the percentage of a composition comprising substituted or unsubstituted diindolylmethane effluxed by intestinal protein P-gp following the sublingual or buccal administration is about 3% of the percentage of a comparative composition effluxed by intestinal protein P-gp following the oral administration, wherein the sublingual or buccal and oral administrations are at the same delivery dose. In some embodiments, the percentage of a composition comprising substituted or unsubstituted diindolylmethane effluxed by intestinal protein P-gp following the sublingual or buccal administration is about 4% of the percentage of a comparative composition effluxed by intestinal protein P-gp following the oral administration, wherein the sublingual or buccal and oral administrations are at the same delivery dose. In some embodiments, the percentage of a composition comprising substituted or unsubstituted diindolylmethane effluxed by intestinal protein P-gp following the sublingual or buccal administration is about 5% of the percentage of a comparative composition effluxed by intestinal protein P-gp following the oral administration, wherein the sublingual or buccal and oral administrations are at the same delivery dose. In some embodiments, the percentage of a composition comprising substituted or unsubstituted diindolylmethane effluxed by intestinal protein P-gp following the sublingual or buccal administration is about 6% of the percentage of a comparative composition effluxed by intestinal protein P-gp following the oral administration, wherein the sublingual or buccal and oral administrations are at the same delivery dose. In some embodiments, the percentage of a composition comprising substituted or unsubstituted diindolylmethane effluxed by intestinal protein P-gp following the sublingual or buccal administration is about 7% of the percentage of a comparative composition effluxed by intestinal protein P-gp following the oral administration, wherein the sublingual or buccal and oral administrations are at the same delivery dose. In some embodiments, the percentage of a composition comprising substituted or unsubstituted diindolylmethane effluxed by intestinal protein P-gp following the sublingual or buccal administration is about 8% of the percentage of a comparative composition effluxed by intestinal protein P-gp following the oral administration, wherein the sublingual or buccal and oral administrations are at the same delivery dose. In some embodiments, the percentage of a composition comprising substituted or unsubstituted diindolylmethane effluxed by intestinal protein P-gp following the sublingual or buccal administration is about 9% of the percentage of a comparative composition effluxed by intestinal protein P-gp following the oral administration, wherein the sublingual or buccal and oral administrations are at the same delivery dose. In some embodiments, the percentage of a composition comprising substituted or unsubstituted diindolylmethane effluxed by intestinal protein P-gp following the sublingual or buccal administration is about 10% of the percentage of a comparative composition effluxed by intestinal protein P-gp following the oral administration, wherein the sublingual or buccal and oral administrations are at the same delivery dose. In some embodiments, the percentage of a composition comprising substituted or unsubstituted diindolylmethane effluxed by intestinal protein P-gp following the sublingual or buccal administration is about 20% of the percentage of a comparative composition effluxed by intestinal protein P-gp following the oral administration, wherein the sublingual or buccal and oral administrations are at the same delivery dose. In some embodiments, the percentage of a composition comprising substituted or unsubstituted diindolylmethane effluxed by intestinal protein P-gp following the sublingual or buccal administration is about 30% of the percentage of a comparative composition effluxed by intestinal protein P-gp following the oral administration, wherein the sublingual or buccal and oral administrations are at the same delivery dose. In some embodiments, the percentage of a composition comprising substituted or unsubstituted diindolylmethane effluxed by intestinal protein P-gp following the sublingual or buccal administration is about 40% of the percentage of a comparative composition effluxed by intestinal protein P-gp following the oral administration, wherein the sublingual or buccal and oral administrations are at the same delivery dose. In some embodiments, the percentage of a composition comprising substituted or unsubstituted diindolylmethane effluxed by intestinal protein P-gp following the sublingual or buccal administration is about 50% of the percentage of a comparative composition effluxed by intestinal protein P-gp following the oral administration, wherein the sublingual or buccal and oral administrations are at the same delivery dose.

In some embodiments, the percentages of the composition, comprising substituted or unsubstituted diindolylmethane, for sublingual or buccal administration, effluxed by intestinal protein P-gp is quantified using a bi-directional transporter assay. In some embodiments, the percentages of the comparative composition, comprising substituted or unsubstituted diindolylmethane, for oral administration, effluxed by intestinal protein P-gp is quantified using a bi-directional transporter assay. In some embodiments, the transporter assay is a bi-directional MDR1-MDCK permeability assay. In some embodiments, a net flux ratio is calculated from the bi-directional MDR1-MDCK permeability assay.

In some embodiments, the percentages of the sublingual or buccal composition and the comparative oral composition effluxed by P-gp are proportional to the net flux ratio. In some embodiments, the net flux ratio of the sublingual or buccal composition is about 2 times to about 20 times less than the net flux ratio of the comparative oral composition. In some embodiments, the net flux ratio is the ratio of the transport of a composition from basolateral to apical and apical to basolateral direction or in other words, the ratio of measured efflux to uptake. In some embodiments, the net flux ratio of the sublingual or buccal composition is about 2 times to about 20 times less than the net flux ratio of the comparative oral composition. In some embodiments, the net flux ratio of the sublingual or buccal composition is about 2 times to about 15 times less than the net flux ratio of the comparative oral composition. In some embodiments, the net flux ratio of the sublingual or buccal composition is about 2 times to about 10 times less than the net flux ratio of the comparative oral composition. In some embodiments, the net flux ratio of the sublingual or buccal composition is about 2 times to about 5 times less than the net flux ratio of the comparative oral composition. In some embodiments, the net flux ratio of the sublingual or buccal composition is about 2 times less than the net flux ratio of the comparative oral composition. In some embodiments, the net flux ratio of the sublingual or buccal composition is about 3 times less than the net flux ratio of the comparative oral composition. In some embodiments, the net flux ratio of the sublingual or buccal composition is about 4 times less than the net flux ratio of the comparative oral composition. In some embodiments, the net flux ratio of the sublingual or buccal composition is about 5 times less than the net flux ratio of the comparative oral composition. In some embodiments, the net flux ratio of the sublingual or buccal composition is about 6 times less than the net flux ratio of the comparative oral composition. In some embodiments, the net flux ratio of the sublingual or buccal composition is about 7 times less than the net flux ratio of the comparative oral composition. In some embodiments, the net flux ratio of the sublingual or buccal composition is about 8 times less than the net flux ratio of the comparative oral composition. In some embodiments, the net flux ratio of the sublingual or buccal composition is about 9 times less than the net flux ratio of the comparative oral composition. In some embodiments, the net flux ratio of the sublingual or buccal composition is about 10 times less than the net flux ratio of the comparative oral composition. In some embodiments, the net flux ratio of the sublingual or buccal composition is about 11 times less than the net flux ratio of the comparative oral composition. In some embodiments, the net flux ratio of the sublingual or buccal composition is about 12 times less than the net flux ratio of the comparative oral composition. In some embodiments, the net flux ratio of the sublingual or buccal composition is about 13 times less than the net flux ratio of the comparative oral composition. In some embodiments, the net flux ratio of the sublingual or buccal composition is about 14 times less than the net flux ratio of the comparative oral composition. In some embodiments, the net flux ratio of the sublingual or buccal composition is about 15 times less than the net flux ratio of the comparative oral composition. In some embodiments, the net flux ratio of the sublingual or buccal composition is about 16 times less than the net flux ratio of the comparative oral composition. In some embodiments, the net flux ratio of the sublingual or buccal composition is about 17 times less than the net flux ratio of the comparative oral composition. In some embodiments, the net flux ratio of the sublingual or buccal composition is about 18 times less than the net flux ratio of the comparative oral composition. In some embodiments, the net flux ratio of the sublingual or buccal composition is about 19 times less than the net flux ratio of the comparative oral composition. In some embodiments, the net flux ratio of the sublingual or buccal composition is about 20 times less than the net flux ratio of the comparative oral composition.

OATP

Organic anion transporting polypeptides (OATP) form a family of influx transporters expressed in various tissues important for pharmacokinetics. Of the 11 human OATP transporters, OATP1B1, OATP1B3 and OATP2B1 are expressed on the sinusoidal membrane of hepatocytes and has been shown to facilitate the liver uptake of their substrate drugs. OATP1A2 is expressed on the luminal membrane of small intestinal enterocytes and at the blood-brain barrier, potentially mediating drug transport at these sites. Several clinically used drugs have been identified as substrates of OATP transporters (e.g. many statins are substrates of OATP1B1). Some drugs may inhibit OATP transporters (e.g. cyclosporine) causing pharmacokinetic drug-drug interactions.

In some embodiments, the percentage of a composition comprising substituted or unsubstituted diindolylmethane influxed into the enterocyte or liver by an OATP following the sublingual or buccal administration is about 0.1% to about 50% of the percentage of the same composition influxed into the enterocyte or liver by an OATP following the oral administration, wherein the sublingual or buccal and oral administrations are at the same delivery dose. In some embodiments, the percentage of a composition comprising substituted or unsubstituted diindolylmethane influxed into the enterocyte or liver by an OATP following the sublingual or buccal administration is about 0.1% to about 50% of the percentage of a comparative composition influxed into the enterocyte or liver by an OATP following the oral administration, wherein the sublingual or buccal and oral administrations are at the same delivery dose. In some embodiments, the percentage of a composition comprising substituted or unsubstituted diindolylmethane influxed into the enterocyte or liver by an OATP following the sublingual or buccal administration is about 0.1% of the percentage of a comparative composition influxed into the enterocyte or liver by an OATP following the oral administration, wherein the sublingual or buccal and oral administrations are at the same delivery dose. In some embodiments, the percentage of a composition comprising substituted or unsubstituted diindolylmethane influxed into the enterocyte or liver by an OATP following the sublingual or buccal administration is about 0.2% of the percentage of a comparative composition influxed into the enterocyte or liver by an OATP following the oral administration, wherein the sublingual or buccal and oral administrations are at the same delivery dose. In some embodiments, the percentage of a composition comprising substituted or unsubstituted diindolylmethane influxed into the enterocyte or liver by an OATP following the sublingual or buccal administration is about 0.3% of the percentage of a comparative composition influxed into the enterocyte or liver by an OATP following the oral administration, wherein the sublingual or buccal and oral administrations are at the same delivery dose. In some embodiments, the percentage of a composition comprising substituted or unsubstituted diindolylmethane influxed into the enterocyte or liver by an OATP following the sublingual or buccal administration is about 0.4% of the percentage of a comparative composition influxed into the enterocyte or liver by an OATP following the oral administration, wherein the sublingual or buccal and oral administrations are at the same delivery dose. In some embodiments, the percentage of a composition comprising substituted or unsubstituted diindolylmethane influxed into the enterocyte or liver by an OATP following the sublingual or buccal administration is about 0.5% of the percentage of a comparative composition influxed into the enterocyte or liver by an OATP following the oral administration, wherein the sublingual or buccal and oral administrations are at the same delivery dose. In some embodiments, the percentage of a composition comprising substituted or unsubstituted diindolylmethane influxed into the enterocyte or liver by an OATP following the sublingual or buccal administration is about 1% of the percentage of a comparative composition influxed into the enterocyte or liver by an OATP following the oral administration, wherein the sublingual or buccal and oral administrations are at the same delivery dose. In some embodiments, the percentage of a composition comprising substituted or unsubstituted diindolylmethane influxed into the enterocyte or liver by an OATP following the sublingual or buccal administration is about 2% of the percentage of a comparative composition influxed into the enterocyte or liver by an OATP following the oral administration, wherein the sublingual or buccal and oral administrations are at the same delivery dose. In some embodiments, the percentage of a composition comprising substituted or unsubstituted diindolylmethane influxed into the enterocyte or liver by an OATP following the sublingual or buccal administration is about 3% of the percentage of a comparative composition influxed into the enterocyte or liver by an OATP following the oral administration, wherein the sublingual or buccal and oral administrations are at the same delivery dose. In some embodiments, the percentage of a composition comprising substituted or unsubstituted diindolylmethane influxed into the enterocyte or liver by an OATP following the sublingual or buccal administration is about 4% of the percentage of a comparative composition influxed into the enterocyte or liver by an OATP following the oral administration, wherein the sublingual or buccal and oral administrations are at the same delivery dose. In some embodiments, the percentage of a composition comprising substituted or unsubstituted diindolylmethane influxed into the enterocyte or liver by an OATP following the sublingual or buccal administration is about 5% of the percentage of a comparative composition influxed into the enterocyte or liver by an OATP following the oral administration, wherein the sublingual or buccal and oral administrations are at the same delivery dose. In some embodiments, the percentage of a composition comprising substituted or unsubstituted diindolylmethane influxed into the enterocyte or liver by an OATP following the sublingual or buccal administration is about 6% of the percentage of a comparative composition influxed into the enterocyte or liver by an OATP following the oral administration, wherein the sublingual or buccal and oral administrations are at the same delivery dose. In some embodiments, the percentage of a composition comprising substituted or unsubstituted diindolylmethane influxed into the enterocyte or liver by an OATP following the sublingual or buccal administration is about 7% of the percentage of a comparative composition influxed into the enterocyte or liver by an OATP following the oral administration, wherein the sublingual or buccal and oral administrations are at the same delivery dose. In some embodiments, the percentage of a composition comprising substituted or unsubstituted diindolylmethane influxed into the enterocyte or liver by an OATP following the sublingual or buccal administration is about 8% of the percentage of a comparative composition influxed into the enterocyte or liver by an OATP following the oral administration, wherein the sublingual or buccal and oral administrations are at the same delivery dose. In some embodiments, the percentage of a composition comprising substituted or unsubstituted diindolylmethane influxed into the enterocyte or liver by an OATP following the sublingual or buccal administration is about 9% of the percentage of a comparative composition influxed into the enterocyte or liver by an OATP following the oral administration, wherein the sublingual or buccal and oral administrations are at the same delivery dose. In some embodiments, the percentage of a composition comprising substituted or unsubstituted diindolylmethane influxed into the enterocyte or liver by an OATP following the sublingual or buccal administration is about 10% of the percentage of a comparative composition influxed into the enterocyte or liver by an OATP following the oral administration, wherein the sublingual or buccal and oral administrations are at the same delivery dose. In some embodiments, the percentage of a composition comprising substituted or unsubstituted diindolylmethane influxed into the enterocyte or liver by an OATP following the sublingual or buccal administration is about 20% of the percentage of a comparative composition influxed into the enterocyte or liver by an OATP following the oral administration, wherein the sublingual or buccal and oral administrations are at the same delivery dose. In some embodiments, the percentage of a composition comprising substituted or unsubstituted diindolylmethane influxed into the enterocyte or liver by an OATP following the sublingual or buccal administration is about 30% of the percentage of a comparative composition influxed into the enterocyte or liver by an OATP following the oral administration, wherein the sublingual or buccal and oral administrations are at the same delivery dose. In some embodiments, the percentage of a composition comprising substituted or unsubstituted diindolylmethane influxed into the enterocyte or liver by an OATP following the sublingual or buccal administration is about 40% of the percentage of a comparative composition influxed into the enterocyte or liver by an OATP following the oral administration, wherein the sublingual or buccal and oral administrations are at the same delivery dose. In some embodiments, the percentage of a composition comprising substituted or unsubstituted diindolylmethane influxed into the enterocyte or liver by an OATP following the sublingual or buccal administration is about 50% of the percentage of a comparative composition influxed into the enterocyte or liver by an OATP following the oral administration, wherein the sublingual or buccal and oral administrations are at the same delivery dose.

Methods to Avoid Metabolism by CYP450 by Sublingual or Buccal Administration of DIM CYP450

The cytochromes P450 (CYP450) are a superfamily of hemoproteins. They represent the terminal oxidases of the mixed function oxidase system. The cytochrome P450 gene superfamily is composed of at least 207 genes that have been named based on the evolutionary relationships of the cytochromes P450. Three cytochrome P450 gene families (CYP1, CYP2 and CYP3) have been shown to be responsible for metabolism of several drugs. At least 15 cytochromes P450 have been characterized to varying degrees in the human liver. The liver contains many isoforms of cytochrome P450 and can biotransform a large variety of substances. The enterocytes lining the lumen of the intestine also have significant cytochrome P450 activity, and this activity is dominated by a single family of isozymes, 3A, and the most important isoforms in drug metabolism. Exemplary cytochromes P450s which are known to metabolize drugs in the liver include CYP3A4, CYP1A2, and CYP2B6.

Reduced Metabolism by CYP450 Family Enzymes

In some embodiments, the percentage of a composition comprising substituted or unsubstituted diindolylmethane metabolized by a CYP450 enzyme, following the sublingual or buccal administration is about 0.1% to about 50% of the percentage of the same composition metabolized by the CYP450 enzyme following the oral administration, wherein the sublingual or buccal and oral administrations are at the same delivery dose. In some embodiments, the percentage of a composition comprising substituted or unsubstituted diindolylmethane metabolized by a CYP450 enzyme, following the sublingual or buccal administration is about 0.1% to about 50% of the percentage of a comparative composition metabolized by the CYP450 enzyme following the oral administration, wherein the sublingual or buccal and oral administrations are at the same delivery dose.

In some embodiments, the percentage of a composition comprising substituted or unsubstituted diindolylmethane metabolized by at least one of CYP3A4, CYP1A2, and CYPB26, following the sublingual or buccal administration is about 0.1% to about 50% of the percentage of the same composition metabolized by at least one of CYP3A4, CYP1A2, and CYPB26 following the oral administration, wherein the sublingual or buccal and oral administrations are at the same delivery dose. In some embodiments, the percentage of a composition comprising substituted or unsubstituted diindolylmethane metabolized by at least one of CYP3A4, CYP1A2, and CYPB26, following the sublingual or buccal administration is about 0.1% to about 50% of the percentage of a comparative composition metabolized by at least one of CYP3A4, CYP1A2, and CYPB26 following the oral administration, wherein the sublingual or buccal and oral administrations are at the same delivery dose. In some embodiments, the percentage of a composition comprising substituted or unsubstituted diindolylmethane metabolized by at least one of CYP3A4, CYP1A2, and CYPB26, following the sublingual or buccal administration is about 0.1% of the percentage of a comparative composition metabolized by at least one of CYP3A4, CYP1A2, and CYPB26 following the oral administration, wherein the sublingual or buccal and oral administrations are at the same delivery dose. In some embodiments, the percentage of a composition comprising substituted or unsubstituted diindolylmethane metabolized by at least one of CYP3A4, CYP1A2, and CYPB26, following the sublingual or buccal administration is about 0.2% of the percentage of a comparative composition metabolized by at least one of CYP3A4, CYP1A2, and CYPB26 following the oral administration, wherein the sublingual or buccal and oral administrations are at the same delivery dose. In some embodiments, the percentage of a composition comprising substituted or unsubstituted diindolylmethane metabolized by at least one of CYP3A4, CYP1A2, and CYPB26, following the sublingual or buccal administration is about 0.3% of the percentage of a comparative composition metabolized by at least one of CYP3A4, CYP1A2, and CYPB26 following the oral administration, wherein the sublingual or buccal and oral administrations are at the same delivery dose. In some embodiments, the percentage of a composition comprising substituted or unsubstituted diindolylmethane metabolized by at least one of CYP3A4, CYP1A2, and CYPB26, following the sublingual or buccal administration is about 0.4% of the percentage of a comparative composition metabolized by at least one of CYP3A4, CYP1A2, and CYPB26 following the oral administration, wherein the sublingual or buccal and oral administrations are at the same delivery dose. In some embodiments, the percentage of a composition comprising substituted or unsubstituted diindolylmethane metabolized by at least one of CYP3A4, CYP1A2, and CYPB26, following the sublingual or buccal administration is about 0.5% of the percentage of a comparative composition metabolized by at least one of CYP3A4, CYP1A2, and CYPB26 following the oral administration, wherein the sublingual or buccal and oral administrations are at the same delivery dose. In some embodiments, the percentage of a composition comprising substituted or unsubstituted diindolylmethane metabolized by at least one of CYP3A4, CYP1A2, and CYPB26, following the sublingual or buccal administration is about 1% of the percentage of a comparative composition metabolized by at least one of CYP3A4, CYP1A2, and CYPB26 following the oral administration, wherein the sublingual or buccal and oral administrations are at the same delivery dose. In some embodiments, the percentage of a composition comprising substituted or unsubstituted diindolylmethane metabolized by at least one of CYP3A4, CYP1A2, and CYPB26, following the sublingual or buccal administration is about 2% of the percentage of a comparative composition metabolized by at least one of CYP3A4, CYP1A2, and CYPB26 following the oral administration, wherein the sublingual or buccal and oral administrations are at the same delivery dose. In some embodiments, the percentage of a composition comprising substituted or unsubstituted diindolylmethane metabolized by at least one of CYP3A4, CYP1A2, and CYPB26, following the sublingual or buccal administration is about 3% of the percentage of a comparative composition metabolized by at least one of CYP3A4, CYP1A2, and CYPB26 following the oral administration, wherein the sublingual or buccal and oral administrations are at the same delivery dose. In some embodiments, the percentage of a composition comprising substituted or unsubstituted diindolylmethane metabolized by at least one of CYP3A4, CYP1A2, and CYPB26, following the sublingual or buccal administration is about 4% of the percentage of a comparative composition metabolized by at least one of CYP3A4, CYP1A2, and CYPB26 following the oral administration, wherein the sublingual or buccal and oral administrations are at the same delivery dose. In some embodiments, the percentage of a composition comprising substituted or unsubstituted diindolylmethane metabolized by at least one of CYP3A4, CYP1A2, and CYPB26, following the sublingual or buccal administration is about 5% of the percentage of a comparative composition metabolized by at least one of CYP3A4, CYP1A2, and CYPB26 following the oral administration, wherein the sublingual or buccal and oral administrations are at the same delivery dose. In some embodiments, the percentage of a composition comprising substituted or unsubstituted diindolylmethane metabolized by at least one of CYP3A4, CYP1A2, and CYPB26, following the sublingual or buccal administration is about 6% of the percentage of a comparative composition metabolized by at least one of CYP3A4, CYP1A2, and CYPB26 following the oral administration, wherein the sublingual or buccal and oral administrations are at the same delivery dose. In some embodiments, the percentage of a composition comprising substituted or unsubstituted diindolylmethane metabolized by at least one of CYP3A4, CYP1A2, and CYPB26, following the sublingual or buccal administration is about 7% of the percentage of a comparative composition metabolized by at least one of CYP3A4, CYP1A2, and CYPB26 following the oral administration, wherein the sublingual or buccal and oral administrations are at the same delivery dose. In some embodiments, the percentage of a composition comprising substituted or unsubstituted diindolylmethane metabolized by at least one of CYP3A4, CYP1A2, and CYPB26, following the sublingual or buccal administration is about 8% of the percentage of a comparative composition metabolized by at least one of CYP3A4, CYP1A2, and CYPB26 following the oral administration, wherein the sublingual or buccal and oral administrations are at the same delivery dose. In some embodiments, the percentage of a composition comprising substituted or unsubstituted diindolylmethane metabolized by at least one of CYP3A4, CYP1A2, and CYPB26, following the sublingual or buccal administration is about 9% of the percentage of a comparative composition metabolized by at least one of CYP3A4, CYP1A2, and CYPB26 following the oral administration, wherein the sublingual or buccal and oral administrations are at the same delivery dose. In some embodiments, the percentage of a composition comprising substituted or unsubstituted diindolylmethane metabolized by at least one of CYP3A4, CYP1A2, and CYPB26, following the sublingual or buccal administration is about 10% of the percentage of a comparative composition metabolized by at least one of CYP3A4, CYP1A2, and CYPB26 following the oral administration, wherein the sublingual or buccal and oral administrations are at the same delivery dose. In some embodiments, the percentage of a composition comprising substituted or unsubstituted diindolylmethane metabolized by at least one of CYP3A4, CYP1A2, and CYPB26, following the sublingual or buccal administration is about 20% of the percentage of a comparative composition metabolized by at least one of CYP3A4, CYP1A2, and CYPB26 following the oral administration, wherein the sublingual or buccal and oral administrations are at the same delivery dose. In some embodiments, the percentage of a composition comprising substituted or unsubstituted diindolylmethane metabolized by at least one of CYP3A4, CYP1A2, and CYPB26, following the sublingual or buccal administration is about 30% of the percentage of a comparative composition metabolized by at least one of CYP3A4, CYP1A2, and CYPB26 following the oral administration, wherein the sublingual or buccal and oral administrations are at the same delivery dose. In some embodiments, the percentage of a composition comprising substituted or unsubstituted diindolylmethane metabolized by at least one of CYP3A4, CYP1A2, and CYPB26, following the sublingual or buccal administration is about 40% of the percentage of a comparative composition metabolized by at least one of CYP3A4, CYP1A2, and CYPB26 following the oral administration, wherein the sublingual or buccal and oral administrations are at the same delivery dose. In some embodiments, the percentage of a composition comprising substituted or unsubstituted diindolylmethane metabolized by at least one of CYP3A4, CYP1A2, and CYPB26, following the sublingual or buccal administration is about 50% of the percentage of a comparative composition metabolized by at least one of CYP3A4, CYP1A2, and CYPB26 following the oral administration, wherein the sublingual or buccal and oral administrations are at the same delivery dose.

DIM Composition, Formulations, Routes of Administration and Delivery Dosage

In some embodiments, the compositions described herein comprise a substituted or unsubstituted diindolylmethane. In some embodiments, the compositions described herein comprise a substituted or unsubstituted diindolylmethane that has been adapted to improve bioavailability. In some embodiments, the substituted or unsubstituted diindolylmethane that has been adapted to improve bioavailability is Bioresponse-diindolylmethane (BR-DIM). In some embodiments, the composition described herein comprises substituted or unsubstituted diindolylmethane that has not been adapted for improved bioavailability. In some embodiments, the substituted or unsubstituted diindolylmethane that has not been adapted for improved bioavailability is not BR-DIM. In some embodiments, the compositions described herein further comprise a substituted or unsubstituted retinoic acid based component.

In some embodiments, the retinoic acid based component is any such compound known in the art that is suitable for sublingual or buccal, oral, or topical administration. For example, in some embodiments, it is selected from a substituted or unsubstituted first generation retinoid, a substituted or unsubstituted second generation retinoid, and a substituted or unsubstituted third generation retinoid. In some embodiments, the retinoid is a substituted or unsubstituted first generation retinoid. In some embodiments, the substituted or unsubstituted first generation retinoid is selected from a substituted or unsubstituted retinol, a substituted or unsubstituted retinal, a substituted or unsubstituted tretinoin (e.g., retinoic acid or Retin A), a substituted or unsubstituted isotretinoin (e.g., Accutane™), and a substituted or unsubstituted alitretinoin. In some embodiments, the retinoid is vitamin A. In some embodiments, the retinoid is a substituted or unsubstituted second generation retinoid selected from a substituted or unsubstituted etretinate, and a substituted or unsubstituted acitretin. In some embodiments, the retinoid is a substituted or unsubstituted third generation retinoid selected from a substituted or unsubstituted tazarotene, a substituted or unsubstituted bexarotene, and a substituted or unsubstituted adapalene.

In some embodiments, the composition described herein comprises a diindolylmethane of Formula 1:

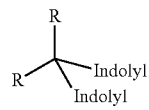

Formula 1 wherein the R groups are independently selected from hydrogen atoms and C1-C6 hydrocarbon substituents; and wherein the indolyl groups are independently selected from indole-3-yl and indole-2-yl groups; and wherein the indolyl groups are unsubstituted, or are substituted with one or more C1-C6 hydrocarbon substituents.

In some embodiments, the composition described herein comprises an unsubstituted 3,3'diindolylmethane. In some embodiments, the composition described herein comprises an unsubstituted 3,3'diindolylmethane and a vitamin A compound (e.g, vitamin A palmitate).

In some embodiments, the composition described herein comprises BR-DIM. In some embodiments, the composition described herein comprises BR-DIM and a vitamin A compound (e.g., vitamin A palmitate).

In some embodiments the composition comprising substituted or unsubstituted diindolylmethane is administered at a delivery dose that is sufficiently low to avoid toxicity, whilst still maintaining the required pharmaceutical effect. In some embodiments, the delivery dose of the composition varies depending upon whether it is a natural or synthetic product. In some embodiments, the delivery dose of the composition comprising the substituted or unsubstituted diindolylmethane is determined by whether or not the diindolylmethane has been adapted to improve bioavailability. In some embodiments, the delivery dose for a composition comprising BR-DIM is less than the delivery dose for a composition comprising substituted or unsubstituted diindolylmethane that has not been adapted to improve bioavailability.

In some embodiments, the delivery dose is from about 10 mg to about 20 mg, from about 15 mg to about 25 mg, from about 20 mg to about 30 mg, from about 25 mg to about 35 mg, from about 30 mg to about 40 mg, from about 35 mg to about 45 mg, from about 40 mg to about 50 mg, from about 45 mg to about 55 mg, from about 50 mg to about 100 mg, from about 55 mg to about 150 mg, from about 60 mg to about 200 mg, from about 65 mg to about 250 mg, from about 70 mg to about 300 mg, from about 75 mg to about 350 mg, from about 80 mg to about 400 mg, from about 85 mg to about 450 mg, from about 90 mg to about 500 mg, from about 95 mg to about 550 mg, from about 100 mg to about 600 mg, from about 110 mg to about 700 mg, from about 120 mg to about 800 mg, from about 130 mg to about 900 mg, from about 140 mg to about 1000 mg, from about 150 mg to about 1100 mg, from about 200 mg to about 1200 mg, from about 250 mg to about 1300 mg, from about 300 mg to about 1400 mg, or from about 350 mg to about 1500 mg.

In some embodiments, the delivery dose is at least 15 mg, at least 20 mg, at least 30 mg, at least 40 mg, at least 55 mg, at least 65 mg, at least 75 mg, at least 90 mg, at least 100 mg, at least 110 mg, at least 120 mg, at least 130 mg, at least 140 mg, or at least 150 mg.

In some embodiments, the delivery dose of the compositions described herein provides a daily dose of the substi-tuted or unsubstituted diindolylmethane from about 10 mg to about 20 mg, from about 15 mg to about 25 mg, from about 20 mg to about 30 mg, from about 25 mg to about 35 mg, from about 30 mg to about 40 mg, from about 35 mg to about 45 mg, from about 40 mg to about 50 mg, from about 45 mg to about 55 mg, from about 50 mg to about 100 mg, from about 55 mg to about 150 mg, from about 60 mg to about 200 mg, from about 65 mg to about 250 mg, from about 70 mg to about 300 mg, from about 75 mg to about 350 mg, from about 80 mg to about 400 mg, from about 85 mg to about 450 mg, from about 90 mg to about 500 mg, from about 95 mg to about 550 mg, from about 100 mg to about 600 mg, from about 110 mg to about 700 mg, from about 120 mg to about 800 mg, from about 130 mg to about 900 mg, from about 140 mg to about 1000 mg, from about 150 mg to about 1100 mg, from about 200 mg to about 1200 mg, from about 250 mg to about 1300 mg, from about 300 mg to about 1400 mg, or from about 350 mg to about 1500 mg.

In some embodiments, the delivery dose of the compositions described herein provides a daily dose of substituted or unsubstituted diindolylmethane that is at least 20 mg, at least 30 mg, at least 40 mg, at least 55 mg, at least 65 mg, at least 75 mg, at least 90 mg, at least 100 mg, at least 110 mg, at least 120 mg, at least 130 mg, at least 140 mg, or at least 150 mg.

In some embodiments, the composition comprising a substituted or unsubstituted diindolylmethane is administered in any of the above dosages, including the higher dosages, if desired. In some embodiments, the composition comprising a substituted or unsubstituted diindolylmethane that has been adapted to improve bioavailability is administered in any of the above dosages, including the higher dosages, if desired. In some embodiments, the substituted or unsubstituted diindolylmethane that has been adapted to improve bioavailability is BR-DIM.

In some embodiments, the composition comprising substituted or unsubstituted diinolylmethane is a formulation which is administered by sublingual or buccal route. The term "formulation which is administered by sublingual or buccal route" as used herein refers to a drug delivery formulation wherein an active compound is provided for absorption across one or more membranes in the buccal cavity, including the buccal mucosa, buccal gingiva, mucous membrane of the tongue, sublingual membrane and the soft palate. The term encompasses all suitable solid and semi-solid dosage forms, including troches, sublingual tablets, buccal tablets (i.e. a preparation which can be placed under the tongue), effervescent tablets, lollipops, capsules, films, sprays, and gels (e.g., chitosan based gels, mucoadhesive gels). The term "buccal" is used in its broadest sense to refer to the oral cavity as a whole. In some embodiments, the composition comprising a formulation which is administered by sublingual or buccal route is also suitable for administration by oral route.

In some embodiments, a comparative composition comprising substituted or unsubstituted diinolylmethane is a formulation which is administered by oral route. In some embodiments, the formulation which is administered by oral route is in the form of a tablet, capsule, gel, cream or ointment. In some embodiments, the comparative composition comprising a formulation which is administered by oral route is also suitable for administration by sublingual or buccal route.

In some embodiments, the delivery dose of the composition comprising the substituted or unsubstituted diindolylmethane depends on the route of administration.

In some embodiments the delivery dose for sublingual or buccal administration is at least 10 mg. In some embodiments the delivery dose for sublingual or buccal administration is at least 15 mg. In some embodiments the delivery dose for sublingual or buccal administration is at least 20 mg. In some embodiments the delivery dose for sublingual or buccal administration is at least 25 mg. In some embodiments the delivery dose for sublingual or buccal administration is at least 30 mg. In some embodiments the delivery dose for sublingual or buccal administration is at least 35 mg. In some embodiments the delivery dose for sublingual or buccal administration is at least 40 mg. In some embodiments the delivery dose for sublingual or buccal administration is at least 45 mg. In some embodiments the delivery dose for sublingual or buccal administration is at least 50 mg. In some embodiments the delivery dose for sublingual or buccal administration is at least 55 mg. In some embodiments the delivery dose for sublingual or buccal administration is at least 65 mg. In some embodiments the delivery dose for sublingual or buccal administration is at least 70 mg. In some embodiments the delivery dose for sublingual or buccal administration is at least 75 mg. In some embodiments the delivery dose for sublingual or buccal administration is at least 80 mg. In some embodiments the delivery dose for sublingual or buccal administration is at least 85 mg. In some embodiments the delivery dose for sublingual or buccal administration is at least 90 mg. In some embodiments the delivery dose for sublingual or buccal administration is at least 95 mg. In some embodiments the delivery dose for sublingual or buccal administration is at least 100 mg. In some embodiments the delivery dose for sublingual or buccal administration is at least 110 mg. In some embodiments the delivery dose for sublingual or buccal administration is at least 120 mg. In some embodiments the delivery dose for sublingual or buccal administration is at least 130 mg. In some embodiments the delivery dose for sublingual or buccal administration is at least 140 mg. In some embodiments the delivery dose for sublingual or buccal administration is at least 150 mg.

In some embodiments the delivery dose for sublingual or buccal administration is about 10 mg. In some embodiments the delivery dose for sublingual or buccal administration is about 15 mg. In some embodiments the delivery dose for sublingual or buccal administration is about 20 mg. In some embodiments the delivery dose for sublingual or buccal administration is about 25 mg. In some embodiments the delivery dose for sublingual or buccal administration is about 30 mg. In some embodiments the delivery dose for sublingual or buccal administration is about 35 mg. In some embodiments the delivery dose for sublingual or buccal administration is about 40 mg. In some embodiments the delivery dose for sublingual or buccal administration is about 45 mg. In some embodiments the delivery dose for sublingual or buccal administration is about 50 mg. In some embodiments the delivery dose for sublingual or buccal administration is about 55 mg. In some embodiments the delivery dose for sublingual or buccal administration is about 65 mg. In some embodiments the delivery dose for sublingual or buccal administration is about 70 mg. In some embodiments the delivery dose for sublingual or buccal administration is about 75 mg. In some embodiments the delivery dose for sublingual or buccal administration is about 80 mg. In some embodiments the delivery dose for sublingual or buccal administration is about 85 mg. In some embodiments the delivery dose for sublingual or buccal administration is about 90 mg. In some embodiments the delivery dose for sublingual or buccal administration is about 95 mg. In some embodiments the delivery dose for sublingual or buccal administration is about 100 mg. In some embodiments the delivery dose for sublingual or buccal administration is about 110 mg. In some embodiments the delivery dose for sublingual or buccal administration is about 120 mg. In some embodiments the delivery dose for sublingual or buccal administration is about 130 mg. In some embodiments the delivery dose for sublingual or buccal administration is about 140 mg. In some embodiments the delivery dose for sublingual or buccal administration is about 150 mg.

In some embodiments the delivery dose for oral administration is at least 10 mg. In some embodiments the delivery dose for oral administration is at least 15 mg. In some embodiments the delivery dose for oral administration is at least 20 mg. In some embodiments the delivery dose for oral administration is at least 25 mg. In some embodiments the delivery dose for oral administration is at least 30 mg. In some embodiments the delivery dose for oral administration is at least 35 mg. In some embodiments the delivery dose for oral administration is at least 40 mg. In some embodiments the delivery dose for oral administration is at least 45 mg. In some embodiments the delivery dose for oral administration is at least 50 mg. In some embodiments the delivery dose for oral administration is at least 55 mg. In some embodiments the delivery dose for oral administration is at least 65 mg. In some embodiments the delivery dose for oral administration is at least 70 mg. In some embodiments the delivery dose for oral administration is at least 75 mg. In some embodiments the delivery dose for oral administration is at least 80 mg. In some embodiments the delivery dose for oral administration is at least 85 mg. In some embodiments the delivery dose for oral administration is at least 90 mg. In some embodiments the delivery dose for oral administration is at least 95 mg. In some embodiments the delivery dose for oral administration is at least 100 mg. In some embodiments the delivery dose for oral administration is at least 110 mg. In some embodiments the delivery dose for oral administration is at least 120 mg. In some embodiments the delivery dose for oral administration is at least 130 mg. In some embodiments the delivery dose for oral administration is at least 140 mg. In some embodiments the delivery dose for oral administration is at least 150 mg.

In some embodiments the delivery dose for oral administration is about 10 mg. In some embodiments the delivery dose for oral administration is about 15 mg. In some embodiments the delivery dose for oral administration is about 20 mg. In some embodiments the delivery dose for oral administration is about 25 mg. In some embodiments the delivery dose for oral administration is about 30 mg. In some embodiments the delivery dose for oral administration is about 35 mg. In some embodiments the delivery dose for oral administration is about 40 mg. In some embodiments the delivery dose for oral administration is about 45 mg. In some embodiments the delivery dose for oral administration is about 50 mg. In some embodiments the delivery dose for oral administration is about 55 mg. In some embodiments the delivery dose for oral administration is about 65 mg. In some embodiments the delivery dose for oral administration is about 70 mg. In some embodiments the delivery dose for oral administration is about 75 mg. In some embodiments the delivery dose for oral administration is about 80 mg. In some embodiments the delivery dose for oral administration is about 85 mg. In some embodiments the delivery dose for oral administration is about 90 mg. In some embodiments the delivery dose for oral administration is about 95 mg. In some embodiments the delivery dose for oral administration is about 100 mg. In some embodiments the delivery dose for oral administration is about 110 mg. In some embodiments the delivery dose for oral administration is about 120 mg. In some embodiments the delivery dose for oral administration is about 130 mg. In some embodiments the delivery dose for oral administration is about 140 mg. In some embodiments the delivery dose for oral administration is about 150 mg.

In some embodiments, the delivery doses for administration by sublingual or buccal route and by oral route are the same. In some embodiments, the delivery dose for administration by sublingual or buccal route is less than the delivery dose for administration by oral route.

In some embodiments, the compositions described herein comprise substituted or unsubstituted diindolylmethane in a dose which is a fraction of the daily dose, such as a half of the daily dose, or a quarter of the daily dose, and thus is present in a half or a quarter of any of the dosages recited above. In these embodiments, each dose fraction is taken separately over time to spread the dose across the day.

In some embodiments, the compositions described herein further comprise a substituted or unsubstituted retinoic acid based component. In some embodiments, the retinoic acid based component is administered at a dosage that it is sufficiently low to avoid toxicity, whilst still maintaining the required pharmaceutical effect. In some embodiments, the delivery dosage of the retinoic acid based component depends on the bioavailability of the same. In some embodiments, the bioavailability of the substituted or unsubstituted retinoic acid based component varies depending upon whether it is a natural or synthetic product. In some embodiments, the bioavailability of the substituted or unsubstituted retinoic acid based component may vary depending on whether it has been adapted to improve its bioavailability. In some embodiments, the delivery doses of the compositions described herein provides a daily dose of the substituted or unsubstituted retinoic acid based component from about 0.05 mg to about 3 mg, about 0.1 to about 1 mg, about 0.1 to about 5 mg, about 1 mg to about 15 mg, about 10 mg to about 45 mg, about 25 mg to about 100 mg, about 75 mg to about 200 mg, about 150 mg to about 250 mg. In some embodiments, the delivery doses of the compositions described herein provides a daily dose of the substituted or unsubstituted retinoic acid based component that is at least 0.05 mg, at least 0.1 mg, at least 0.2 mg, at least 0.4 mg, at least 0.5 mg, at least 0.6 mg, at least 0.7 mg, at least 0.8 mg, at least, 0.9 mg, at least 1 mg, at least 5 mg, or at least 10 mg. In some embodiments, the delivery doses of the compositions described herein provides a daily dose of the substituted or unsubstituted retinoic acid based component that is about 0.05 mg, about 0.1 mg, about 0.2 mg, about 0.4 mg, about 0.5 mg, about 0.6 mg, about 0.7 mg, about 0.8 mg, about 0.9 mg, about 1 mg, about 5 mg, or about 10 mg. In some embodiments, the delivery doses of the compositions described herein provides a daily dose of the substituted or unsubstituted retinoic acid based component that is up to 15 mg, up to 10 mg, up to 9 mg, up to 8 mg, up to 7 mg, up to 6 mg, up to 5 mg, up to 2.5 mg, up to 2 mg, up to 1 mg, or up to 0.5 mg.

In some embodiments, daily dosage of the composition comprising a substituted or unsubstituted diindolylmethane and optionally a substituted or unsubstituted retinoic acid based component is provided in the form of one or more unit doses In some embodiments, daily dosage of the composition comprising a substituted or unsubstituted diindolylmethane and optionally a substituted or unsubstituted retinoic acid based component is provided in the form of 2 to 4 unit doses. In these embodiments the two or more unit doses are taken during the course of a single day, such as one unit dose in the morning and one unit dose in the evening, or four unit doses spread evenly across the day, or two unit doses simultaneously twice a day.

Methods for Preparation

In some embodiments, are provided, methods for preparing the compositions described herein, for use in the methods described herein, of treating acne or rosacea. In some embodiments, using the methods described herein, a composition suitable for sublingual or buccal administration is prepared. In some embodiments, using the methods described herein, a comparative composition suitable for oral administration is prepared. In some embodiments, using the methods described herein, a composition suitable for both sublingual or buccal and oral administration is prepared In some embodiments, any methods known in the art for blending or mixing various components of the composition are employed. In some embodiments, the methods employed are methods for blending and/or mixing powders. In some embodiments, the method comprises mixing substituted or unsubstituted diindolylmethane with one or more pharmaceutically acceptable excipients and/or additives, and optionally with a substituted or unsubstituted retinoic acid based component, to form the composition. In some embodiments, the substituted or unsubstituted diindolylmethane, and the substituted or unsubstituted retinoic acid based component are each, separately from each other, mixed with one or more pharmaceutically acceptable excipients and/or additives before being mixed together to form the composition. In some embodiments, the substituted or unsubstituted diindolylmethane, the substituted or unsubstituted retinoic acid based component, and/or pharmaceutically acceptable excipients are added sequentially to the mixture during the mixing process.

In some embodiments, the selection of the pharmaceutically acceptable excipients and the method of blending are adapted in order to overcome any mixing, flow and fill issues or punch issues with the composition. In some embodiments, the composition comprising a substituted or unsubstituted diindolylmethane is provided in micro-encapsulated form, such that the powder particles have a tendency to clump together. In some embodiments, the composition comprising a first component, comprising a substituted or unsubstituted diindolylmethane is blended using a method that is adapted to avoid creating hot spots of increased concentrations of the active ingredients. In some embodiments, the composition comprising a substituted or unsubstituted diindolylmethane, and optionally a substituted or unsubstituted retinoic acid based component, is blended using a method that involves short processing/blending times, to protect the composition from light and air, wherein the composition is hygroscopic and light sensitive. In some embodiments, the composition comprising a substituted or unsubstituted diindolylmethane, and optionally a substituted or unsubstituted retinoic acid based component, is prepared in the form of a powder, and the powder is protected from both light and air, during storage.

In some embodiment, one or more of microcrystalline cellulose, magnesium silicate, tricalcium phosphate, and magnesium stearate (a traditional lubricant) are employed as pharmaceutically acceptable additives and excipients, in preparing the compositions described herein, to help with flow characteristics and/or lubrication. In some embodiments, other pharmaceutically acceptable additives and excipients known in the art are employed if desired. In some embodiments, the composition comprises 50.0-65.0% by weight of tri-calcium phosphate. In some embodiments, the composition comprises 55.0-60.0% by weight, or 57.0-59.0% by weight of tri-calcium phosphate. In some embodiments, the composition comprises about 58% by weight of tri-calcium phosphate. In some embodiments, the composition comprises about 58.3% by weight of tri-calcium phosphate.

In some embodiments, the correct blending of all ingredients is desirable in achieving uniform capsule fills of the compositions as described herein. In some embodiments, the correct blending of all ingredients is desirable in achieving uniform capsule fills of the compositions as described herein. In some embodiments, a V-blender is highly effective for successful mixing. In some embodiments, a minimum 316 grade stainless steel vessel is used for the mixing process. In some embodiments, sieving is performed at one or more of the start, the middle, and the end of the mixing process. In some embodiments, blend studies to confirm blend uniformity are completed to validate the method and formulation, using methods and techniques known in the field.

In one exemplary embodiment, the sublingual or buccal formulation comprises: 50-75 mg BR-DIM; 200 µg vitamin A palmitate retinol equivalents (366.4 µg retinyl palmitate) (This is equivalent to 2.666 mg of 250,000 IU/g vitamin A palmitate (BASF); 100-175 mg tricalcium phosphate; 10-20 mg microcrystalline cellulose; 5-10 mg vitamin C (ascorbic acid); 5-10 mg fumed silicon dioxide (or a fine particle precipitated silica); 3-6 mg magnesium stearate.

In one exemplary embodiment, the oral formulation comprises: 50-75 mg BR-DIM; 200 µg vitamin A palmitate retinol equivalents (366.4 µg retinyl palmitate) (This is equivalent to 2.666 mg of 250,000 IU/g vitamin A palmitate (BASF); 100-175 mg tricalcium phosphate; 10-20 mg microcrystalline cellulose; 5-10 mg vitamin C (ascorbic acid); 5-10 mg fumed silicon dioxide (or a fine particle precipitated silica); 3-6 mg magnesium stearate.

Certain Definitions

Unless defined otherwise, all technical and scientific terms used herein have the same meaning as is commonly understood by one of skill in the art to which the claimed subject matter belongs. In the event that there is a plurality of definitions for terms herein, those in this section prevail.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting.

As used herein, the term "about" is used synonymously with the term "approximately." Illustratively, the use of the term "about" with regard to a certain therapeutically effective pharmaceutical dose indicates that values slightly outside the cited values, e.g., plus or minus 0.1% to 10%, are also effective and safe.

The term "patient", "subject" or "individual" are used interchangeably. As used herein, they refer to individuals suffering from a disorder, and the like, encompasses mammals and non-mammals. None of the terms require that the individual be under the care and/or supervision of a medical professional. Mammals are any member of the Mammalian class, including but not limited to humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In some embodiments of the methods and compositions provided herein, the individual is a mammal. In preferred embodiments, the individual is a human.

The terms "treat," "treating" or "treatment," and other grammatical equivalents as used herein, include alleviating, abating or ameliorating a disease or condition or one or more symptoms thereof, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the individual, notwithstanding that the individual is still be afflicted with the underlying disorder. For prophylactic benefit, the compositions are administered to an individual at risk of developing a particular disease, or to an individual reporting one or more of the physiological symptoms of a disease, even though a diagnosis of this disease has not been made.

The terms "administer," "administering", "administration," and the like, as used herein, refer to the methods that may be used to enable delivery of compounds or compositions to the desired site of biological action. These methods include, but are not limited to sublingual or buccal routes, oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein.

The term "acceptable" as used herein, with respect to a formulation, composition or ingredient, means having no persistent detrimental effect on the general health of the individual being treated.

The term "pharmaceutically acceptable" as used herein, refers to a material, such as a carrier or diluent, which does not abrogate the biological activity or properties of the compounds described herein, and is relatively nontoxic, i.e., the material may be administered to an individual without causing undesirable biological effects or interacting in a deleterious manner with any of the components of the composition in which it is contained.

The term "DIM" as used herein, refers to a substituted or unsubstituted diindolylmethane compound.

The term "BR-DIM" or "BioResponse DIM" as used herein, refers to an unsubstituted DIM, provided by BioResponse LLC.

The term "maximum concentration" or Cmax as used herein, refers to the Cmax refers to the maximum (or peak) serum concentration that the substituted or unsubstituted diindolylmethane achieves in the plasma after it has been administrated and prior to the administration of a second dose.

The term "time to maximum concentration" or Tmax as used herein, refers to the time at which the Cmax is observed.

The term "area under the curve" or AUC or $AUC_{0-inf}$ as used herein, refers to the area under the curve, also known as the definite integral, in a plot of concentration of drug in blood plasma against time.

The term "unit dose" as used herein, refers to an amount of substituted or unsubstituted diindolylmethane contained in one discreet pharmaceutical dosage form. Examples of pharmaceutical dosage form that contains a unit dose include but are not limited to a tablet, a capsule, a buccal tablet, a sub-lingual tablet, an orally-disintegrating tablet, an effervescent tablet, a lollipop, a lozenge, a troche, a liquid solution or suspension, powder or liquid or solid crystals packed within a single tablet or capsule, a cream, a gel, an ointment, a lotion.

EXAMPLES

The following specific, non-limiting examples are to be construed as merely illustrative, and do not limit the present disclosure of the scope of the disclosure. Without further elaboration, it is believed that one skilled in the art can, based on the description herein, utilize the present disclosure to its fullest extent.

Example 1: Effect of the Route of Administration on the PK Profile of DIM in Plasma The objective of this study is to determine the pharmacokinetic (PK) profile of a diindolylmethane (DIM) formulation in plasma following single and multiple doses of DIM, administered either by sublingual route or by oral route. The DIM formulation for this study is synthesized and prepared using any of the methods described above.

Participants will be grouped into (a) Group 1: DIM administered by oral route and (b) Group 2: DIM administered by sublingual or buccal route.

Part 1: Plasma Pharmacokinetics of DIM Formulation after a Single Oral 75 mg Dose Participants of Groups 1 and 2 will be administered, orally and by the sublingual or buccal route respectively, a single 90 mg dose of the DIM formulation. Blood samples will be drawn from the participants at baseline and at 0.5, 1.0, 1.5, 2, 3, 4, 6, 8, 9 h, following administration of the DIM formulation dosage, on day 1.

Part 2: Pharmacokinetic Profile of DIM Following Bi-Daily Dosing for 4 Weeks.

In the second part of the study, participants of Groups 1 and 2 will be administered, orally and by the sublingual or buccal route respectively, on days 1 through 28, a single dose of 45 mg of the DIM formulation twice daily (i.e. each participant will receive a total of 90 mg DIM per day). Blood samples will be taken at the completion of treatment as per the schedule described for Part 1.

For each part of the study, pharmacokinetic parameters, including but not limited to, maximum concentration ($C_{max}$), time to $C_{max}$ ($T_{max}$), biological half-life (t½), and area under the concentration-time curve ($AUC_{0-inf}$) will be calculated for all subjects who complete the respective part. It is anticipated that a one-compartment elimination model will fit the data.

Example 2: Effect of Sublingual or Buccal DIM Formulation on the Activity of Certain Hepatic CYP450 Enzymes The objective of this study is to determine the susceptibility of a sublingual or buccal DIM formulation to be metabolized by certain hepatic CYP-450 enzymes. The study is carried out according to methods described in Chu et al. (2009, Drug Metab Dispos 37; 1339-1354).

Exemplary protocol includes the following steps:

Fresh or platable cryopreserved hepatocytes, are plated as either monolayer or sandwich culture, with a 1 to 2 day recovery period after plating.

The hepatocytes are treated, in triplicates, with varying concentrations of a sublingual or buccal DIM formulation and positive controls for 2 to 3 days (changing medium with test compounds every 24 h) in media containing ITS (Insulin-Transferrin-Selenium), dexamethasone, and penicillin-streptomycin as media supplements.

Exemplary positive controls include, but are not limited to, omeprazole (25-50 µM), phenobarbital (1000 µM), and rifampicin (10 µM) for CYP1A2, 2B6, and 3A4, respectively, at concentrations known to elicit maximal induction response.

The effect of sublingual or buccal DIM formulation in inducing the hepatic CYP enzymes is calculated by an empirical approach such as percentage of change compared with the positive control or a mathematical or correlation-based approach, using the therapeutic Cmax drug concentration at steady state as a benchmark.

The hepatocyte induction experiment is deemed to be acceptable if the CYP1A2, CYP2B6, and CYP3A4 positive controls exhibit ≥2-fold vehicle control catalytic activity of the CYPs and ≥6-fold vehicle control mRNA level.

Example 3: Efflux of Sublingual or Buccal DIM Formulation and Oral DIM Formulation by P-gp The objective of this study is to assess the susceptibility of a sublingual or buccal DIM formulation to be effluxed by transporter protein (e.g., P-gp). The study is carried out using a bi-directional transporter assay, e.g., Cyprotex™ MDR1-MDCK Permeability assay.

A first experiment is carried out by seeding MDR1-MDCK cells (which are Madin Darby canine kidney (MDCK) cells transfected with the MDR1 gene, the gene encoding for the efflux protein, P-glycoprotein (P-gp)) on a Multiscreen™ plate (Millipore, Mass., USA) to form a confluent monolayer over 4 days prior to the experiment. On day 4, the sublingual or buccal DIM formulation being tested is added to the apical side (donor) of the membrane and the transport of the compound from the apical compartment to the basolateral (acceptor) compartment (A–B) across the monolayer is monitored over a 60 min time period. Next, the sublingual or buccal DIM formulation being tested is added to the basolateral (donor) side of the membrane and transport from the basolateral compartment to the apical (acceptor) compartment (B–A) is monitored over a 60 min time period. In some embodiments, the accumulated amount of sublingual or buccal DIM formulation appearing in the AP compartment over time, dQ/dt, will be used to calculate the apparent permeability (Papp) using the following equation: Papp=dQ/dt×1/(A×Co), where A is the area of the filter and C0 is the initial concentration of sublingual or buccal DIM formulation in the donor compartment. Papp is calculated both for the apical to basolateral ($Papp_{A-B}$) and basolateral to apical ($Papp_{B-A}$) transports. In some embodiments, the net flux ratio is calculated by dividing the $Papp_{B-A}$ by the $Papp_{A-B}$.

A second experiment is carried out, using the same protocol described above for the first experiment, with an oral DIM formulation. The net flux ratio of the second experiment is compared to that of the first experiment.

Example 4: Improved Efficacy of Rosacea Treatment by Sublingual or Buccal Administration of DIM The objective of this study is to determine the efficacy of a diindolylmethane (DIM) formulation in treating rosacea following a 4 week treatment with DIM, administered either by sublingual route or by oral route. The DIM formulation for this study is synthesized and prepared using any of the methods described above.

Participants will be grouped into (a) Group 1: DIM administered by oral route and (b) Group 2: DIM administered by sublingual or buccal route Participants of Groups 1 and 2 will be administered, orally and by the sublingual or buccal route respectively, on days 1 through 28, a single dose of 45 mg of the DIM formulation twice daily (i.e. each participant will receive a total of 90 mg DIM per day). After completion of the study participants will be requested to self-report on certain skin parameters related to rosacea, e.g., redness, flushing, dryness, red bumps, swelling.

Example 5: Improved Efficacy of Acne Treatment by Sublingual or Buccal Administration of DIM The objective of this study is to determine the efficacy of a diindolylmethane (DIM) formulation in treating acne following a 4 week treatment with DIM, administered either by sublingual route or by oral route. The DIM formulation for this study is synthesized and prepared using any of the methods described above.

Participants will be grouped into (a) Group 1: DIM administered by oral route and (b) Group 2: DIM administered by sublingual or buccal route Participants of Groups 1 and 2 will be administered, orally and by the sublingual or buccal route respectively, on days 1 through 28, a single dose of 45 mg of the DIM formulation twice daily. After completion of the study skin biophysical parameters related to acne, including but not limited to skin sebum and stratum corneum hydration levels, transepidermal water loss values, pH, erythema and hair growth parameters such as total number, density and proportion of anagen hair, of the study participants will be assessed.

Example 6: Effect of the Route of Administration on the PK Profile of DIM+Vitamin A in Plasma This is a Phase 1 randomized, open label, two-sequence cross-over, study in healthy participants to determine the pharmacokinetics of Diindolylmethane (DIM) following single and multiple doses of an oral and sublingual formulation of DIM+Vitamin A. The formulations for this study are synthesized and prepared using any of the methods described above.

This randomized phase I trial has two main objectives:
To determine the comparative PK profile of DIM in plasma following a single 90 mg oral dose of DIM compared to a single sublingual 90 mg dose of DIM. Both formulations will contain a total of 800 µg Retinol Activity Equivalents (RAE) or RE of Vitamin A.

To assess the comparative PK profile of DIM in plasma following daily administration of 90 mg given as 2 capsules administered b.i.d., and a 90 mg dose of a sublingual form of DIM given as 1 pastille b.i.d., over 14 days. Both formulations will contain a total of 800 µg RE.

Study Design

This will be an open-label, randomized, cross-over, two-sequence study. Recruitment will continue until 10 male and 10 female participants have completed both parts of the study PK evaluation.

A participant study completer is defined as a participant who has received both single and multiple doses of the oral and sublingual formulations and who has completed all of the requisite evaluations. Participants will be given a wash-out period of between 1 and 3 weeks after completing one part and before commencing the next.

All participants will complete two treatments: Part 1, single (a) and multiple (b) oral dosing, and Part 2, single (a) and multiple (b) sublingual dosing. Each treatment will be followed by a washout period of at least 7 days. Participants will be randomized as to which treatment sequence they receive. All participants will be randomly selected for initial enrolment into either Part 1 or Part 2 of the study, that is to say, to commence with either Oral Formulation 1 (Part 1) or Sublingual Formulation 1 (Part 2); all participants will be enrolled into both Parts of the study.

Dosing Regimen

Part 1a: All participants on day one, after an overnight fast (of at least 8 hours), will receive a single oral dose (4 capsules) of 90 mg DIM+800 µg retinol equivalents (RE), Oral Formulation 1. Blood samples over a 24-hour period (0, (prior to dosing), 0.5, 1, 1.5, 2, 3, 4, 6, 9, 12 & 24 hr), and urine (0, (prior to dosing), 0-4, 4-8 & 12-24 hr) over that 24-hour period will be collected. DIM levels, determined using a validated assay, will be determined from the plasma to determine the PK profile of DIM; levels of DIM in the urine samples will also be determined.

Part 1b: After a minimum of a 7-day wash-out period, Oral Formulation 1 will be taken daily in the morning, as two capsules b.i.d. after an overnight fast (of at least 8 hours), and prior to retiring at night (after fasting for at least 3 hours), for 13 days (this dose is equivalent to the single oral dose employed in Part 1a). On Day 14, participants will receive their final dose in the morning after an overnight fast. This will be followed by blood sampling and urine collection as is described in Part 1a. On the day (Day 15) following the last dose (the morning of Day 14), participants will have a single blood draw (24-hour blood sample) and to provide the 12-24-hour urine collection sample. The PK profile of DIM at steady state in the plasma will be assessed; levels of DIM in the urine samples will also be determined.

There will be a minimum of 7 days between treatment periods Parts 1 and 2.

Part 2a: A single dose (2 pastilles) of sublingual formulation Sublingual Formulation 1 containing the same concentrations of DIM and RE as for the oral dose (Oral Formulation 1), will be given after an overnight fast of at least 8 hours, after which blood and urine samples will be taken and evaluated over a 24-hour period as described in Part 1a.

Part 2b: After a minimum 7-day wash-out period, Sublingual Formulation 1 will be taken daily, as two administrations (one pastille b.i.d), in the morning after an overnight fast (of at least 8 hours), and prior to retiring at night (after fasting for at least 3 hours), for 13 days. The daily dose will be equivalent to the single dose employed in Part 2a. On Day 14, participants will receive their morning dose after an overnight fast (of at least 8 hours). This will be followed by blood sampling and urine collection as described in Part 1a. On the day (Day 15) following the last dose (the morning of Day 14), participants will have a single blood draw (24-hour blood sample) and provide the 12-24-hour urine sample. The PK profile of DIM at steady state in the plasma will be assessed. Levels of DIM in the urine samples will also be determined.

In addition, for each treatment period urine samples will be provided on day 1, prior to the first dose, and day 14, to assess urinary levels of cotinine, and DIM obtained from the diet. Breathalyser assessment for alcohol will also be performed prior to enrollment, and before the start of each phase of the study. After completion of study intervention, participants with ongoing adverse effects (AEs) will be followed for at least 1 week, to record any observed AE, or until resolution of the AE, as deemed appropriate by the study physician.

Participants will complete a 3-day food diary at the beginning and end of Part B for both Parts 1 &2.

Participant Selection

A. Inclusion Criteria
1. Healthy males and females, between the ages of 18-35 at the time of screening.
2. Nonsmoker confirmed by urine cotinine test and has not used nicotine products (or nicotine replacement products) in the preceding 6 months prior to screening
3. Haemoglobin: males: 130-180 g/L; females: 115-165 g/L
4. White Blood Cell Count: 4.0-11.0×10$^9$/L
5. Creatinine: Males 64-104 μmol/L; females 49-90 μmol/L
6. eGFR>60 ml/min/1.73m2
7. Albumin 35-50 g/L
8. Bilirubin within the upper limit of normal (ULN)
9. AST and ALT within the upper limit of normal (ULN)
10. Alkaline phosphatase 30-130 iu/L
11. Body mass index>20 and <25
12. No serious, acute, unstable, chronic, or recurring medical conditions
13. Agree to refrain from consumption of cruciferous vegetables within 2 weeks of, and during the study period as confirmed by urinary assay for the presence of DIM or I3C (indole-3 carbinol). Cruciferous vegetables include broccoli, cabbage (including coleslaw), cauliflower, bok-choy, Brussels sprouts, collards, kale, kohlrabi, mustard greens, rutabaga, turnip, and watercress.
14. Participants must have refrained from ingesting grapefruit or grapefruit juice for two weeks prior to inclusion into the study, and throughout the study. Other food supplements must be excluded for the duration of the study
15. No serious drug allergies or other serious intolerance or allergies as determined by the Investigator (mild seasonal allergies allowed).
16. No chronic conditions, including headaches, dysphoria, fatigue, dizziness, blurred vision, insomnia, rhinorrhea, nausea, vomiting, abdominal pain, diarrhea, constipation, menopausal hot flashes/night sweats, or clinically significant premenstrual syndrome
17. No requirement for chronic drug therapy
18. No alcohol ingestion within 48 hours of study visits
19. No prior chemotherapy
20. No concurrent regular medications or any recent change in medications or dosage of medications or hormones aside from hormonal contraception
21. No concurrent food supplements or vitamins
22. If participants are coffee drinkers, their daily intake should not exceed 500 mg caffeine per day. If this criterion is met, then it is requested that the drinking habits (number or strength of coffee drinks) will not change for 2 weeks before and during the study.
23. If a female participant on a combination oral contraceptive is enrolled into the study, it is anticipated that both the dose and composition of this contraceptive will remain constant (progestogen only oral contraceptives or implants are not permitted)
24. Available to attend visits for the duration of the study B. Exclusion Criteria
1. Participants who report receiving any investigational drug within 3 months prior to the commencement of the study.
2. Participants who report any presence or history of a clinically significant disorder involving the cardiovascular, respiratory, renal, gastrointestinal, immunologic, hematologic, endocrine, or neurologic system(s) or psychiatric disease as determined by the clinical investigator(s).
3. Participants whose clinical laboratory test values are outside the accepted reference range (Upper Limit of Normal (ULN)).
4. Participants who demonstrate a reactive screen for hepatitis B surface antigen, hepatitis C antibody, or HIV antibody.
5. Female participants who are pregnant, have conceived and are lactating, or who are of child-bearing potential and who do not agree to employ or maintain standard methods of contraception for the duration of the study.
6. Participants who report a history of allergic response(s) to any of the ingredients in the formulations tested or its components.
7. Participants who report the use of any systemic prescription medication in the 14 days prior to dosing that have been excluded (combined oral contraceptives, lipid-lowering and anti-hypertensive medications are permitted).
8. Participants who report the use of any over-the-counter (OTC) medication (with the exception of low dose aspirin and paracetamol) in the 3 days prior to dosing.
9. Participants who report a clinically significant illness during the 4 weeks prior to dosing, or any condition, that in the Investigator's opinion, compromises the participant's ability to meet the protocol requirements or to complete the study.
10. Participants who report a history of drug or alcohol addiction or abuse within the past year.
11. Participants who demonstrate a positive alcohol breath test.
12. Participants who demonstrate a positive drug abuse result.
13. Participants who report donating greater than 150 mL of blood within 28 days prior to dosing. All participants will be advised not to donate blood for four weeks after completing the study.
14. Participants who report donating plasma (e.g. plasmapheresis) within 14 days prior to dosing. All participants will be advised not to donate plasma for four weeks after completing the study.
15. Participants who report exaggerated gastrointestinal disturbances (e.g. diarrhoea, constipation, nausea, vomiting)
16. Any condition that, in the investigator's opinion, compromises the participant's ability to meet protocol requirements or to complete the study.
17. Pharmacokinetic Analysis An appropriate PK data package (e.g. WinNonlin, ex. Pharsight) will be employed in order to provide a complete PK profile of DIM in the plasma over the study period. The variables that will be determined are the primary and derived PK parameters: $C_{max}$, $T_{max}$, $k_{elim}$, $t_{1/2}$, $AUC_{0-4}$, $AUC_{0-inf}$. The relative bioavailability: $F_{SUBLINGUAL}/F_{ORAL}$ ($F_{sl}/F_{oral}$) will be determined from the relationship: $(AUC_{sl}/AUC_{oral})* (Dose_{oral}/Dose_{sl})$. The values will be determined for each dosage form after single (end of Day 1) and multiple dosing (end of day 15) and the appropriate comparative assessments made for the two dosage forms.

Example 7: Sublingual Administration Increases Maximal Plasma Concentration (Cmax) and Bioavailability (AUC) of DIM in the Plasma The objective of this study was to determine the pharmacokinetic (PK) profile of a diindolylmethane (DIM) formulation in plasma following single and multiple doses of DIM, administered either by sublingual route or by oral route. The DIM formulation for this study was an exemplary formulation synthesized and prepared using the methods described above.

Participants were grouped into (a) Group 1: DIM administered by oral route and (b) Group 2: DIM administered by sublingual route.

Results: Plasma Pharmacokinetics of DIM Formulation after a Single Oral or Sublingual Dose Participants were divided into two groups and were administered, orally and sublingually, respectively, a single 90 mg dose of the DIM formulation, in the form of 4 capsules. These participants were not exposed to DIM earlier and thus were naïve subjects. It was observed that the mean Cmax for the sublingual administration was 38 ng/mL whereas for the oral dose was about 15 ng/mL, as shown in FIG. 1. Thus, the Cmax for sublingual administration of DIM was about 2.5 fold, or about 40% higher than the oral administration. The bioavailability of DIM was derived from AUC after the single 90 mg dose, sublingually or orally, in the naïve subjects. As can be seen from the plot in FIG. 1, the AUC in the naïve subjects was about 2 times higher upon sublingual administration than oral administration.

Results: Pharmacokinetic Profile of a Single Dose of DIM, Oral or Sublingual, Following Daily Dosing for 14 Days.

Figure 2:
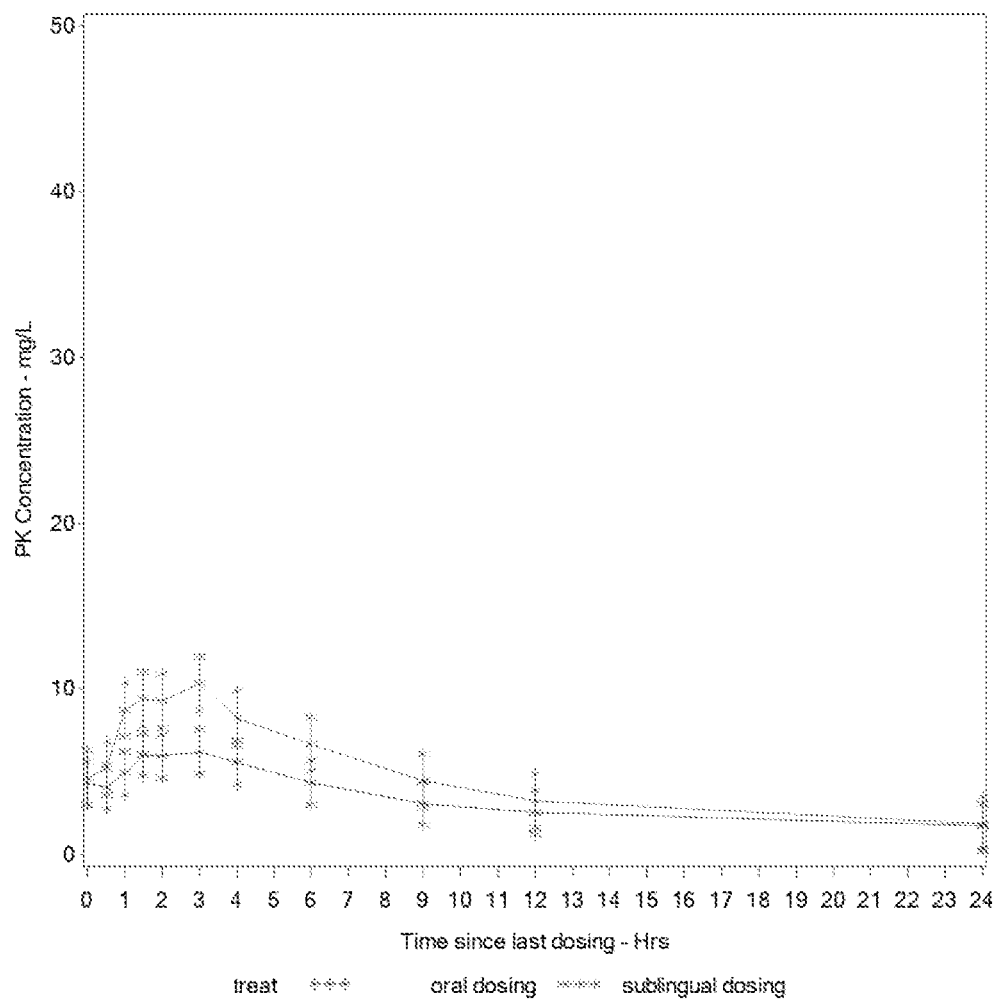
FIG. 2 illustrates plasma concentration of DIM after oral or sublingual administration of a single dose of a DIM formulation, which single dose was preceded by multiple doses of oral or sublingual administration. The top line, in light gray, shows the plasma concentration after sublingual administration and the bottom line, in dark gray, shows the same after oral administration.

Participants were divided in two groups. One group was administered a daily oral 90 mg dose of DIM on days 1-14, and another group was administered a daily sublingual 90 mg dose of DIM on days 1 through 14. The 90 mg DIM dosages were administered as 45 mg in the morning (2 capsules) and 45 mg at night (2 capsules). On day 15, a single 45 mg oral dose of DIM was administered to the oral group and a single 45 mg sublingual dose of DIM was administered to the sublingual group, followed by collection of blood and other biological samples, such as urine, for pharmacokinetic analyses. Pharmacokinetic parameters were measured subsequently. It was observed that upon administering a single 45 mg sublingual dose of DIM to the subjects exposed to DIM, i.e., after 14 days of daily sublingual dosing, the mean Cmax value was about 9 ng/mL. It was also found that upon administering a single 45 mg oral dose of DIM to the subjects exposed to DIM, after 14 days of daily oral dosing, the mean Cmax value of DIM was about 6 ng/mL. The results are illustrated in the plot shown in FIG. 2.

The statistical analyses summary for Cmax and AUC values after single doses are shown in Tables 1 and 2. The peak plasma concentration of DIM was found to be higher after both single and multiple dosing for the sublingual compared to the oral route.

TABLE 1

| parameter | Overall Treatment P-value | Comparison | LS Mean Oral dose | LS Mean Sublingual dose | Difference | 95% Confidence Interval | Contrast P-value |
|---|---|---|---|---|---|---|---|
| Cmax | <.0001 | Single Dose: Oral vs Sublingual | 9.182 | 18.108 | −8.926 | (−11.764, −6.088) | <.0001 |
|  |  | Multiple Dose: Oral vs Sublingual | 5.570 | 8.391 | −2.821 | (−5.711, 0.069) | 0.0555 |

TABLE 2

| parameter | Overall Treatment P-value | Comparison | LS Mean Oral dose | LS Mean Sublingual dose | Difference | 95% Confidence Interval | Contrast P-value |
|---|---|---|---|---|---|---|---|
| $AUC_{0-inf}$ | <.0001 | Single Dose: Oral vs Sublingual | 135.778 | 276.209 | −140.431 | (−184.714, −96.148) | <.0001 |
|  |  | Multiple Dose: Oral vs Sublingual | 106.723 | 127.037 | −20.314 | (−65.236, 24.607) | 0.3670 |

Certain Embodiments

Embodiment 1 provides a method of treating acne in a subject in need thereof comprising administering to the subject a composition comprising substituted or unsubstituted diindolylmethane, wherein the composition is administered by sublingual or buccal route.

Embodiment 2 provides the method of embodiment 1, wherein the composition further comprises a substituted or unsubstituted retinoic acid based component.

Embodiment 3 provides the method of embodiment 2, wherein the retinoic acid based component is Vitamin A.

Embodiment 4 provides the method of any one of embodiments 1-3, wherein the administration by sublingual or buccal route increases the bioavailability of the substituted or unsubstituted diindolylmethane by about 1-fold to about 1000-fold compared to the bioavailability of the substituted or unsubstituted diindolylmethane of a comparative composition administered by oral route at the same delivery dose.

Embodiment 5 provides the method of any one of embodiments 1-3, wherein the administration by sublingual or buccal route increases the bioavailability of the substituted or unsubstituted diindolylmethane by about 1-fold compared to the bioavailability of the substituted or unsubstituted diindolylmethane of a comparative composition administered by oral route at the same delivery dose.

Embodiment 6 provides the method of any one of embodiments 1-3, wherein the administration by sublingual or buccal route increases the bioavailability of the substituted or unsubstituted diindolylmethane by about 2-fold compared to the bioavailability of the substituted or unsubstituted diindolylmethane of a comparative composition administered by oral route at the same delivery dose.

Embodiment 7 provides the method of any one of embodiments 1-3, wherein the administration by sublingual or buccal route increases the bioavailability of the substituted or unsubstituted diindolylmethane by about 3-fold compared to the bioavailability of the substituted or unsubstituted diindolylmethane of a comparative composition administered by oral route at the same delivery dose.

Embodiment 8 provides the method of any one of embodiment 1-3, wherein the administration by sublingual or buccal route increases the bioavailability of the substituted or unsubstituted diindolylmethane by about 4-fold compared to the bioavailability of the substituted or unsubstituted diindolylmethane of a comparative composition administered by oral route at the same delivery dose.

Embodiment 9 provides the method of any one of embodiments 1-3, wherein the administration by sublingual or buccal route increases the bioavailability of the substituted or unsubstituted diindolylmethane by about 5-fold compared to the bioavailability of the substituted or unsubstituted diindolylmethane of a comparative composition administered by oral route at the same delivery dose.

Embodiment 10 provides the method of any one of embodiments 1-3, wherein the administration by sublingual or buccal route increases the bioavailability of the substituted or unsubstituted diindolylmethane by about 10-fold compared to the bioavailability of the substituted or unsubstituted diindolylmethane of a comparative composition administered by oral route at the same delivery dose.

Embodiment 11 provides the method of any one of embodiments 1-3, wherein the administration by sublingual or buccal route increases the bioavailability of the substituted or unsubstituted diindolylmethane by about 20-fold compared to the bioavailability of the substituted or unsubstituted diindolylmethane of a comparative composition administered by oral route at the same delivery dose.

Embodiment 12 provides the method of any one of embodiments 1-3, wherein the administration by sublingual or buccal route increases the bioavailability of the substituted or unsubstituted diindolylmethane by about 30-fold compared to the bioavailability of the substituted or unsubstituted diindolylmethane of a comparative composition administered by oral route at the same delivery dose.

Embodiment 13 provides the method of any one of embodiments 1-3, wherein the administration by sublingual or buccal route increases the bioavailability of the substituted or unsubstituted diindolylmethane by about 40-fold compared to the bioavailability of the substituted or unsubstituted diindolylmethane of a comparative composition administered by oral route at the same delivery dose.

Embodiment 14 provides the method of any one of embodiments 1-3, wherein the administration by sublingual or buccal route increases the bioavailability of the substituted or unsubstituted diindolylmethane by about 50-fold compared to the bioavailability of the substituted or unsubstituted diindolylmethane of a comparative composition administered by oral route at the same delivery dose.

Embodiment 15 provides the method of any one of embodiments 1-3, wherein the administration by sublingual or buccal route increases the bioavailability of the substituted or unsubstituted diindolylmethane by about 60-fold compared to the bioavailability of the substituted or unsubstituted diindolylmethane of a comparative composition administered by oral route at the same delivery dose.

Embodiment 16 provides the method of any one of embodiments 1-3, wherein the administration by sublingual or buccal route increases the bioavailability of the substituted or unsubstituted diindolylmethane by about 70-fold compared to the bioavailability of the substituted or unsubstituted diindolylmethane of a comparative composition administered by oral route at the same delivery dose.

Embodiment 17 provides the method of any one of embodiments 1-3, wherein the administration by sublingual or buccal route increases the bioavailability of the substituted or unsubstituted diindolylmethane by about 80-fold compared to the bioavailability of the substituted or unsubstituted diindolylmethane of a comparative composition administered by oral route at the same delivery dose.

Embodiment 18 provides the method of any one of embodiments 1-3, wherein the administration by sublingual or buccal route increases the bioavailability of the substituted or unsubstituted diindolylmethane by about 100-fold compared to the bioavailability of the substituted or unsubstituted diindolylmethane of a comparative composition administered by oral route at the same delivery dose.

Embodiment 19 provides the method of any one of embodiments 1-3, wherein the administration by sublingual or buccal route increases the bioavailability of the substituted or unsubstituted diindolylmethane by about 200-fold compared to the bioavailability of the substituted or unsubstituted diindolylmethane of a comparative composition administered by oral route at the same delivery dose.

Embodiment 20 provides the method of any one of embodiments 1-3, wherein the administration by sublingual or buccal route increases the bioavailability of the substituted or unsubstituted diindolylmethane by about 300-fold compared to the bioavailability of the substituted or unsubstituted diindolylmethane of a comparative composition administered by oral route at the same delivery dose.

Embodiment 21 provides the method of any one of embodiments 1-3, wherein the administration by sublingual or buccal route increases the bioavailability of the substituted or unsubstituted diindolylmethane by about 400-fold compared to the bioavailability of the substituted or unsubstituted diindolylmethane of a comparative composition administered by oral route at the same delivery dose.

Embodiment 22 provides the method of any one of embodiments 1-3, wherein the administration by sublingual or buccal route increases the bioavailability of the substituted or unsubstituted diindolylmethane by about 500-fold compared to the bioavailability of the substituted or unsubstituted diindolylmethane of a comparative composition administered by oral route at the same delivery dose.

Embodiment 23 provides the method of any one of embodiments 1-3, wherein the administration by sublingual or buccal route increases the bioavailability of the substituted or unsubstituted diindolylmethane by about 600-fold compared to the bioavailability of the substituted or unsubstituted diindolylmethane of a comparative composition administered by oral route at the same delivery dose.

Embodiment 24 provides the method of any one of embodiments 1-3, wherein the administration by sublingual or buccal route increases the bioavailability of the substituted or unsubstituted diindolylmethane by about 700-fold compared to the bioavailability of the substituted or unsubstituted diindolylmethane of a comparative composition administered by oral route at the same delivery dose.

Embodiment 25 provides the method of any one of embodiments 1-3, wherein the administration by sublingual or buccal route increases the bioavailability of the substituted or unsubstituted diindolylmethane by about 800-fold compared to the bioavailability of the substituted or unsubstituted diindolylmethane of a comparative composition administered by oral route at the same delivery dose.

Embodiment 26 provides the method of any one of embodiments 1-3, wherein the administration by sublingual or buccal route increases the bioavailability of the substituted or unsubstituted diindolylmethane by about 900-fold compared to the bioavailability of the substituted or unsubstituted diindolylmethane of a comparative composition administered by oral route at the same delivery dose.

Embodiment 27 provides the method of any one of embodiments 1-3, wherein the administration by sublingual or buccal route increases the bioavailability of the substituted or unsubstituted diindolylmethane by about 1000-fold compared to the bioavailability of the substituted or unsubstituted diindolylmethane of a comparative composition administered by oral route at the same delivery dose.

Embodiment 28 provides the method of any one of embodiments 4-27, wherein the bioavailability of the substituted or unsubstituted diindolylmethane is measured following administration of a dose comprising at least 15 mg of the substituted or unsubstituted diindolylmethane.

Embodiment 29 provides the method of any one of embodiments 1-28, wherein following administration of the composition by sublingual or buccal route the Cmax of the substituted or unsubstituted diindolylmethane in plasma increases by about 1-fold to about 1000-fold compared to the Cmax following administration of a comparative composition by oral route at the same delivery dose.

Embodiment 30 provides the method of any one of embodiments 1-28, wherein following administration of the composition by sublingual or buccal route the Cmax of the substituted or unsubstituted diindolylmethane in plasma increases by about 2-fold compared to the Cmax following administration of a comparative composition by oral route at the same delivery dose.

Embodiment 31 provides the method of any one of embodiments 1-28, wherein following administration of the composition by sublingual or buccal route the Cmax of the substituted or unsubstituted diindolylmethane in plasma increases by about 3-fold compared to the Cmax following administration of a comparative composition by oral route at the same delivery dose.

Embodiment 32 provides the method of any one of embodiments 1-28, wherein following administration of the composition by sublingual or buccal route the Cmax of the substituted or unsubstituted diindolylmethane in plasma increases by about 4-fold compared to the Cmax following administration of a comparative composition by oral route at the same delivery dose.

Embodiment 33 provides the method of any one of embodiments 1-28, wherein following administration of the composition by sublingual or buccal route the Cmax of the substituted or unsubstituted diindolylmethane in plasma increases by about 5-fold compared to the Cmax following administration of a comparative composition by oral route at the same delivery dose.

Embodiment 34 provides the method of any one of embodiments 1-28, wherein following administration of the composition by sublingual or buccal route the Cmax of the substituted or unsubstituted diindolylmethane in plasma increases by about 10-fold compared to the Cmax following administration of a comparative composition by oral route at the same delivery dose.

Embodiment 35 provides the method of any one of embodiments 1-28, wherein following administration of the composition by sublingual or buccal route the Cmax of the substituted or unsubstituted diindolylmethane in plasma increases by about 20-fold compared to the Cmax following administration of a comparative composition by oral route at the same delivery dose.

Embodiment 36 provides the method of any one of embodiments 1-28, wherein following administration of the composition by sublingual or buccal route the Cmax of the substituted or unsubstituted diindolylmethane in plasma increases by about 30-fold compared to the Cmax following administration of a comparative composition by oral route at the same delivery dose.

Embodiment 37 provides the method of any one of embodiments 1-28, wherein following administration of the composition by sublingual or buccal route the Cmax of the substituted or unsubstituted diindolylmethane in plasma increases by about 40-fold compared to the Cmax following administration of a comparative composition by oral route at the same delivery dose.

Embodiment 38 provides the method of any one of embodiments 1-28, wherein following administration of the composition by sublingual or buccal route the Cmax of the substituted or unsubstituted diindolylmethane in plasma increases by about 50-fold compared to the Cmax following administration of a comparative composition by oral route at the same delivery dose.

Embodiment 39 provides the method of any one of embodiments 1-28, wherein following administration of the composition by sublingual or buccal route the Cmax of the substituted or unsubstituted diindolylmethane in plasma increases by about 60-fold compared to the Cmax following administration of a comparative composition by oral route at the same delivery dose.

Embodiment 40 provides the method of any one of embodiments 1-28, wherein following administration of the composition by sublingual or buccal route the Cmax of the substituted or unsubstituted diindolylmethane in plasma increases by about 70-fold compared to the Cmax following administration of a comparative composition by oral route at the same delivery dose.

Embodiment 41 provides the method of any one of embodiments 1-28, wherein following administration of the composition by sublingual or buccal route the Cmax of the substituted or unsubstituted diindolylmethane in plasma increases by about 80-fold compared to the Cmax following administration of a comparative composition by oral route at the same delivery dose.

Embodiment 42 provides the method of any one of embodiments 1-28, wherein following administration of the composition by sublingual or buccal route the Cmax of the substituted or unsubstituted diindolylmethane in plasma increases by about 90-fold compared to the Cmax following administration of a comparative composition by oral route at the same delivery dose.

Embodiment 43 provides the method of any one of embodiments 1-28, wherein following administration of the composition by sublingual or buccal route the Cmax of the substituted or unsubstituted diindolylmethane in plasma increases by about 100-fold compared to the Cmax following administration of a comparative composition by oral route at the same delivery dose.

Embodiment 44 provides the method of any one of embodiments 1-28, wherein following administration of the composition by sublingual or buccal route the Cmax of the substituted or unsubstituted diindolylmethane in plasma increases by about 200-fold compared to the Cmax following administration of a comparative composition by oral route at the same delivery dose.

Embodiment 45 provides the method of any one of embodiments 1-28, wherein following administration of the composition by sublingual or buccal route the Cmax of the substituted or unsubstituted diindolylmethane in plasma increases by about 300-fold compared to the Cmax following administration of a comparative composition by oral route at the same delivery dose.

Embodiment 46 provides the method of any one of embodiments 1-28, wherein following administration of the composition by sublingual or buccal route the Cmax of the substituted or unsubstituted diindolylmethane in plasma increases by about 400-fold compared to the Cmax following administration of a comparative composition by oral route at the same delivery dose.

Embodiment 47 provides the method of any one of embodiments 1-28, wherein following administration of the composition by sublingual or buccal route the Cmax of the substituted or unsubstituted diindolylmethane in plasma increases by about 500-fold compared to the Cmax following administration of a comparative composition by oral route at the same delivery dose.

Embodiment 48 provides the method of any one of embodiments 1-28, wherein following administration of the composition by sublingual or buccal route the Cmax of the substituted or unsubstituted diindolylmethane in plasma increases by about 600-fold compared to the Cmax following administration of a comparative composition by oral route at the same delivery dose.

Embodiment 49 provides the method of any one of embodiments 1-28, wherein following administration of the composition by sublingual or buccal route the Cmax of the substituted or unsubstituted diindolylmethane in plasma increases by about 700-fold compared to the Cmax following administration of a comparative composition by oral route at the same delivery dose.

Embodiment 50 provides the method of any one of embodiments 1-28, wherein following administration of the composition by sublingual or buccal route the Cmax of the substituted or unsubstituted diindolylmethane in plasma increases by about 800-fold compared to the Cmax following administration of a comparative composition by oral route at the same delivery dose.

Embodiment 51 provides the method of any one of embodiments 1-28, wherein following administration of the composition by sublingual or buccal route the Cmax of the substituted or unsubstituted diindolylmethane in plasma increases by about 900-fold compared to the Cmax following administration of a comparative composition by oral route at the same delivery dose.

Embodiment 52 provides the method of any one of embodiments 1-28, wherein following administration of the composition by sublingual or buccal route the Cmax of the substituted or unsubstituted diindolylmethane in plasma increases by about 1000-fold compared to the Cmax following administration of a comparative composition by oral route at the same delivery dose.

Embodiment 53 provides the method of any one of embodiments 29-52, wherein the Cmax of the substituted or unsubstituted diindolylmethane in plasma is measured following administration of a dose comprising at least 15 mg of the substituted or unsubstituted diindolylmethane.

Embodiment 54 provides the method of any one of embodiments 1-53, wherein following administration of the composition by sublingual or buccal route the AUC of the substituted or unsubstituted diindolylmethane in plasma increases by about 1-fold to about 1000-fold compared to the AUC following administration of a comparative composition by oral route at the same delivery dose.

Embodiment 55 provides the method of any one of embodiments 1-53, wherein following administration of the composition by sublingual or buccal route the AUC of the substituted or unsubstituted diindolylmethane in plasma increases by about 2-fold compared to the AUC following administration of a comparative composition by oral route at the same delivery dose.

Embodiment 56 provides the method of any one of embodiments 1-53, wherein following administration of the composition by sublingual or buccal route the AUC of the substituted or unsubstituted diindolylmethane in plasma increases by about 3-fold compared to the AUC following administration of a comparative composition by oral route at the same delivery dose.

Embodiment 57 provides the method of any one of embodiments 1-53, wherein following administration of the composition by sublingual or buccal route the AUC of the substituted or unsubstituted diindolylmethane in plasma increases by about 4-fold compared to the AUC following administration of a comparative composition by oral route at the same delivery dose.

Embodiment 58 provides the method of any one of embodiments 1-53, wherein following administration of the composition by sublingual or buccal route the AUC of the substituted or unsubstituted diindolylmethane in plasma increases by about 5-fold compared to the AUC following administration of a comparative composition by oral route at the same delivery dose.

Embodiment 59 provides the method of any one of embodiments 1-53, wherein following administration of the composition by sublingual or buccal route the AUC of the substituted or unsubstituted diindolylmethane in plasma increases by about 6-fold compared to the AUC following administration of a comparative composition by oral route at the same delivery dose.

Embodiment 60 provides the method of any one of embodiments 1-53, wherein following administration of the composition by sublingual or buccal route the AUC of the substituted or unsubstituted diindolylmethane in plasma increases by about 7-fold compared to the AUC following administration of a comparative composition by oral route at the same delivery dose.

Embodiment 61 provides the method of any one of embodiments 1-53, wherein following administration of the composition by sublingual or buccal route the AUC of the substituted or unsubstituted diindolylmethane in plasma increases by about 8-fold compared to the AUC following administration of a comparative composition by oral route at the same delivery dose.

Embodiment 62 provides the method of any one of embodiments 1-53, wherein following administration of the composition by sublingual or buccal route the AUC of the substituted or unsubstituted diindolylmethane in plasma increases by about 9-fold compared to the AUC following administration of a comparative composition by oral route at the same delivery dose.

Embodiment 63 provides the method of any one of embodiments 1-53, wherein following administration of the composition by sublingual or buccal route the AUC of the substituted or unsubstituted diindolylmethane in plasma increases by about 10-fold compared to the AUC following administration of a comparative composition by oral route at the same delivery dose.

Embodiment 64 provides the method of any one of embodiments 1-53, wherein following administration of the composition by sublingual or buccal route the AUC of the substituted or unsubstituted diindolylmethane in plasma increases by about 20-fold compared to the AUC following administration of a comparative composition by oral route at the same delivery dose.

Embodiment 65 provides the method of any one of embodiments 1-53, wherein following administration of the composition by sublingual or buccal route the AUC of the substituted or unsubstituted diindolylmethane in plasma increases by about 30-fold compared to the AUC following administration of a comparative composition by oral route at the same delivery dose.

Embodiment 66 provides the method of any one of embodiments 1-53, wherein following administration of the composition by sublingual or buccal route the AUC of the substituted or unsubstituted diindolylmethane in plasma increases by about 40-fold compared to the AUC following administration of a comparative composition by oral route at the same delivery dose.

Embodiment 67 provides the method of any one of embodiments 1-53, wherein following administration of the composition by sublingual or buccal route the AUC of the substituted or unsubstituted diindolylmethane in plasma increases by about 50-fold compared to the AUC following administration of a comparative composition by oral route at the same delivery dose.

Embodiment 68 provides the method of any one of embodiments 1-53, wherein following administration of the composition by sublingual or buccal route the AUC of the substituted or unsubstituted diindolylmethane in plasma increases by about 60-fold compared to the AUC following administration of a comparative composition by oral route at the same delivery dose.

Embodiment 69 provides the method of any one of embodiments 1-53, wherein following administration of the composition by sublingual or buccal route the AUC of the substituted or unsubstituted diindolylmethane in plasma increases by about 70-fold compared to the AUC following administration of a comparative composition by oral route at the same delivery dose.

Embodiment 70 provides the method of any one of embodiments 1-53, wherein following administration of the composition by sublingual or buccal route the AUC of the substituted or unsubstituted diindolylmethane in plasma increases by about 80-fold compared to the AUC following administration of a comparative composition by oral route at the same delivery dose.

Embodiment 71 provides the method of any one of embodiments 1-53, wherein following administration of the composition by sublingual or buccal route the AUC of the substituted or unsubstituted diindolylmethane in plasma increases by about 90-fold compared to the AUC following administration of a comparative composition by oral route at the same delivery dose.

Embodiment 72 provides the method of any one of embodiments 1-53, wherein following administration of the composition by sublingual or buccal route the AUC of the substituted or unsubstituted diindolylmethane in plasma increases by about 100-fold compared to the AUC following administration of a comparative composition by oral route at the same delivery dose.

Embodiment 73 provides the method of any one of embodiments 1-53, wherein following administration of the composition by sublingual or buccal route the AUC of the substituted or unsubstituted diindolylmethane in plasma increases by about 200-fold compared to the AUC following administration of a comparative composition by oral route at the same delivery dose.

Embodiment 74 provides the method of any one of embodiments 1-53, wherein following administration of the composition by sublingual or buccal route the AUC of the substituted or unsubstituted diindolylmethane in plasma increases by about 300-fold compared to the AUC following administration of a comparative composition by oral route at the same delivery dose.

Embodiment 75 provides the method of any one of embodiments 1-53, wherein following administration of the composition by sublingual or buccal route the AUC of the substituted or unsubstituted diindolylmethane in plasma increases by about 400-fold compared to the AUC following administration of a comparative composition by oral route at the same delivery dose.

Embodiment 76 provides the method of any one of embodiments 1-53, wherein following administration of the composition by sublingual or buccal route the AUC of the substituted or unsubstituted diindolylmethane in plasma increases by about 500-fold compared to the AUC following administration of a comparative composition by oral route at the same delivery dose.

Embodiment 77 provides the method of any one of embodiments 1-53, wherein following administration of the composition by sublingual or buccal route the AUC of the substituted or unsubstituted diindolylmethane in plasma increases by about 600-fold compared to the AUC following administration of a comparative composition by oral route at the same delivery dose.

Embodiment 78 provides the method of any one of embodiments 1-53, wherein following administration of the composition by sublingual or buccal route the AUC of the substituted or unsubstituted diindolylmethane in plasma increases by about 700-fold compared to the AUC following administration of a comparative composition by oral route at the same delivery dose.

Embodiment 79 provides the method of any one of embodiments 1-53, wherein following administration of the composition by sublingual or buccal route the AUC of the substituted or unsubstituted diindolylmethane in plasma increases by about 800-fold compared to the AUC following administration of a comparative composition by oral route at the same delivery dose.

Embodiment 80 provides the method of any one of embodiments 1-53, wherein following administration of the composition by sublingual or buccal route the AUC of the substituted or unsubstituted diindolylmethane in plasma increases by about 900-fold compared to the AUC following administration of a comparative composition by oral route at the same delivery dose.

Embodiment 81 provides the method of any one of embodiments 1-53, wherein following administration of the composition by sublingual or buccal route the AUC of the substituted or unsubstituted diindolylmethane in plasma increases by about 1000-fold compared to the AUC following administration of a comparative composition by oral route at the same delivery dose.

Embodiment 82 provides the method of any one of embodiments 54-81, wherein the AUC of the substituted or unsubstituted diindolylmethane in plasma is measured following administration of a dose comprising at least 15 mg of the substituted or unsubstituted diindolylmethane.

Embodiment 83 provides the method of any one of embodiments 1-82, wherein following administration of the composition by sublingual or buccal route the Tmax of the substituted or unsubstituted diindolylmethane in plasma decreases by about 1-fold to about 1000-fold compared to the Tmax following administration of a comparative composition by oral route at the same delivery dose.

Embodiment 84 provides the method of any one of embodiments 1-82, wherein following administration of the composition by sublingual or buccal route the Tmax of the substituted or unsubstituted diindolylmethane in plasma decreases by about 1-fold compared to the Tmax following administration of a comparative composition by oral route at the same delivery dose.

Embodiment 85 provides the method of any one of embodiments 1-82, wherein following administration of the composition by sublingual or buccal route the Tmax of the substituted or unsubstituted diindolylmethane in plasma decreases by about 2-fold compared to the Tmax following administration of a comparative composition by oral route at the same delivery dose.

Embodiment 86 provides the method of any one of embodiments 1-82, wherein following administration of the composition by sublingual or buccal route the Tmax of the substituted or unsubstituted diindolylmethane in plasma decreases by about 3-fold compared to the Tmax following administration of a comparative composition by oral route at the same delivery dose.

Embodiment 87 provides the method of any one of embodiments 1-82, wherein following administration of the composition by sublingual or buccal route the Tmax of the substituted or unsubstituted diindolylmethane in plasma decreases by about 4-fold compared to the Tmax following administration of a comparative composition by oral route at the same delivery dose.

Embodiment 88 provides the method of any one of embodiments 1-82, wherein following administration of the composition by sublingual or buccal route the Tmax of the substituted or unsubstituted diindolylmethane in plasma decreases by about 5-fold compared to the Tmax following administration of a comparative composition by oral route at the same delivery dose.

Embodiment 89 provides the method of any one of embodiments 1-82, wherein following administration of the composition by sublingual or buccal route the Tmax of the substituted or unsubstituted diindolylmethane in plasma decreases by about 10-fold compared to the Tmax following administration of a comparative composition by oral route at the same delivery dose.

Embodiment 90 provides the method of any one of embodiments 1-82, wherein following administration of the composition by sublingual or buccal route the Tmax of the substituted or unsubstituted diindolylmethane in plasma decreases by about 20-fold compared to the Tmax following administration of a comparative composition by oral route at the same delivery dose.

Embodiment 91 provides the method of any one of embodiments 1-82, wherein following administration of the composition by sublingual or buccal route the Tmax of the substituted or unsubstituted diindolylmethane in plasma decreases by about 30-fold compared to the Tmax following administration of a comparative composition by oral route at the same delivery dose.

Embodiment 92 provides the method of any one of embodiments 1-82, wherein following administration of the composition by sublingual or buccal route the Tmax of the substituted or unsubstituted diindolylmethane in plasma decreases by about 40-fold compared to the Tmax following administration of a comparative composition by oral route at the same delivery dose.

Embodiment 93 provides the method of any one of embodiments 1-82, wherein following administration of the composition by sublingual or buccal route the Tmax of the substituted or unsubstituted diindolylmethane in plasma decreases by about 50-fold compared to the Tmax following administration of a comparative composition by oral route at the same delivery dose.

Embodiment 94 provides the method of any one of embodiments 1-82, wherein following administration of the composition by sublingual or buccal route the Tmax of the substituted or unsubstituted diindolylmethane in plasma decreases by about 60-fold compared to the Tmax following administration of a comparative composition by oral route at the same delivery dose.

Embodiment 95 provides the method of any one of embodiments 1-82, wherein following administration of the composition by sublingual or buccal route the Tmax of the substituted or unsubstituted diindolylmethane in plasma decreases by about 70-fold compared to the Tmax following administration of a comparative composition by oral route at the same delivery dose.

Embodiment 96 provides the method of any one of embodiments 1-82, wherein following administration of the composition by sublingual or buccal route the Tmax of the substituted or unsubstituted diindolylmethane in plasma decreases by about 80-fold compared to the Tmax following administration of a comparative composition by oral route at the same delivery dose.

Embodiment 97 provides the method of any one of embodiments 1-82, wherein following administration of the composition by sublingual or buccal route the Tmax of the substituted or unsubstituted diindolylmethane in plasma decreases by about 90-fold compared to the Tmax following administration of a comparative composition by oral route at the same delivery dose.

Embodiment 98 provides the method of any one of embodiments 1-82, wherein following administration of the composition by sublingual or buccal route the Tmax of the substituted or unsubstituted diindolylmethane in plasma decreases by about 100-fold compared to the Tmax following administration of a comparative composition by oral route at the same delivery dose.

Embodiment 99 provides the method of any one of embodiments 1-82, wherein following administration of the composition by sublingual or buccal route the Tmax of the substituted or unsubstituted diindolylmethane in plasma decreases by about 200-fold compared to the Tmax following administration of a comparative composition by oral route at the same delivery dose.

Embodiment 100 provides the method of any one of embodiments 1-82, wherein following administration of the composition by sublingual or buccal route the Tmax of the substituted or unsubstituted diindolylmethane in plasma decreases by about 300-fold compared to the Tmax following administration of a comparative composition by oral route at the same delivery dose.

Embodiment 101 provides the method of any one of embodiments 1-82, wherein following administration of the composition by sublingual or buccal route the Tmax of the substituted or unsubstituted diindolylmethane in plasma decreases by about 400-fold compared to the Tmax following administration of a comparative composition by oral route at the same delivery dose.

Embodiment 102 provides the method of any one of embodiments 1-82, wherein following administration of the composition by sublingual or buccal route the Tmax of the substituted or unsubstituted diindolylmethane in plasma decreases by about 500-fold compared to the Tmax following administration of a comparative composition by oral route at the same delivery dose.

Embodiment 103 provides the method of any one of embodiments 1-82, wherein following administration of the composition by sublingual or buccal route the Tmax of the substituted or unsubstituted diindolylmethane in plasma decreases by about 600-fold compared to the Tmax following administration of a comparative composition by oral route at the same delivery dose.

Embodiment 104 provides the method of any one of embodiments 1-82, wherein following administration of the composition by sublingual or buccal route the Tmax of the substituted or unsubstituted diindolylmethane in plasma decreases by about 700-fold compared to the Tmax following administration of a comparative composition by oral route at the same delivery dose.

Embodiment 105 provides the method of any one of embodiments 1-82, wherein following administration of the composition by sublingual or buccal route the Tmax of the substituted or unsubstituted diindolylmethane in plasma decreases by about 800-fold compared to the Tmax following administration of a comparative composition by oral route at the same delivery dose.

Embodiment 106 provides the method of any one of embodiments 1-82, wherein following administration of the composition by sublingual or buccal route the Tmax of the substituted or unsubstituted diindolylmethane in plasma decreases by about 900-fold compared to the Tmax following administration of a comparative composition by oral route at the same delivery dose.

Embodiment 107 provides the method of any one of embodiments 1-82, wherein following administration of the composition by sublingual or buccal route the Tmax of the substituted or unsubstituted diindolylmethane in plasma decreases by about 1000-fold compared to the Tmax following administration of a comparative composition by oral route at the same delivery dose.

Embodiment 108 provides the method of any one of embodiments 83-107, wherein the Tmax of the substituted or unsubstituted diindolylmethane in plasma is measured following administration of a dose comprising at least 15 mg of the substituted or unsubstituted diindolylmethane.

Embodiment 109 provides the method of any one of embodiments 1-108, wherein the percentage of a composition effluxed by P-gp following the sublingual or buccal administration is about 0.1% to about 50% of the percentage of a comparative composition effluxed by P-gp following the oral administration, wherein the sublingual or buccal and oral administrations are at the same delivery dose.

Embodiment 110 provides the method of any one of embodiments 1-108, wherein the percentage of a composition effluxed by P-gp following the sublingual or buccal administration is about 0.1% of the percentage of a comparative composition effluxed by P-gp following the oral administration, wherein the sublingual or buccal and oral administrations are at the same delivery dose.

Embodiment 111 provides the method of any one of embodiments 1-108, wherein the percentage of a composition effluxed by P-gp following the sublingual or buccal administration is about 0.2% of the percentage of a comparative composition effluxed by P-gp following the oral administration, wherein the sublingual or buccal and oral administrations are at the same delivery dose.

Embodiment 112 provides the method of any one of embodiments 1-108, wherein the percentage of a composition effluxed by P-gp following the sublingual or buccal administration is about 0.3% of the percentage of a comparative composition effluxed by P-gp following the oral administration, wherein the sublingual or buccal and oral administrations are at the same delivery dose.

Embodiment 113 provides the method of any one of embodiments 1-108, wherein the percentage of a composition effluxed by P-gp following the sublingual or buccal administration is about 0.4% of the percentage of a comparative composition effluxed by P-gp following the oral administration, wherein the sublingual or buccal and oral administrations are at the same delivery dose.

Embodiment 114 provides the method of any one of embodiments 1-108, wherein the percentage of a composition effluxed by P-gp following the sublingual or buccal administration is about 0.5% of the percentage of a comparative composition effluxed by P-gp following the oral administration, wherein the sublingual or buccal and oral administrations are at the same delivery dose.

Embodiment 115 provides the method of any one of embodiments 1-108, wherein the percentage of a composition effluxed by P-gp following the sublingual or buccal administration is about 1% of the percentage of a comparative composition effluxed by P-gp following the oral administration, wherein the sublingual or buccal and oral administrations are at the same delivery dose.

Embodiment 116 provides the method of any one of embodiments 1-108, wherein the percentage of a composition effluxed by P-gp following the sublingual or buccal administration is about 2% of the percentage of a comparative composition effluxed by P-gp following the oral administration, wherein the sublingual or buccal and oral administrations are at the same delivery dose.

Embodiment 117 provides the method of any one of embodiments 1-108, wherein the percentage of a composition effluxed by P-gp following the sublingual or buccal administration is about 3% of the percentage of a comparative composition effluxed by P-gp following the oral administration, wherein the sublingual or buccal and oral administrations are at the same delivery dose.

Embodiment 118 provides the method of any one of embodiments 1-108, wherein the percentage of a composition effluxed by P-gp following the sublingual or buccal administration is about 4% of the percentage of a comparative composition effluxed by P-gp following the oral administration, wherein the sublingual or buccal and oral administrations are at the same delivery dose.

Embodiment 119 provides the method of any one of embodiments 1-108, wherein the percentage of a composition effluxed by P-gp following the sublingual or buccal administration is about 5% of the percentage of a comparative composition effluxed by P-gp following the oral administration, wherein the sublingual or buccal and oral administrations are at the same delivery dose.

Embodiment 120 provides the method of any one of embodiments 1-108, wherein the percentage of a composition effluxed by P-gp following the sublingual or buccal administration is about 6% of the percentage of a comparative composition effluxed by P-gp following the oral administration, wherein the sublingual or buccal and oral administrations are at the same delivery dose.

Embodiment 121 provides the method of any one of embodiments 1-108, wherein the percentage of a composition effluxed by P-gp following the sublingual or buccal administration is about 7% of the percentage of a comparative composition effluxed by P-gp following the oral administration, wherein the sublingual or buccal and oral administrations are at the same delivery dose.

Embodiment 122 provides the method of any one of embodiments 1-108, wherein the percentage of a composition effluxed by P-gp following the sublingual or buccal administration is about 8% of the percentage of a comparative composition effluxed by P-gp following the oral administration, wherein the sublingual or buccal and oral administrations are at the same delivery dose.

Embodiment 123 provides the method of any one of embodiments 1-108, wherein the percentage of a composition effluxed by P-gp following the sublingual or buccal administration is about 9% of the percentage of a comparative composition effluxed by P-gp following the oral administration, wherein the sublingual or buccal and oral administrations are at the same delivery dose.

Embodiment 124 provides the method of any one of embodiments 1-108, wherein the percentage of a composition effluxed by P-gp following the sublingual or buccal administration is about 10% of the percentage of a comparative composition effluxed by P-gp following the oral administration, wherein the sublingual or buccal and oral administrations are at the same delivery dose.

Embodiment 125 provides the method of any one of embodiments 1-108, wherein the percentage of a composition effluxed by P-gp following the sublingual or buccal administration is about 20% of the percentage of a comparative composition effluxed by P-gp following the oral administration, wherein the sublingual or buccal and oral administrations are at the same delivery dose.

Embodiment 126 provides the method of any one of embodiments 1-108, wherein the percentage of a composition effluxed by P-gp following the sublingual or buccal administration is about 30% of the percentage of a comparative composition effluxed by P-gp following the oral administration, wherein the sublingual or buccal and oral administrations are at the same delivery dose.

Embodiment 127 provides the method of any one of embodiments 1-108, wherein the percentage of a composition effluxed by P-gp following the sublingual or buccal administration is about 40% of the percentage of a comparative composition effluxed by P-gp following the oral administration, wherein the sublingual or buccal and oral administrations are at the same delivery dose.

Embodiment 128 provides the method of any one of embodiments 1-108, wherein the percentage of a composition effluxed by P-gp following the sublingual or buccal administration is about 50% of the percentage of a comparative composition effluxed by P-gp following the oral administration, wherein the sublingual or buccal and oral administrations are at the same delivery dose.

Embodiment 129 provides the method of any one of embodiments 109-128, wherein the percentage of a composition effluxed by P-gp following the sublingual or buccal administration and the percentage of a comparative composition effluxed by P-gp following the oral administration are based on a dosage of administration comprising at least 15 mg of the substituted or unsubstituted diindolylmethane.

Embodiment 130 provides the method of any one of embodiments 1-129, wherein the percentage of a composition influxed by an OATP following the sublingual or buccal administration is about 0.1% to about 50% of the percentage of a comparative composition influxed by an OATP following the oral administration, wherein the sublingual or buccal and oral administrations are at the same delivery dose.

Embodiment 131 provides the method of any one of embodiments 1-129, wherein the percentage of a composition influxed by an OATP following the sublingual or buccal administration is about 0.1% of the percentage of a comparative composition influxed by an OATP following the oral administration, wherein the sublingual or buccal and oral administrations are at the same delivery dose.

Embodiment 132 provides the method of any one of embodiments 1-129, wherein the percentage of a composition influxed by an OATP following the sublingual or buccal administration is about 0.2% of the percentage of a comparative composition influxed by an OATP following the oral administration, wherein the sublingual or buccal and oral administrations are at the same delivery dose.

Embodiment 133 provides the method of any one of embodiments 1-129, wherein the percentage of a composition influxed by an OATP following the sublingual or buccal administration is about 0.3% of the percentage of a comparative composition influxed by an OATP following the oral administration, wherein the sublingual or buccal and oral administrations are at the same delivery dose.

Embodiment 134 provides the method of any one of embodiments 1-129, wherein the percentage of a composition influxed by an OATP following the sublingual or buccal administration is about 0.4% of the percentage of a comparative composition influxed by an OATP following the oral administration, wherein the sublingual or buccal and oral administrations are at the same delivery dose.

Embodiment 135 provides the method of any one of embodiments 1-129, wherein the percentage of a composition influxed by an OATP following the sublingual or buccal administration is about 0.5% of the percentage of a comparative composition influxed by an OATP following the oral administration, wherein the sublingual or buccal and oral administrations are at the same delivery dose.

Embodiment 136 provides the method of any one of embodiments 1-129, wherein the percentage of a composition influxed by an OATP following the sublingual or buccal administration is about 0.6% of the percentage of a comparative composition influxed by an OATP following the oral administration, wherein the sublingual or buccal and oral administrations are at the same delivery dose.

Embodiment 137 provides the method of any one of embodiments 1-129, wherein the percentage of a composition influxed by an OATP following the sublingual or buccal administration is about 0.7% of the percentage of a comparative composition influxed by an OATP following the oral administration, wherein the sublingual or buccal and oral administrations are at the same delivery dose.

Embodiment 138 provides the method of any one of embodiments 1-129, wherein the percentage of a composition influxed by an OATP following the sublingual or buccal administration is about 0.8% of the percentage of a comparative composition influxed by an OATP following the oral administration, wherein the sublingual or buccal and oral administrations are at the same delivery dose.

Embodiment 139 provides the method of any one of embodiments 1-129, wherein the percentage of a composition influxed by an OATP following the sublingual or buccal administration is about 0.9% of the percentage of a comparative composition influxed by an OATP following the oral administration, wherein the sublingual or buccal and oral administrations are at the same delivery dose.

Embodiment 140 provides the method of any one of embodiments 1-129, wherein the percentage of a composition influxed by an OATP following the sublingual or buccal administration is about 1% of the percentage of a comparative composition influxed by an OATP following the oral administration, wherein the sublingual or buccal and oral administrations are at the same delivery dose.

Embodiment 141 provides the method of any one of embodiments 1-129, wherein the percentage of a composition influxed by an OATP following the sublingual or buccal administration is about 2% of the percentage of a comparative composition influxed by an OATP following the oral administration, wherein the sublingual or buccal and oral administrations are at the same delivery dose.

Embodiment 142 provides the method of any one of embodiments 1-129, wherein the percentage of a composition influxed by an OATP following the sublingual or buccal administration is about 3% of the percentage of a comparative composition influxed by an OATP following the oral administration, wherein the sublingual or buccal and oral administrations are at the same delivery dose.

Embodiment 143 provides the method of any one of embodiments 1-129, wherein the percentage of a composition influxed by an OATP following the sublingual or buccal administration is about 4% of the percentage of a comparative composition influxed by an OATP following the oral administration, wherein the sublingual or buccal and oral administrations are at the same delivery dose.

Embodiment 144 provides the method of any one of embodiments 1-129, wherein the percentage of a composition influxed by an OATP following the sublingual or buccal administration is about 5% of the percentage of a comparative composition influxed by an OATP following the oral administration, wherein the sublingual or buccal and oral administrations are at the same delivery dose.

Embodiment 145 provides the method of any one of embodiments 1-129, wherein the percentage of a composition influxed by an OATP following the sublingual or buccal administration is about 6% of the percentage of a comparative composition influxed by an OATP following the oral administration, wherein the sublingual or buccal and oral administrations are at the same delivery dose.

Embodiment 146 provides the method of any one of embodiments 1-129, wherein the percentage of a composition influxed by an OATP following the sublingual or buccal administration is about 7% of the percentage of a comparative composition influxed by an OATP following the oral administration, wherein the sublingual or buccal and oral administrations are at the same delivery dose.

Embodiment 147 provides the method of any one of embodiments 1-129, wherein the percentage of a composition influxed by an OATP following the sublingual or buccal administration is about 8% of the percentage of a comparative composition influxed by an OATP following the oral administration, wherein the sublingual or buccal and oral administrations are at the same delivery dose.

Embodiment 148 provides the method of any one of embodiments 1-129, wherein the percentage of a composition influxed by an OATP following the sublingual or buccal administration is about 9% of the percentage of a comparative composition influxed by an OATP following the oral administration, wherein the sublingual or buccal and oral administrations are at the same delivery dose.

Embodiment 149 provides the method of any one of embodiments 1-129, wherein the percentage of a composition influxed by an OATP following the sublingual or buccal administration is about 10% of the percentage of a comparative composition influxed by an OATP following the oral administration, wherein the sublingual or buccal and oral administrations are at the same delivery dose.

Embodiment 150 provides the method of any one of embodiments 1-129, wherein the percentage of a composition influxed by an OATP following the sublingual or buccal administration is about 20% of the percentage of a comparative composition influxed by an OATP following the oral administration, wherein the sublingual or buccal and oral administrations are at the same delivery dose.

Embodiment 151 provides the method of any one of embodiments 1-129, wherein the percentage of a composition influxed by an OATP following the sublingual or buccal administration is about 30% of the percentage of a comparative composition influxed by an OATP following the oral administration, wherein the sublingual or buccal and oral administrations are at the same delivery dose.

Embodiment 152 provides the method of any one of embodiments 1-129, wherein the percentage of a composition influxed by an OATP following the sublingual or buccal administration is about 40% of the percentage of a comparative composition influxed by an OATP following the oral administration, wherein the sublingual or buccal and oral administrations are at the same delivery dose.

Embodiment 153 provides the method of any one of embodiments 1-129, wherein the percentage of a composition influxed by an OATP following the sublingual or buccal administration is about 50% of the percentage of a comparative composition influxed by an OATP following the oral administration, wherein the sublingual or buccal and oral administrations are at the same delivery dose.

Embodiment 154 provides the method of any one of embodiments 130-153, wherein the percentage of a composition influxed by an OATP following the sublingual or buccal administration and the percentage of a comparative composition influxed by an OATP following the oral administration are based on a dosage of administration comprising at least 15 mg of the substituted or unsubstituted diindolylmethane.

Embodiment 155 provides the method of any one of embodiments 1-154, wherein the percentage of a composition metabolized by CYP3A4, CYP1A2, or CYP2B6, following the sublingual or buccal administration is about 0.1% to about 50% of the percentage of a comparative composition metabolized by CYP3A4, CYP1A2, or CYP2B6, following the oral administration, wherein the sublingual or buccal and oral administrations are at the same delivery dose.

Embodiment 156 provides the method of any one of embodiments 1-154, wherein the percentage of a composition metabolized by CYP3A4, CYP1A2, or CYP2B6, following the sublingual or buccal administration is about 0.1% of the percentage of a comparative composition metabolized by CYP3A4, CYP1A2, or CYP2B6, following the oral administration, wherein the sublingual or buccal and oral administrations are at the same delivery dose.

Embodiment 157 provides the method of any one of embodiments 1-154, wherein the percentage of a composition metabolized by CYP3A4, CYP1A2, or CYP2B6, following the sublingual or buccal administration is about 0.2% of the percentage of a comparative composition metabolized by CYP3A4, CYP1A2, or CYP2B6, following the oral administration, wherein the sublingual or buccal and oral administrations are at the same delivery dose.

Embodiment 158 provides the method of any one of embodiments 1-154, wherein the percentage of a composition metabolized by CYP3A4, CYP1A2, or CYP2B6, following the sublingual or buccal administration is about 0.3% of the percentage of a comparative composition metabolized by CYP3A4, CYP1A2, or CYP2B6, following the oral administration, wherein the sublingual or buccal and oral administrations are at the same delivery dose.

Embodiment 159 provides the method of any one of embodiments 1-154, wherein the percentage of a composition metabolized by CYP3A4, CYP1A2, or CYP2B6, following the sublingual or buccal administration is about 0.4% of the percentage of a comparative composition metabolized by CYP3A4, CYP1A2, or CYP2B6, following the oral administration, wherein the sublingual or buccal and oral administrations are at the same delivery dose.

Embodiment 160 provides the method of any one of embodiments 1-154, wherein the percentage of a composition metabolized by CYP3A4, CYP1A2, or CYP2B6, following the sublingual or buccal administration is about 0.5% of the percentage of a comparative composition metabolized by CYP3A4, CYP1A2, or CYP2B6, following the oral administration, wherein the sublingual or buccal and oral administrations are at the same delivery dose.

Embodiment 161 provides the method of any one of embodiments 1-154, wherein the percentage of a composition metabolized by CYP3A4, CYP1A2, or CYP2B6, following the sublingual or buccal administration is about 0.6% of the percentage of a comparative composition metabolized by CYP3A4, CYP1A2, or CYP2B6, following the oral administration, wherein the sublingual or buccal and oral administrations are at the same delivery dose.

Embodiment 162 provides the method of any one of embodiments 1-154, wherein the percentage of a composition metabolized by CYP3A4, CYP1A2, or CYP2B6, following the sublingual or buccal administration is about 0.7% of the percentage of a comparative composition metabolized by CYP3A4, CYP1A2, or CYP2B6, following the oral administration, wherein the sublingual or buccal and oral administrations are at the same delivery dose.

Embodiment 163 provides the method of any one of embodiments 1-154, wherein the percentage of a composition metabolized by CYP3A4, CYP1A2, or CYP2B6, following the sublingual or buccal administration is about 0.8% of the percentage of a comparative composition metabolized by CYP3A4, CYP1A2, or CYP2B6, following the oral administration, wherein the sublingual or buccal and oral administrations are at the same delivery dose.

Embodiment 164 provides the method of any one of embodiments 1-154, wherein the percentage of a composition metabolized by CYP3A4, CYP1A2, or CYP2B6, following the sublingual or buccal administration is about 0.9% of the percentage of a comparative composition metabolized by CYP3A4, CYP1A2, or CYP2B6, following the oral administration, wherein the sublingual or buccal and oral administrations are at the same delivery dose.

Embodiment 165 provides the method of any one of embodiments 1-154, wherein the percentage of a composition metabolized by CYP3A4, CYP1A2, or CYP2B6, following the sublingual or buccal administration is about 1% of the percentage of a comparative composition metabolized by CYP3A4, CYP1A2, or CYP2B6, following the oral administration, wherein the sublingual or buccal and oral administrations are at the same delivery dose.

Embodiment 166 provides the method of any one of embodiments 1-154, wherein the percentage of a composition metabolized by CYP3A4, CYP1A2, or CYP2B6, following the sublingual or buccal administration is about 2% of the percentage of a comparative composition metabolized by CYP3A4, CYP1A2, or CYP2B6, following the oral administration, wherein the sublingual or buccal and oral administrations are at the same delivery dose.

Embodiment 167 provides the method of any one of embodiments 1-154, wherein the percentage of a composition metabolized by CYP3A4, CYP1A2, or CYP2B6, following the sublingual or buccal administration is about 3% of the percentage of a comparative composition metabolized by CYP3A4, CYP1A2, or CYP2B6, following the oral administration, wherein the sublingual or buccal and oral administrations are at the same delivery dose.

Embodiment 168 provides the method of any one of embodiments 1-154, wherein the percentage of a composition metabolized by CYP3A4, CYP1A2, or CYP2B6, following the sublingual or buccal administration is about 4% of the percentage of a comparative composition metabolized by CYP3A4, CYP1A2, or CYP2B6, following the oral administration, wherein the sublingual or buccal and oral administrations are at the same delivery dose.

Embodiment 169 provides the method of any one of embodiments 1-154, wherein the percentage of a composition metabolized by CYP3A4, CYP1A2, or CYP2B6, following the sublingual or buccal administration is about 5% of the percentage of a comparative composition metabolized by CYP3A4, CYP1A2, or CYP2B6, following the oral administration, wherein the sublingual or buccal and oral administrations are at the same delivery dose.

Embodiment 170 provides the method of any one of embodiments 1-154, wherein the percentage of a composition metabolized by CYP3A4, CYP1A2, or CYP2B6, following the sublingual or buccal administration is about 6% of the percentage of a comparative composition metabolized by CYP3A4, CYP1A2, or CYP2B6, following the oral administration, wherein the sublingual or buccal and oral administrations are at the same delivery dose.

Embodiment 171 provides the method of any one of embodiments 1-154, wherein the percentage of a composition metabolized by CYP3A4, CYP1A2, or CYP2B6, following the sublingual or buccal administration is about 7% of the percentage of a comparative composition metabolized by CYP3A4, CYP1A2, or CYP2B6, following the oral administration, wherein the sublingual or buccal and oral administrations are at the same delivery dose.

Embodiment 172 provides the method of any one of embodiments 1-154, wherein the percentage of a composition metabolized by CYP3A4, CYP1A2, or CYP2B6, following the sublingual or buccal administration is about 8% of the percentage of a comparative composition metabolized by CYP3A4, CYP1A2, or CYP2B6, following the oral administration, wherein the sublingual or buccal and oral administrations are at the same delivery dose.

Embodiment 173 provides the method of any one of embodiments 1-154, wherein the percentage of a composition metabolized by CYP3A4, CYP1A2, or CYP2B6, following the sublingual or buccal administration is about 9% of the percentage of a comparative composition metabolized by CYP3A4, CYP1A2, or CYP2B6, following the oral administration, wherein the sublingual or buccal and oral administrations are at the same delivery dose.

Embodiment 174 provides the method of any one of embodiments 1-154, wherein the percentage of a composition metabolized by CYP3A4, CYP1A2, or CYP2B6, following the sublingual or buccal administration is about 10% of the percentage of a comparative composition metabolized by CYP3A4, CYP1A2, or CYP2B6, following the oral administration, wherein the sublingual or buccal and oral administrations are at the same delivery dose.

Embodiment 175 provides the method of any one of embodiments 1-154, wherein the percentage of a composition metabolized by CYP3A4, CYP1A2, or CYP2B6, following the sublingual or buccal administration is about 20% of the percentage of a comparative composition metabolized by CYP3A4, CYP1A2, or CYP2B6, following the oral administration, wherein the sublingual or buccal and oral administrations are at the same delivery dose.

Embodiment 176 provides the method of any one of embodiments 1-154, wherein the percentage of a composition metabolized by CYP3A4, CYP1A2, or CYP2B6, following the sublingual or buccal administration is about 30% of the percentage of a comparative composition metabolized by CYP3A4, CYP1A2, or CYP2B6, following the oral administration, wherein the sublingual or buccal and oral administrations are at the same delivery dose.

Embodiment 177 provides the method of any one of embodiments 1-154, wherein the percentage of a composition metabolized by CYP3A4, CYP1A2, or CYP2B6, following the sublingual or buccal administration is about 40% of the percentage of a comparative composition metabolized by CYP3A4, CYP1A2, or CYP2B6, following the oral administration, wherein the sublingual or buccal and oral administrations are at the same delivery dose.

Embodiment 178 provides the method of any one of embodiments 1-154, wherein the percentage of a composition metabolized by CYP3A4, CYP1A2, or CYP2B6, following the sublingual or buccal administration is about 50% of the percentage of a comparative composition metabolized by CYP3A4, CYP1A2, or CYP2B6, following the oral administration, wherein the sublingual or buccal and oral administrations are at the same delivery dose.

Embodiment 179 provides the method of any one of embodiments 155-178, wherein the percentage of a composition metabolized by CYP3A4, CYP1A2, or CYP2B6, following the sublingual or buccal administration and the percentage of a comparative composition metabolized by CYP3A4, CYP1A2, or CYP2B6, following the oral administration are based on a dosage of administration comprising at least 15 mg of the substituted or unsubstituted diindolylmethane.

Embodiment 180 provides the method of any one of embodiments 1-179, wherein the composition is administered in a dosage form that disintegrates when placed in the sublingual or buccal cavity.

Embodiment 181 provides a method of treating rosacea in a subject in need thereof comprising administering to the subject a composition comprising substituted or unsubstituted diindolylmethane, wherein the composition is administered by sublingual or buccal route.

Embodiment 182 provides the method of claim 181, wherein the composition further comprises a substituted or unsubstituted retinoic acid based component.

Embodiment 183 provides the method of claim 182, wherein the retinoic acid based component is Vitamin A.

Embodiment 184 provides the method of any one of embodiments 181-183, wherein the administration by sublingual or buccal route increases the bioavailability of the substituted or unsubstituted diindolylmethane by about 1-fold to about 1000-fold compared to the bioavailability of the substituted or unsubstituted diindolylmethane of a comparative composition administered by oral route at the same delivery dose.

Embodiment 185 provides the method of any one of embodiments 181-184, wherein the administration by sublingual or buccal route increases the bioavailability of the substituted or unsubstituted diindolylmethane by about 1-fold compared to the bioavailability of the substituted or unsubstituted diindolylmethane of a comparative composition administered by oral route at the same delivery dose.

Embodiment 186 provides the method of any one of embodiments 181-184, wherein the administration by sublingual or buccal route increases the bioavailability of the substituted or unsubstituted diindolylmethane by about 2-fold compared to the bioavailability of the substituted or unsubstituted diindolylmethane of a comparative composition administered by oral route at the same delivery dose.

Embodiment 187 provides the method of any one of embodiments 181-184, wherein the administration by sublingual or buccal route increases the bioavailability of the substituted or unsubstituted diindolylmethane by about 3-fold compared to the bioavailability of the substituted or unsubstituted diindolylmethane of a comparative composition administered by oral route at the same delivery dose.

Embodiment 188 provides the method of any one of embodiments 181-184, wherein the administration by sublingual or buccal route increases the bioavailability of the substituted or unsubstituted diindolylmethane by about 4-fold compared to the bioavailability of the substituted or unsubstituted diindolylmethane of a comparative composition administered by oral route at the same delivery dose.

Embodiment 189 provides the method of any one of embodiments 181-184, wherein the administration by sublingual or buccal route increases the bioavailability of the substituted or unsubstituted diindolylmethane by about 5-fold compared to the bioavailability of the substituted or unsubstituted diindolylmethane of a comparative composition administered by oral route at the same delivery dose.

Embodiment 190 provides the method of any one of embodiments 181-184, wherein the administration by sublingual or buccal route increases the bioavailability of the substituted or unsubstituted diindolylmethane by about 10-fold compared to the bioavailability of the substituted or unsubstituted diindolylmethane of a comparative composition administered by oral route at the same delivery dose.

Embodiment 191 provides the method of any one of embodiments 181-184, wherein the administration by sublingual or buccal route increases the bioavailability of the substituted or unsubstituted diindolylmethane by about 20-fold compared to the bioavailability of the substituted or unsubstituted diindolylmethane of a comparative composition administered by oral route at the same delivery dose.

Embodiment 192 provides the method of any one of embodiments 181-184, wherein the administration by sublingual or buccal route increases the bioavailability of the substituted or unsubstituted diindolylmethane by about 30-fold compared to the bioavailability of the substituted or unsubstituted diindolylmethane of a comparative composition administered by oral route at the same delivery dose.

Embodiment 193 provides the method of any one of embodiments 181-184, wherein the administration by sublingual or buccal route increases the bioavailability of the substituted or unsubstituted diindolylmethane by about 40-fold compared to the bioavailability of the substituted or unsubstituted diindolylmethane of a comparative composition administered by oral route at the same delivery dose.

Embodiment 194 provides the method of any one of embodiments 181-184, wherein the administration by sublingual or buccal route increases the bioavailability of the substituted or unsubstituted diindolylmethane by about 50-fold compared to the bioavailability of the substituted or unsubstituted diindolylmethane of a comparative composition administered by oral route at the same delivery dose.

Embodiment 195 provides the method of any one of embodiments 181-184, wherein the administration by sublingual or buccal route increases the bioavailability of the substituted or unsubstituted diindolylmethane by about 60-fold compared to the bioavailability of the substituted or unsubstituted diindolylmethane of a comparative composition administered by oral route at the same delivery dose.

Embodiment 196 provides the method of any one of embodiments 181-184, wherein the administration by sublingual or buccal route increases the bioavailability of the substituted or unsubstituted diindolylmethane by about 70-fold compared to the bioavailability of the substituted or unsubstituted diindolylmethane of a comparative composition administered by oral route at the same delivery dose.

Embodiment 197 provides the method of any one of embodiments 181-184, wherein the administration by sublingual or buccal route increases the bioavailability of the substituted or unsubstituted diindolylmethane by about 80-fold compared to the bioavailability of the substituted or unsubstituted diindolylmethane of a comparative composition administered by oral route at the same delivery dose.

Embodiment 198 provides the method of any one of embodiments 181-184, wherein the administration by sublingual or buccal route increases the bioavailability of the substituted or unsubstituted diindolylmethane by about 100-fold compared to the bioavailability of the substituted or unsubstituted diindolylmethane of a comparative composition administered by oral route at the same delivery dose.

Embodiment 199 provides the method of any one of embodiments 181-184, wherein the administration by sublingual or buccal route increases the bioavailability of the substituted or unsubstituted diindolylmethane by about 200-fold compared to the bioavailability of the substituted or unsubstituted diindolylmethane of a comparative composition administered by oral route at the same delivery dose.

Embodiment 200 provides the method of any one of embodiments 181-184, wherein the administration by sublingual or buccal route increases the bioavailability of the substituted or unsubstituted diindolylmethane by about 300-fold compared to the bioavailability of the substituted or unsubstituted diindolylmethane of a comparative composition administered by oral route at the same delivery dose.

Embodiment 201 provides the method of any one of embodiments 181-184, wherein the administration by sublingual or buccal route increases the bioavailability of the substituted or unsubstituted diindolylmethane by about 400-fold compared to the bioavailability of the substituted or unsubstituted diindolylmethane of a comparative composition administered by oral route at the same delivery dose.

Embodiment 202 provides the method of any one of embodiments 181-184, wherein the administration by sublingual or buccal route increases the bioavailability of the substituted or unsubstituted diindolylmethane by about 500-fold compared to the bioavailability of the substituted or unsubstituted diindolylmethane of a comparative composition administered by oral route at the same delivery dose.

Embodiment 203 provides the method of any one of embodiments 181-184, wherein the administration by sublingual or buccal route increases the bioavailability of the substituted or unsubstituted diindolylmethane by about 600-fold compared to the bioavailability of the substituted or unsubstituted diindolylmethane of a comparative composition administered by oral route at the same delivery dose.

Embodiment 204 provides the method of any one of embodiments 181-184, wherein the administration by sublingual or buccal route increases the bioavailability of the substituted or unsubstituted diindolylmethane by about 700-fold compared to the bioavailability of the substituted or unsubstituted diindolylmethane of a comparative composition administered by oral route at the same delivery dose.

Embodiment 205 provides the method of any one of embodiments 181-184, wherein the administration by sublingual or buccal route increases the bioavailability of the substituted or unsubstituted diindolylmethane by about 800-fold compared to the bioavailability of the substituted or unsubstituted diindolylmethane of a comparative composition administered by oral route at the same delivery dose.

Embodiment 206 provides the method of any one of embodiments 181-184, wherein the administration by sublingual or buccal route increases the bioavailability of the substituted or unsubstituted diindolylmethane by about 900-fold compared to the bioavailability of the substituted or unsubstituted diindolylmethane of a comparative composition administered by oral route at the same delivery dose.

Embodiment 207 provides the method of any one of embodiments 181-184, wherein the administration by sublingual or buccal route increases the bioavailability of the substituted or unsubstituted diindolylmethane by about 1000-fold compared to the bioavailability of the substituted or unsubstituted diindolylmethane of a comparative composition administered by oral route at the same delivery dose.

Embodiment 208 provides the method of any one of embodiments 185-207, wherein the bioavailability of the substituted or unsubstituted diindolylmethane is measured following administration of a dose comprising at least 15 mg of the substituted or unsubstituted diindolylmethane.

Embodiment 209 provides the method of any one of embodiments 181-208, wherein following administration of the composition by sublingual or buccal route the Cmax of the substituted or unsubstituted diindolylmethane in plasma increases by about 1-fold to about 1000-fold compared to the Cmax following administration of a comparative composition by oral route at the same delivery dose.

Embodiment 210 provides the method of any one of embodiments 181-208, wherein following administration of the composition by sublingual or buccal route the Cmax of the substituted or unsubstituted diindolylmethane in plasma increases by about 2-fold compared to the Cmax following administration of a comparative composition by oral route at the same delivery dose.

Embodiment 211 provides the method of any one of embodiments 181-208, wherein following administration of the composition by sublingual or buccal route the Cmax of the substituted or unsubstituted diindolylmethane in plasma increases by about 3-fold compared to the Cmax following administration of a comparative composition by oral route at the same delivery dose.

Embodiment 212 provides the method of any one of embodiments 181-208, wherein following administration of the composition by sublingual or buccal route the Cmax of the substituted or unsubstituted diindolylmethane in plasma increases by about 4-fold compared to the Cmax following administration of a comparative composition by oral route at the same delivery dose.

Embodiment 213 provides the method of any one of embodiments 181-208, wherein following administration of the composition by sublingual or buccal route the Cmax of the substituted or unsubstituted diindolylmethane in plasma increases by about 5-fold compared to the Cmax following administration of a comparative composition by oral route at the same delivery dose.

Embodiment 214 provides the method of any one of embodiments 181-208, wherein following administration of the composition by sublingual or buccal route the Cmax of the substituted or unsubstituted diindolylmethane in plasma increases by about 10-fold compared to the Cmax following administration of a comparative composition by oral route at the same delivery dose.

Embodiment 215 provides the method of any one of embodiments 181-208, wherein following administration of the composition by sublingual or buccal route the Cmax of the substituted or unsubstituted diindolylmethane in plasma increases by about 20-fold compared to the Cmax following administration of a comparative composition by oral route at the same delivery dose.

Embodiment 216 provides the method of any one of embodiments 181-208, wherein following administration of the composition by sublingual or buccal route the Cmax of the substituted or unsubstituted diindolylmethane in plasma increases by about 30-fold compared to the Cmax following administration of a comparative composition by oral route at the same delivery dose.

Embodiment 217 provides the method of any one of embodiments 181-208, wherein following administration of the composition by sublingual or buccal route the Cmax of the substituted or unsubstituted diindolylmethane in plasma increases by about 40-fold compared to the Cmax following administration of a comparative composition by oral route at the same delivery dose.

Embodiment 218 provides the method of any one of embodiments 181-208, wherein following administration of the composition by sublingual or buccal route the Cmax of the substituted or unsubstituted diindolylmethane in plasma increases by about 50-fold compared to the Cmax following administration of a comparative composition by oral route at the same delivery dose.

Embodiment 219 provides the method of any one of embodiments 181-208, wherein following administration of the composition by sublingual or buccal route the Cmax of the substituted or unsubstituted diindolylmethane in plasma increases by about 60-fold compared to the Cmax following administration of a comparative composition by oral route at the same delivery dose.

Embodiment 220 provides the method of any one of embodiments 181-208, wherein following administration of the composition by sublingual or buccal route the Cmax of the substituted or unsubstituted diindolylmethane in plasma increases by about 70-fold compared to the Cmax following administration of a comparative composition by oral route at the same delivery dose.

Embodiment 221 provides the method of any one of embodiments 181-208, wherein following administration of the composition by sublingual or buccal route the Cmax of the substituted or unsubstituted diindolylmethane in plasma increases by about 80-fold compared to the Cmax following administration of a comparative composition by oral route at the same delivery dose.

Embodiment 222 provides the method of any one of embodiments 181-208, wherein following administration of the composition by sublingual or buccal route the Cmax of the substituted or unsubstituted diindolylmethane in plasma increases by about 90-fold compared to the Cmax following administration of a comparative composition by oral route at the same delivery dose.

Embodiment 223 provides the method of any one of embodiments 181-208, wherein following administration of the composition by sublingual or buccal route the Cmax of the substituted or unsubstituted diindolylmethane in plasma increases by about 100-fold compared to the Cmax following administration of a comparative composition by oral route at the same delivery dose.

Embodiment 224 provides the method of any one of embodiments 181-208, wherein following administration of the composition by sublingual or buccal route the Cmax of the substituted or unsubstituted diindolylmethane in plasma increases by about 200-fold compared to the Cmax following administration of a comparative composition by oral route at the same delivery dose.

Embodiment 225 provides the method of any one of embodiments 181-208, wherein following administration of the composition by sublingual or buccal route the Cmax of the substituted or unsubstituted diindolylmethane in plasma increases by about 300-fold compared to the Cmax following administration of a comparative composition by oral route at the same delivery dose.

Embodiment 226 provides the method of any one of embodiments 181-208, wherein following administration of the composition by sublingual or buccal route the Cmax of the substituted or unsubstituted diindolylmethane in plasma increases by about 400-fold compared to the Cmax following administration of a comparative composition by oral route at the same delivery dose.

Embodiment 227 provides the method of any one of embodiments 181-208, wherein following administration of the composition by sublingual or buccal route the Cmax of the substituted or unsubstituted diindolylmethane in plasma increases by about 500-fold compared to the Cmax following administration of a comparative composition by oral route at the same delivery dose.

Embodiment 228 provides the method of any one of embodiments 181-208, wherein following administration of the composition by sublingual or buccal route the Cmax of the substituted or unsubstituted diindolylmethane in plasma increases by about 600-fold compared to the Cmax following administration of a comparative composition by oral route at the same delivery dose.

Embodiment 229 provides the method of any one of embodiments 181-208, wherein following administration of the composition by sublingual or buccal route the Cmax of the substituted or unsubstituted diindolylmethane in plasma increases by about 700-fold compared to the Cmax following administration of a comparative composition by oral route at the same delivery dose.

Embodiment 230 provides the method of any one of embodiments 181-208, wherein following administration of the composition by sublingual or buccal route the Cmax of the substituted or unsubstituted diindolylmethane in plasma increases by about 800-fold compared to the Cmax following administration of a comparative composition by oral route at the same delivery dose.

Embodiment 231 provides the method of any one of embodiments 181-208, wherein following administration of the composition by sublingual or buccal route the Cmax of the substituted or unsubstituted diindolylmethane in plasma increases by about 900-fold compared to the Cmax following administration of a comparative composition by oral route at the same delivery dose.

Embodiment 232 provides the method of any one of embodiments 181-208, wherein following administration of the composition by sublingual or buccal route the Cmax of the substituted or unsubstituted diindolylmethane in plasma increases by about 1000-fold compared to the Cmax following administration of a comparative composition by oral route at the same delivery dose.

Embodiment 233 provides the method of any one of embodiments 209-232, wherein the Cmax of the substituted or unsubstituted diindolylmethane in plasma is measured following administration of a dose comprising at least 15 mg of the substituted or unsubstituted diindolylmethane.

Embodiment 234 provides the method of any one of embodiments 181-233, wherein following administration of the composition by sublingual or buccal route the AUC of the substituted or unsubstituted diindolylmethane in plasma increases by about 1-fold to about 1000-fold compared to the AUC following administration of a comparative composition by oral route at the same delivery dose.

Embodiment 235 provides the method of any one of embodiments 181-233, wherein following administration of the composition by sublingual or buccal route the AUC of the substituted or unsubstituted diindolylmethane in plasma increases by about 2-fold compared to the AUC following administration of a comparative composition by oral route at the same delivery dose.

Embodiment 236 provides the method of any one of embodiments 181-233, wherein following administration of the composition by sublingual or buccal route the AUC of the substituted or unsubstituted diindolylmethane in plasma increases by about 3-fold compared to the AUC following administration of a comparative composition by oral route at the same delivery dose.

Embodiment 237 provides the method of any one of embodiments 181-233, wherein following administration of the composition by sublingual or buccal route the AUC of the substituted or unsubstituted diindolylmethane in plasma increases by about 4-fold compared to the AUC following administration of a comparative composition by oral route at the same delivery dose.

Embodiment 238 provides the method of any one of embodiments 181-233, wherein following administration of the composition by sublingual or buccal route the AUC of the substituted or unsubstituted diindolylmethane in plasma increases by about 5-fold compared to the AUC following administration of a comparative composition by oral route at the same delivery dose.

Embodiment 239 provides the method of any one of embodiments 181-233, wherein following administration of the composition by sublingual or buccal route the AUC of the substituted or unsubstituted diindolylmethane in plasma increases by about 6-fold compared to the AUC following administration of a comparative composition by oral route at the same delivery dose.

Embodiment 240 provides the method of any one of embodiments 181-233, wherein following administration of the composition by sublingual or buccal route the AUC of the substituted or unsubstituted diindolylmethane in plasma increases by about 7-fold compared to the AUC following administration of a comparative composition by oral route at the same delivery dose.

Embodiment 241 provides the method of any one of embodiments 181-233, wherein following administration of the composition by sublingual or buccal route the AUC of the substituted or unsubstituted diindolylmethane in plasma increases by about 8-fold compared to the AUC following administration of a comparative composition by oral route at the same delivery dose.

Embodiment 242 provides the method of any one of embodiments 181-233, wherein following administration of the composition by sublingual or buccal route the AUC of the substituted or unsubstituted diindolylmethane in plasma increases by about 9-fold compared to the AUC following administration of a comparative composition by oral route at the same delivery dose.

Embodiment 243 provides the method of any one of embodiments 181-233, wherein following administration of the composition by sublingual or buccal route the AUC of the substituted or unsubstituted diindolylmethane in plasma increases by about 10-fold compared to the AUC following administration of a comparative composition by oral route at the same delivery dose.

Embodiment 244 provides the method of any one of embodiments 181-233, wherein following administration of the composition by sublingual or buccal route the AUC of the substituted or unsubstituted diindolylmethane in plasma increases by about 20-fold compared to the AUC following administration of a comparative composition by oral route at the same delivery dose.

Embodiment 245 provides the method of any one of embodiments 181-233, wherein following administration of the composition by sublingual or buccal route the AUC of the substituted or unsubstituted diindolylmethane in plasma increases by about 30-fold compared to the AUC following administration of a comparative composition by oral route at the same delivery dose.

Embodiment 246 provides the method of any one of embodiments 181-233, wherein following administration of the composition by sublingual or buccal route the AUC of the substituted or unsubstituted diindolylmethane in plasma increases by about 40-fold compared to the AUC following administration of a comparative composition by oral route at the same delivery dose.

Embodiment 247 provides the method of any one of embodiments 181-233, wherein following administration of the composition by sublingual or buccal route the AUC of the substituted or unsubstituted diindolylmethane in plasma increases by about 50-fold compared to the AUC following administration of a comparative composition by oral route at the same delivery dose.

Embodiment 248 provides the method of any one of embodiments 181-233, wherein following administration of the composition by sublingual or buccal route the AUC of the substituted or unsubstituted diindolylmethane in plasma increases by about 60-fold compared to the AUC following administration of a comparative composition by oral route at the same delivery dose.

Embodiment 249 provides the method of any one of embodiments 181-233, wherein following administration of the composition by sublingual or buccal route the AUC of the substituted or unsubstituted diindolylmethane in plasma increases by about 70-fold compared to the AUC following administration of a comparative composition by oral route at the same delivery dose.

Embodiment 250 provides the method of any one of embodiments 181-233, wherein following administration of the composition by sublingual or buccal route the AUC of the substituted or unsubstituted diindolylmethane in plasma increases by about 80-fold compared to the AUC following administration of a comparative composition by oral route at the same delivery dose.

Embodiment 251 provides the method of any one of embodiments 181-233, wherein following administration of the composition by sublingual or buccal route the AUC of the substituted or unsubstituted diindolylmethane in plasma increases by about 90-fold compared to the AUC following administration of a comparative composition by oral route at the same delivery dose.

Embodiment 252 provides the method of any one of embodiments 181-233, wherein following administration of the composition by sublingual or buccal route the AUC of the substituted or unsubstituted diindolylmethane in plasma increases by about 100-fold compared to the AUC following administration of a comparative composition by oral route at the same delivery dose.

Embodiment 253 provides the method of any one of embodiments 181-233, wherein following administration of the composition by sublingual or buccal route the AUC of the substituted or unsubstituted diindolylmethane in plasma increases by about 200-fold compared to the AUC following administration of a comparative composition by oral route at the same delivery dose.

Embodiment 254 provides the method of any one of embodiments 181-233, wherein following administration of the composition by sublingual or buccal route the AUC of the substituted or unsubstituted diindolylmethane in plasma increases by about 300-fold compared to the AUC following administration of a comparative composition by oral route at the same delivery dose.

Embodiment 255 provides the method of any one of embodiments 181-233, wherein following administration of the composition by sublingual or buccal route the AUC of the substituted or unsubstituted diindolylmethane in plasma increases by about 400-fold compared to the AUC following administration of a comparative composition by oral route at the same delivery dose.

Embodiment 256 provides the method of any one of embodiments 181-233, wherein following administration of the composition by sublingual or buccal route the AUC of the substituted or unsubstituted diindolylmethane in plasma increases by about 500-fold compared to the AUC following administration of a comparative composition by oral route at the same delivery dose.

Embodiment 257 provides the method of any one of embodiments 181-233, wherein following administration of the composition by sublingual or buccal route the AUC of the substituted or unsubstituted diindolylmethane in plasma increases by about 600-fold compared to the AUC following administration of a comparative composition by oral route at the same delivery dose.

Embodiment 258 provides the method of any one of embodiments 181-233, wherein following administration of the composition by sublingual or buccal route the AUC of the substituted or unsubstituted diindolylmethane in plasma increases by about 700-fold compared to the AUC following administration of a comparative composition by oral route at the same delivery dose.

Embodiment 259 provides the method of any one of embodiments 181-233, wherein following administration of the composition by sublingual or buccal route the AUC of the substituted or unsubstituted diindolylmethane in plasma increases by about 800-fold compared to the AUC following administration of a comparative composition by oral route at the same delivery dose.

Embodiment 260 provides the method of any one of embodiments 181-233, wherein following administration of the composition by sublingual or buccal route the AUC of the substituted or unsubstituted diindolylmethane in plasma increases by about 900-fold compared to the AUC following administration of a comparative composition by oral route at the same delivery dose.

Embodiment 261 provides the method of any one of embodiments 181-233, wherein following administration of the composition by sublingual or buccal route the AUC of the substituted or unsubstituted diindolylmethane in plasma increases by about 1000-fold compared to the AUC following administration of a comparative composition by oral route at the same delivery dose.

Embodiment 262 provides the method of any one of embodiments 234-261, wherein the AUC of the substituted or unsubstituted diindolylmethane in plasma is measured following administration of a dose comprising at least 15 mg of the substituted or unsubstituted diindolylmethane.

Embodiment 263 provides the method of any one of embodiments 181-262, wherein following administration of the composition by sublingual or buccal route the Tmax of the substituted or unsubstituted diindolylmethane in plasma decreases by about 1-fold to about 1000-fold compared to the Tmax following administration of a comparative composition by oral route at the same delivery dose.

Embodiment 264 provides the method of any one of embodiments 181-262, wherein following administration of the composition by sublingual or buccal route the Tmax of the substituted or unsubstituted diindolylmethane in plasma decreases by about 1-fold compared to the Tmax following administration of a comparative composition by oral route at the same delivery dose.

Embodiment 265 provides the method of any one of embodiments 181-262, wherein following administration of the composition by sublingual or buccal route the Tmax of the substituted or unsubstituted diindolylmethane in plasma decreases by about 2-fold compared to the Tmax following administration of a comparative composition by oral route at the same delivery dose.

Embodiment 266 provides the method of any one of embodiments 181-262, wherein following administration of the composition by sublingual or buccal route the Tmax of the substituted or unsubstituted diindolylmethane in plasma decreases by about 3-fold compared to the Tmax following administration of a comparative composition by oral route at the same delivery dose.

Embodiment 267 provides the method of any one of embodiments 181-262, wherein following administration of the composition by sublingual or buccal route the Tmax of the substituted or unsubstituted diindolylmethane in plasma decreases by about 4-fold compared to the Tmax following administration of a comparative composition by oral route at the same delivery dose.

Embodiment 268 provides the method of any one of embodiments 181-262, wherein following administration of the composition by sublingual or buccal route the Tmax of the substituted or unsubstituted diindolylmethane in plasma decreases by about 5-fold compared to the Tmax following administration of a comparative composition by oral route at the same delivery dose.

Embodiment 269 provides the method of any one of embodiments 181-262, wherein following administration of the composition by sublingual or buccal route the Tmax of the substituted or unsubstituted diindolylmethane in plasma decreases by about 10-fold compared to the Tmax following administration of a comparative composition by oral route at the same delivery dose.

Embodiment 270 provides the method of any one of embodiments 181-262, wherein following administration of the composition by sublingual or buccal route the Tmax of the substituted or unsubstituted diindolylmethane in plasma decreases by about 20-fold compared to the Tmax following administration of a comparative composition by oral route at the same delivery dose.

Embodiment 271 provides the method of any one of embodiments 181-262, wherein following administration of the composition by sublingual or buccal route the Tmax of the substituted or unsubstituted diindolylmethane in plasma decreases by about 30-fold compared to the Tmax following administration of a comparative composition by oral route at the same delivery dose.

Embodiment 272 provides the method of any one of embodiments 181-262, wherein following administration of the composition by sublingual or buccal route the Tmax of the substituted or unsubstituted diindolylmethane in plasma decreases by about 40-fold compared to the Tmax following administration of a comparative composition by oral route at the same delivery dose.

Embodiment 273 provides the method of any one of embodiments 181-262, wherein following administration of the composition by sublingual or buccal route the Tmax of the substituted or unsubstituted diindolylmethane in plasma decreases by about 50-fold compared to the Tmax following administration of a comparative composition by oral route at the same delivery dose.

Embodiment 274 provides the method of any one of embodiments 181-262, wherein following administration of the composition by sublingual or buccal route the Tmax of the substituted or unsubstituted diindolylmethane in plasma decreases by about 60-fold compared to the Tmax following administration of a comparative composition by oral route at the same delivery dose.

Embodiment 275 provides the method of any one of embodiments 181-262, wherein following administration of the composition by sublingual or buccal route the Tmax of the substituted or unsubstituted diindolylmethane in plasma decreases by about 70-fold compared to the Tmax following administration of a comparative composition by oral route at the same delivery dose.

Embodiment 276 provides the method of any one of embodiments 181-262, wherein following administration of the composition by sublingual or buccal route the Tmax of the substituted or unsubstituted diindolylmethane in plasma decreases by about 80-fold compared to the Tmax following administration of a comparative composition by oral route at the same delivery dose.

Embodiment 277 provides the method of any one of embodiments 181-262, wherein following administration of the composition by sublingual or buccal route the Tmax of the substituted or unsubstituted diindolylmethane in plasma decreases by about 90-fold compared to the Tmax following administration of a comparative composition by oral route at the same delivery dose.

Embodiment 278 provides the method of any one of embodiments 181-262, wherein following administration of the composition by sublingual or buccal route the Tmax of the substituted or unsubstituted diindolylmethane in plasma decreases by about 100-fold compared to the Tmax following administration of a comparative composition by oral route at the same delivery dose.

Embodiment 279 provides the method of any one of embodiments 181-262, wherein following administration of the composition by sublingual or buccal route the Tmax of the substituted or unsubstituted diindolylmethane in plasma decreases by about 200-fold compared to the Tmax following administration of a comparative composition by oral route at the same delivery dose.

Embodiment 280 provides the method of any one of embodiments 181-262, wherein following administration of the composition by sublingual or buccal route the Tmax of the substituted or unsubstituted diindolylmethane in plasma decreases by about 300-fold compared to the Tmax following administration of a comparative composition by oral route at the same delivery dose.

Embodiment 281 provides the method of any one of embodiments 181-262, wherein following administration of the composition by sublingual or buccal route the Tmax of the substituted or unsubstituted diindolylmethane in plasma decreases by about 400-fold compared to the Tmax following administration of a comparative composition by oral route at the same delivery dose.

Embodiment 282 provides the method of any one of embodiments 181-262, wherein following administration of the composition by sublingual or buccal route the Tmax of the substituted or unsubstituted diindolylmethane in plasma decreases by about 500-fold compared to the Tmax following administration of a comparative composition by oral route at the same delivery dose.

Embodiment 283 provides the method of any one of embodiments 181-262, wherein following administration of the composition by sublingual or buccal route the Tmax of the substituted or unsubstituted diindolylmethane in plasma decreases by about 600-fold compared to the Tmax following administration of a comparative composition by oral route at the same delivery dose.

Embodiment 284 provides the method of any one of embodiments 181-262, wherein following administration of the composition by sublingual or buccal route the Tmax of the substituted or unsubstituted diindolylmethane in plasma decreases by about 700-fold compared to the Tmax following administration of a comparative composition by oral route at the same delivery dose.

Embodiment 285 provides the method of any one of embodiments 181-262, wherein following administration of the composition by sublingual or buccal route the Tmax of the substituted or unsubstituted diindolylmethane in plasma decreases by about 800-fold compared to the Tmax following administration of a comparative composition by oral route at the same delivery dose.

Embodiment 286 provides the method of any one of embodiments 181-262, wherein following administration of the composition by sublingual or buccal route the Tmax of the substituted or unsubstituted diindolylmethane in plasma decreases by about 900-fold compared to the Tmax following administration of a comparative composition by oral route at the same delivery dose.

Embodiment 287 provides the method of any one of embodiments 181-262, wherein following administration of the composition by sublingual or buccal route the Tmax of the substituted or unsubstituted diindolylmethane in plasma decreases by about 1000-fold compared to the Tmax following administration of a comparative composition by oral route at the same delivery dose.

Embodiment 288 provides the method of any one of embodiments 263-287, wherein the Tmax of the substituted or unsubstituted diindolylmethane in plasma is measured following administration of a dose comprising at least 15 mg of the substituted or unsubstituted diindolylmethane.

Embodiment 289 provides the method of any one of embodiments 181-288, wherein the percentage of a composition effluxed by P-gp following the sublingual or buccal administration is about 0.1% to about 50% of the percentage of a comparative composition effluxed by P-gp following the oral administration, wherein the sublingual or buccal and oral administrations are at the same delivery dose.

Embodiment 290 provides the method of any one of embodiments 181-288, wherein the percentage of a composition effluxed by P-gp following the sublingual or buccal administration is about 0.1% of the percentage of a comparative composition effluxed by P-gp following the oral administration, wherein the sublingual or buccal and oral administrations are at the same delivery dose.

Embodiment 291 provides the method of any one of embodiments 181-288, wherein the percentage of a composition effluxed by P-gp following the sublingual or buccal administration is about 0.2% of the percentage of a comparative composition effluxed by P-gp following the oral administration, wherein the sublingual or buccal and oral administrations are at the same delivery dose.

Embodiment 292 provides the method of any one of embodiments 181-288, wherein the percentage of a composition effluxed by P-gp following the sublingual or buccal administration is about 0.3% of the percentage of a comparative composition effluxed by P-gp following the oral administration, wherein the sublingual or buccal and oral administrations are at the same delivery dose.

Embodiment 293 provides the method of any one of embodiments 181-288, wherein the percentage of a composition effluxed by P-gp following the sublingual or buccal administration is about 0.4% of the percentage of a comparative composition effluxed by P-gp following the oral administration, wherein the sublingual or buccal and oral administrations are at the same delivery dose.

Embodiment 294 provides the method of any one of embodiments 181-288, wherein the percentage of a composition effluxed by P-gp following the sublingual or buccal administration is about 0.5% of the percentage of a comparative composition effluxed by P-gp following the oral administration, wherein the sublingual or buccal and oral administrations are at the same delivery dose.

Embodiment 295 provides the method of any one of embodiments 181-288, wherein the percentage of a composition effluxed by P-gp following the sublingual or buccal administration is about 1% of the percentage of a comparative composition effluxed by P-gp following the oral administration, wherein the sublingual or buccal and oral administrations are at the same delivery dose.

Embodiment 296 provides the method of any one of embodiments 181-288, wherein the percentage of a composition effluxed by P-gp following the sublingual or buccal administration is about 2% of the percentage of a comparative composition effluxed by P-gp following the oral administration, wherein the sublingual or buccal and oral administrations are at the same delivery dose.

Embodiment 297 provides the method of any one of embodiments 181-288, wherein the percentage of a composition effluxed by P-gp following the sublingual or buccal administration is about 3% of the percentage of a comparative composition effluxed by P-gp following the oral administration, wherein the sublingual or buccal and oral administrations are at the same delivery dose.

Embodiment 298 provides the method of any one of embodiments 181-288, wherein the percentage of a composition effluxed by P-gp following the sublingual or buccal administration is about 4% of the percentage of a comparative composition effluxed by P-gp following the oral administration, wherein the sublingual or buccal and oral administrations are at the same delivery dose.

Embodiment 299 provides the method of any one of embodiments 181-288, wherein the percentage of a composition effluxed by P-gp following the sublingual or buccal administration is about 5% of the percentage of a comparative composition effluxed by P-gp following the oral administration, wherein the sublingual or buccal and oral administrations are at the same delivery dose.

Embodiment 300 provides the method of any one of embodiments 181-288, wherein the percentage of a composition effluxed by P-gp following the sublingual or buccal administration is about 6% of the percentage of a comparative composition effluxed by P-gp following the oral administration, wherein the sublingual or buccal and oral administrations are at the same delivery dose.

Embodiment 301 provides the method of any one of embodiments 181-288, wherein the percentage of a composition effluxed by P-gp following the sublingual or buccal administration is about 7% of the percentage of a comparative composition effluxed by P-gp following the oral administration, wherein the sublingual or buccal and oral administrations are at the same delivery dose.

Embodiment 302 provides the method of any one of embodiments 181-288, wherein the percentage of a composition effluxed by P-gp following the sublingual or buccal administration is about 8% of the percentage of a comparative composition effluxed by P-gp following the oral administration, wherein the sublingual or buccal and oral administrations are at the same delivery dose.

Embodiment 303 provides the method of any one of embodiments 181-288, wherein the percentage of a composition effluxed by P-gp following the sublingual or buccal administration is about 9% of the percentage of a comparative composition effluxed by P-gp following the oral administration, wherein the sublingual or buccal and oral administrations are at the same delivery dose.

Embodiment 304 provides the method of any one of embodiments 181-288, wherein the percentage of a composition effluxed by P-gp following the sublingual or buccal administration is about 10% of the percentage of a comparative composition effluxed by P-gp following the oral administration, wherein the sublingual or buccal and oral administrations are at the same delivery dose.

Embodiment 305 provides the method of any one of embodiments 181-288, wherein the percentage of a composition effluxed by P-gp following the sublingual or buccal administration is about 20% of the percentage of a comparative composition effluxed by P-gp following the oral administration, wherein the sublingual or buccal and oral administrations are at the same delivery dose.

Embodiment 306 provides the method of any one of embodiments 181-288, wherein the percentage of a composition effluxed by P-gp following the sublingual or buccal administration is about 30% of the percentage of a comparative composition effluxed by P-gp following the oral administration, wherein the sublingual or buccal and oral administrations are at the same delivery dose.

Embodiment 307 provides the method of any one of embodiments 181-288, wherein the percentage of a composition effluxed by P-gp following the sublingual or buccal administration is about 40% of the percentage of a comparative composition effluxed by P-gp following the oral administration, wherein the sublingual or buccal and oral administrations are at the same delivery dose.

Embodiment 308 provides the method of any one of embodiments 181-288, wherein the percentage of a composition effluxed by P-gp following the sublingual or buccal administration is about 50% of the percentage of a comparative composition effluxed by P-gp following the oral administration, wherein the sublingual or buccal and oral administrations are at the same delivery dose.

Embodiment 309 provides the method of any one of embodiments 289-308, wherein the percentage of a composition effluxed by P-gp following the sublingual or buccal administration and the percentage of a comparative composition effluxed by P-gp following the oral administration are based on a dosage of administration comprising at least 15 mg of the substituted or unsubstituted diindolylmethane.

Embodiment 310 provides the method of any one of embodiments 181-309, wherein the percentage of a composition influxed by an OATP following the sublingual or buccal administration is about 0.1% to about 50% of the percentage of a comparative composition influxed by an OATP following the oral administration, wherein the sublingual or buccal and oral administrations are at the same delivery dose.

Embodiment 311 provides the method of any one of embodiments 181-309, wherein the percentage of a composition influxed by an OATP following the sublingual or buccal administration is about 0.1% of the percentage of a comparative composition influxed by an OATP following the oral administration, wherein the sublingual or buccal and oral administrations are at the same delivery dose.

Embodiment 312 provides the method of any one of embodiments 181-309, wherein the percentage of a composition influxed by an OATP following the sublingual or buccal administration is about 0.2% of the percentage of a comparative composition influxed by an OATP following the oral administration, wherein the sublingual or buccal and oral administrations are at the same delivery dose.

Embodiment 313 provides the method of any one of embodiments 181-309, wherein the percentage of a composition influxed by an OATP following the sublingual or buccal administration is about 0.3% of the percentage of a comparative composition influxed by an OATP following the oral administration, wherein the sublingual or buccal and oral administrations are at the same delivery dose.

Embodiment 314 provides the method of any one of embodiments 181-309, wherein the percentage of a composition influxed by an OATP following the sublingual or buccal administration is about 0.4% of the percentage of a comparative composition influxed by an OATP following the oral administration, wherein the sublingual or buccal and oral administrations are at the same delivery dose.

Embodiment 315 provides the method of any one of embodiments 181-309, wherein the percentage of a composition influxed by an OATP following the sublingual or buccal administration is about 0.5% of the percentage of a comparative composition influxed by an OATP following the oral administration, wherein the sublingual or buccal and oral administrations are at the same delivery dose.

Embodiment 316 provides the method of any one of embodiments 181-309, wherein the percentage of a composition influxed by an OATP following the sublingual or buccal administration is about 0.6% of the percentage of a comparative composition influxed by an OATP following the oral administration, wherein the sublingual or buccal and oral administrations are at the same delivery dose.

Embodiment 317 provides the method of any one of embodiments 181-309, wherein the percentage of a composition influxed by an OATP following the sublingual or buccal administration is about 0.7% of the percentage of a comparative composition influxed by an OATP following the oral administration, wherein the sublingual or buccal and oral administrations are at the same delivery dose.

Embodiment 318 provides the method of any one of embodiments 181-309, wherein the percentage of a composition influxed by an OATP following the sublingual or buccal administration is about 0.8% of the percentage of a comparative composition influxed by an OATP following the oral administration, wherein the sublingual or buccal and oral administrations are at the same delivery dose.

Embodiment 319 provides the method of any one of embodiments 181-309, wherein the percentage of a composition influxed by an OATP following the sublingual or buccal administration is about 0.9% of the percentage of a comparative composition influxed by an OATP following the oral administration, wherein the sublingual or buccal and oral administrations are at the same delivery dose.

Embodiment 320 provides the method of any one of embodiments 181-309, wherein the percentage of a composition influxed by an OATP following the sublingual or buccal administration is about 1% of the percentage of a comparative composition influxed by an OATP following the oral administration, wherein the sublingual or buccal and oral administrations are at the same delivery dose.

Embodiment 321 provides the method of any one of embodiments 181-309, wherein the percentage of a composition influxed by an OATP following the sublingual or buccal administration is about 2% of the percentage of a comparative composition influxed by an OATP following the oral administration, wherein the sublingual or buccal and oral administrations are at the same delivery dose.

Embodiment 322 provides the method of any one of embodiments 181-309, wherein the percentage of a composition influxed by an OATP following the sublingual or buccal administration is about 3% of the percentage of a comparative composition influxed by an OATP following the oral administration, wherein the sublingual or buccal and oral administrations are at the same delivery dose.

Embodiment 323 provides the method of any one of embodiments 181-309, wherein the percentage of a composition influxed by an OATP following the sublingual or buccal administration is about 4% of the percentage of a comparative composition influxed by an OATP following the oral administration, wherein the sublingual or buccal and oral administrations are at the same delivery dose.

Embodiment 324 provides the method of any one of embodiments 181-309, wherein the percentage of a composition influxed by an OATP following the sublingual or buccal administration is about 5% of the percentage of a comparative composition influxed by an OATP following the oral administration, wherein the sublingual or buccal and oral administrations are at the same delivery dose.

Embodiment 325 provides the method of any one of embodiments 181-309, wherein the percentage of a composition influxed by an OATP following the sublingual or buccal administration is about 6% of the percentage of a comparative composition influxed by an OATP following the oral administration, wherein the sublingual or buccal and oral administrations are at the same delivery dose.

Embodiment 326 provides the method of any one of embodiments 181-309, wherein the percentage of a composition influxed by an OATP following the sublingual or buccal administration is about 7% of the percentage of a comparative composition influxed by an OATP following the oral administration, wherein the sublingual or buccal and oral administrations are at the same delivery dose.

Embodiment 327 provides the method of any one of embodiments 181-309, wherein the percentage of a composition influxed by an OATP following the sublingual or buccal administration is about 8% of the percentage of a comparative composition influxed by an OATP following the oral administration, wherein the sublingual or buccal and oral administrations are at the same delivery dose.

Embodiment 328 provides the method of any one of embodiments 181-309, wherein the percentage of a composition influxed by an OATP following the sublingual or buccal administration is about 9% of the percentage of a comparative composition influxed by an OATP following the oral administration, wherein the sublingual or buccal and oral administrations are at the same delivery dose.

Embodiment 329 provides the method of any one of embodiments 181-309, wherein the percentage of a composition influxed by an OATP following the sublingual or buccal administration is about 10% of the percentage of a comparative composition influxed by an OATP following the oral administration, wherein the sublingual or buccal and oral administrations are at the same delivery dose.

Embodiment 330 provides the method of any one of embodiments 181-309, wherein the percentage of a composition influxed by an OATP following the sublingual or buccal administration is about 20% of the percentage of a comparative composition influxed by an OATP following the oral administration, wherein the sublingual or buccal and oral administrations are at the same delivery dose.

Embodiment 331 provides the method of any one of embodiments 181-309, wherein the percentage of a composition influxed by an OATP following the sublingual or buccal administration is about 30% of the percentage of a comparative composition influxed by an OATP following the oral administration, wherein the sublingual or buccal and oral administrations are at the same delivery dose.

Embodiment 332 provides the method of any one of embodiments 181-309, wherein the percentage of a composition influxed by an OATP following the sublingual or buccal administration is about 40% of the percentage of a comparative composition influxed by an OATP following the oral administration, wherein the sublingual or buccal and oral administrations are at the same delivery dose.

Embodiment 333 provides the method of any one of embodiments 181-309, wherein the percentage of a composition influxed by an OATP following the sublingual or buccal administration is about 50% of the percentage of a comparative composition influxed by an OATP following the oral administration, wherein the sublingual or buccal and oral administrations are at the same delivery dose.

Embodiment 334 provides the method of any one of embodiments 310-333, wherein the percentage of a composition influxed by an OATP following the sublingual or buccal administration and the percentage of a comparative composition influxed by an OATP following the oral administration are based on a dosage of administration comprising at least 15 mg of the substituted or unsubstituted diindolylmethane.

Embodiment 335 provides the method of any one of embodiments 181-334, wherein the percentage of a composition metabolized by CYP3A4, CYP1A2, or CYP2B6, following the sublingual or buccal administration is about 0.1% to about 50% of the percentage of a comparative composition metabolized by CYP3A4, CYP1A2, or CYP2B6, following the oral administration, wherein the sublingual or buccal and oral administrations are at the same delivery dose.

Embodiment 336 provides the method of any one of embodiments 181-334, wherein the percentage of a composition metabolized by CYP3A4, CYP1A2, or CYP2B6, following the sublingual or buccal administration is about 0.1% of the percentage of a comparative composition metabolized by CYP3A4, CYP1A2, or CYP2B6, following the oral administration, wherein the sublingual or buccal and oral administrations are at the same delivery dose.

Embodiment 337 provides the method of any one of embodiments 181-334, wherein the percentage of a composition metabolized by CYP3A4, CYP1A2, or CYP2B6, following the sublingual or buccal administration is about 0.2% of the percentage of a comparative composition metabolized by CYP3A4, CYP1A2, or CYP2B6, following the oral administration, wherein the sublingual or buccal and oral administrations are at the same delivery dose.

Embodiment 338 provides the method of any one of embodiments 181-334, wherein the percentage of a composition metabolized by CYP3A4, CYP1A2, or CYP2B6, following the sublingual or buccal administration is about 0.3% of the percentage of a comparative composition metabolized by CYP3A4, CYP1A2, or CYP2B6, following the oral administration, wherein the sublingual or buccal and oral administrations are at the same delivery dose.

Embodiment 339 provides the method of any one of embodiments 181-334, wherein the percentage of a composition metabolized by CYP3A4, CYP1A2, or CYP2B6, following the sublingual or buccal administration is about 0.4% of the percentage of a comparative composition metabolized by CYP3A4, CYP1A2, or CYP2B6, following the oral administration, wherein the sublingual or buccal and oral administrations are at the same delivery dose.

Embodiment 340 provides the method of any one of embodiments 181-334, wherein the percentage of a composition metabolized by CYP3A4, CYP1A2, or CYP2B6, following the sublingual or buccal administration is about 0.5% of the percentage of a comparative composition metabolized by CYP3A4, CYP1A2, or CYP2B6, following the oral administration, wherein the sublingual or buccal and oral administrations are at the same delivery dose.

Embodiment 341 provides the method of any one of embodiments 181-334, wherein the percentage of a composition metabolized by CYP3A4, CYP1A2, or CYP2B6, following the sublingual or buccal administration is about 0.6% of the percentage of a comparative composition metabolized by CYP3A4, CYP1A2, or CYP2B6, following the oral administration, wherein the sublingual or buccal and oral administrations are at the same delivery dose.

Embodiment 342 provides the method of any one of embodiments 181-334, wherein the percentage of a composition metabolized by CYP3A4, CYP1A2, or CYP2B6, following the sublingual or buccal administration is about 0.7% of the percentage of a comparative composition metabolized by CYP3A4, CYP1A2, or CYP2B6, following the oral administration, wherein the sublingual or buccal and oral administrations are at the same delivery dose.

Embodiment 343 provides the method of any one of embodiments 181-334, wherein the percentage of a composition metabolized by CYP3A4, CYP1A2, or CYP2B6, following the sublingual or buccal administration is about 0.8% of the percentage of a comparative composition metabolized by CYP3A4, CYP1A2, or CYP2B6, following the oral administration, wherein the sublingual or buccal and oral administrations are at the same delivery dose.

Embodiment 344 provides the method of any one of embodiments 181-334, wherein the percentage of a composition metabolized by CYP3A4, CYP1A2, or CYP2B6, following the sublingual or buccal administration is about 0.9% of the percentage of a comparative composition metabolized by CYP3A4, CYP1A2, or CYP2B6, following the oral administration, wherein the sublingual or buccal and oral administrations are at the same delivery dose.

Embodiment 345 provides the method of any one of embodiments 181-334, wherein the percentage of a composition metabolized by CYP3A4, CYP1A2, or CYP2B6, following the sublingual or buccal administration is about 1% of the percentage of a comparative composition metabolized by CYP3A4, CYP1A2, or CYP2B6, following the oral administration, wherein the sublingual or buccal and oral administrations are at the same delivery dose.

Embodiment 346 provides the method of any one of embodiments 181-334, wherein the percentage of a composition metabolized by CYP3A4, CYP1A2, or CYP2B6, following the sublingual or buccal administration is about 2% of the percentage of a comparative composition metabolized by CYP3A4, CYP1A2, or CYP2B6, following the oral administration, wherein the sublingual or buccal and oral administrations are at the same delivery dose.

Embodiment 347 provides the method of any one of embodiments 181-334, wherein the percentage of a composition metabolized by CYP3A4, CYP1A2, or CYP2B6, following the sublingual or buccal administration is about 3% of the percentage of a comparative composition metabolized by CYP3A4, CYP1A2, or CYP2B6, following the oral administration, wherein the sublingual or buccal and oral administrations are at the same delivery dose.

Embodiment 348 provides the method of any one of embodiments 181-334, wherein the percentage of a composition metabolized by CYP3A4, CYP1A2, or CYP2B6, following the sublingual or buccal administration is about 4% of the percentage of a comparative composition metabolized by CYP3A4, CYP1A2, or CYP2B6, following the oral administration, wherein the sublingual or buccal and oral administrations are at the same delivery dose.

Embodiment 349 provides the method of any one of embodiments 181-334, wherein the percentage of a composition metabolized by CYP3A4, CYP1A2, or CYP2B6, following the sublingual or buccal administration is about 5% of the percentage of a comparative composition metabolized by CYP3A4, CYP1A2, or CYP2B6, following the oral administration, wherein the sublingual or buccal and oral administrations are at the same delivery dose.

Embodiment 350 provides the method of any one of embodiments 181-334, wherein the percentage of a composition metabolized by CYP3A4, CYP1A2, or CYP2B6, following the sublingual or buccal administration is about 6% of the percentage of a comparative composition metabolized by CYP3A4, CYP1A2, or CYP2B6, following the oral administration, wherein the sublingual or buccal and oral administrations are at the same delivery dose.

Embodiment 351 provides the method of any one of embodiments 181-334, wherein the percentage of a composition metabolized by CYP3A4, CYP1A2, or CYP2B6, following the sublingual or buccal administration is about 7% of the percentage of a comparative composition metabolized by CYP3A4, CYP1A2, or CYP2B6, following the oral administration, wherein the sublingual or buccal and oral administrations are at the same delivery dose.

Embodiment 352 provides the method of any one of embodiments 181-334, wherein the percentage of a composition metabolized by CYP3A4, CYP1A2, or CYP2B6, following the sublingual or buccal administration is about 8% of the percentage of a comparative composition metabolized by CYP3A4, CYP1A2, or CYP2B6, following the oral administration, wherein the sublingual or buccal and oral administrations are at the same delivery dose.

Embodiment 353 provides the method of any one of embodiments 181-334, wherein the percentage of a composition metabolized by CYP3A4, CYP1A2, or CYP2B6, following the sublingual or buccal administration is about 9% of the percentage of a comparative composition metabolized by CYP3A4, CYP1A2, or CYP2B6, following the oral administration, wherein the sublingual or buccal and oral administrations are at the same delivery dose.

Embodiment 354 provides the method of any one of embodiments 181-334, wherein the percentage of a composition metabolized by CYP3A4, CYP1A2, or CYP2B6, following the sublingual or buccal administration is about 10% of the percentage of a comparative composition metabolized by CYP3A4, CYP1A2, or CYP2B6, following the oral administration, wherein the sublingual or buccal and oral administrations are at the same delivery dose.

Embodiment 355 provides the method of any one of embodiments 181-334, wherein the percentage of a composition metabolized by CYP3A4, CYP1A2, or CYP2B6, following the sublingual or buccal administration is about 20% of the percentage of a comparative composition metabolized by CYP3A4, CYP1A2, or CYP2B6, following the oral administration, wherein the sublingual or buccal and oral administrations are at the same delivery dose.

Embodiment 356 provides the method of any one of embodiments 181-334, wherein the percentage of a composition metabolized by CYP3A4, CYP1A2, or CYP2B6, following the sublingual or buccal administration is about 30% of the percentage of a comparative composition metabolized by CYP3A4, CYP1A2, or CYP2B6, following the oral administration, wherein the sublingual or buccal and oral administrations are at the same delivery dose.

Embodiment 357 provides the method of any one of embodiments 181-334, wherein the percentage of a composition metabolized by CYP3A4, CYP1A2, or CYP2B6, following the sublingual or buccal administration is about 40% of the percentage of a comparative composition metabolized by CYP3A4, CYP1A2, or CYP2B6, following the oral administration, wherein the sublingual or buccal and oral administrations are at the same delivery dose.

Embodiment 358 provides the method of any one of embodiments 181-334, wherein the percentage of a composition metabolized by CYP3A4, CYP1A2, or CYP2B6, following the sublingual or buccal administration is about 50% of the percentage of a comparative composition metabolized by CYP3A4, CYP1A2, or CYP2B6, following the oral administration, wherein the sublingual or buccal and oral administrations are at the same delivery dose.

Embodiment 359 provides the method of any one of embodiments 335-358, wherein the percentage of a composition metabolized by CYP3A4, CYP1A2, or CYP2B6, following the sublingual or buccal administration and the percentage of a comparative composition metabolized by CYP3A4, CYP1A2, or CYP2B6, following the oral administration are based on a dosage of administration comprising at least 15 mg of the substituted or unsubstituted diindolylmethane.

Embodiment 360 provides the method of any one of embodiments 181-359, wherein the composition is administered in a dosage form that disintegrates when placed in the sublingual or buccal cavity.

What is claimed is:

1. A method of treating acne in a subject in need thereof comprising administering to the subject a composition comprising a substituted or unsubstituted diindolylmethane and optionally a substituted or unsubstituted retinoic acid based component, wherein the composition is administered by a sublingual or buccal route, wherein the composition is in a solid dosage form that disintegrates when placed in the sublingual or buccal cavity, and wherein the composition provides a daily dose of from 80 mg to 100 mg of the substituted or unsubstituted diindolylmethane.

2. The method of claim 1, wherein the retinoic acid based component is vitamin A.

3. The method of claim 1, wherein the composition further comprises a vitamin A palmitate.

4. The method of claim 1, wherein the administration of the composition by the sublingual or buccal route increases bioavailability of the substituted or unsubstituted diindolylmethane by about 1-fold to about 50-fold compared to bioavailability of a substituted or unsubstituted diindolylmethane of a comparative composition administered by oral route at the same delivery dose.

5. The method of claim 1, wherein following administration of the composition by the sublingual or buccal route Cmax of the substituted or unsubstituted diindolylmethane in plasma increases by about 1-fold to about 50-fold compared to Cmax of a substituted or unsubstituted diindolylmethane of a comparative composition administered by oral route at the same delivery dose.

6. The method of claim 1, wherein following administration of the composition by the sublingual or buccal route the AUC of the substituted or unsubstituted diindolylmethane in plasma increases by about 1-fold to about 50-fold compared to the AUC of a substituted or unsubstituted diindolylmethane of a comparative composition administered by oral route at the same delivery dose.

7. The method of claim 1, wherein following administration of the composition by the sublingual or buccal route the Tmax of the substituted or unsubstituted diindolylmethane in plasma decreases by about 1-fold to about 50-fold compared to the Tmax of a substituted or unsubstituted diindolylmethane of a comparative composition administered by oral route at the same delivery dose.

8. The method of claim 1, wherein a percentage of the composition effluxed by P-gp following the sublingual or buccal administration is about 0.1% to about 50% of a percentage of a comparative composition effluxed by P-gp following oral administration, wherein the sublingual or buccal and the oral administrations are at the same delivery dose.

9. The method of claim 1, wherein a percentage of the composition influxed by an OATP following the sublingual or buccal administration is about 0.1% to about 50% of a percentage of a comparative composition influxed by the OATP following oral administration, wherein the sublingual or buccal and the oral administrations are at the same delivery dose.

10. The method of claim 1, wherein a percentage of the composition metabolized by CYP3A4, CYP1A2, or CYP2B6, following the sublingual or buccal administration is about 0.1% to about 50% of a percentage of a comparative composition metabolized by CYP3A4, CYP1A2, or CYP2B6, following oral administration, wherein the sublingual or buccal and the oral administrations are at the same delivery dose.

* * * * *